(12) United States Patent
Brito et al.

(10) Patent No.: US 10,238,733 B2
(45) Date of Patent: *Mar. 26, 2019

(54) CATIONIC OIL-IN-WATER EMULSIONS

(71) Applicant: GlaxoSmithKline Biologicals SA, Rixensart (BE)

(72) Inventors: Luis Brito, Lincoln, MA (US); Andrew Geall, Carlsbad, CA (US); Derek O'Hagan, Winchester, MA (US); Manmohan Singh, Cary, NC (US)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 257 days.

This patent is subject to a terminal disclaimer.

(21) Appl. No.: 15/067,216

(22) Filed: Mar. 11, 2016

(65) Prior Publication Data
US 2016/0256541 A1 Sep. 8, 2016

Related U.S. Application Data

(63) Continuation of application No. 13/235,454, filed on Sep. 18, 2011, now Pat. No. 9,295,646, which is a continuation of application No. PCT/US2011/043108, filed on Jul. 6, 2011.

(60) Provisional application No. 61/361,892, filed on Jul. 6, 2010.

(51) Int. Cl.
| A61K 39/395 | (2006.01) |
| A61K 39/385 | (2006.01) |
| A61K 9/107  | (2006.01) |
| A61K 39/39  | (2006.01) |
| A61K 39/00  | (2006.01) |

(52) U.S. Cl.
CPC ............ *A61K 39/385* (2013.01); *A61K 9/107* (2013.01); *A61K 39/39* (2013.01); *A61K 2039/53* (2013.01); *A61K 2039/55566* (2013.01)

(58) Field of Classification Search
None
See application file for complete search history.

(56) References Cited

U.S. PATENT DOCUMENTS

| 5,264,618 A | 11/1993 | Felgner et al. |
| 5,795,587 A | 8/1998 | Gao et al. |
| 6,171,586 B1 | 1/2001 | Lam et al. |
| 6,299,884 B1 | 10/2001 | Van Nest et al. |
| 6,451,325 B1 | 9/2002 | Van Nest et al. |
| 6,610,321 B2 | 8/2003 | Huang et al. |
| 6,890,554 B2 | 5/2005 | Jessee et al. |
| 7,303,881 B2 | 12/2007 | Huang et al. |
| 7,314,627 B2 | 1/2008 | Haynes et al. |
| 7,550,145 B2 | 6/2009 | O'Hagan et al. |
| 7,641,911 B2 | 1/2010 | Ott et al. |
| 7,749,520 B2 | 7/2010 | Davidsen et al. |
| 7,790,696 B2 | 9/2010 | Gregoriadis |
| 9,295,646 B2 * | 3/2016 | Brito ................. A61K 9/107 |
| 2009/0017057 A1 | 1/2009 | Chen et al. |
| 2011/0110972 A1 | 5/2011 | Vasievich et al. |
| 2013/0195968 A1 | 8/2013 | Geall et al. |

FOREIGN PATENT DOCUMENTS

| EP | 1723972 | 11/2006 |
| WO | WO 90/014837 A1 | 12/1990 |
| WO | WO 96/22765 A1 | 8/1996 |
| WO | WO 1997/011682 A2 | 4/1997 |
| WO | WO 1999/02132 A2 | 1/1999 |
| WO | WO 2000/50006 A2 | 8/2000 |
| WO | WO 2003/028656 | 4/2003 |
| WO | WO 2004/053056 A2 | 6/2004 |
| WO | WO 2008/116078 A2 | 9/2008 |
| WO | WO 2009/129227 A1 | 10/2009 |
| WO | WO 2010/009277 A2 | 1/2010 |
| WO | WO 20111005799 A2 | 1/2011 |

OTHER PUBLICATIONS

Brito, et al. "A Catonic Nanoemulsion for Delivery of Next-generation RNA Vaccines" The American Society of Gene & Cell Therapy 1-12 (2014).

Brgles et al., "Liposome fusogenicity and entrapment efficiency of antigen determine the Th1/Th2 bias of antigen-specific immune response", Vaccine 27: 5435-5442 (2009).

Choi et ai, "Low toxicity of cationic lipid-based emulsion for gene transfer", Biomaterials 25(27):5893-5903 (2004).

Chung, H., et al. "Oil components modulate physical characteristics and function of the natural oil emulsions as drug or gene delivery system", J. Control Release, 71 (3) 339-350 (2001).

Elbashir, et al (2001). Duplexes of 21-nucleotide RNAs mediate RNA interference in cultured mammalian cells. Nature, 411 (6836), 494-8.

Fire et al., (1999). RNA-triggered gene silencing, Trends in Genetics vol. 15, pp. 358-363.

Gregoriadis et al. "Liposome-mediated DNA vaccination" FEBS Letters 402107-110 (1997).

Guy, B. (2007). The perfect mix: recent progress in adjuvant research. Nature Reviews. Microbiology, 5(7), 505-17.

Hagigit, et al., "The influence of cationic lipid type on in-vitro release kinetic profiles of antisense oligonucleotide from cationic nanoemulsions" Eur J Pharm Biopharm, 70( 1): 248-259 (2008).

Hoerr, "In vivo application of RNA leads to induction of specific cytotoxic T lymphocytes and antibodies", Eur. J. Immunol. 30: 1-7 (2000).

Hung, et al., "Physicochemical characterization and gene transfection efficiency of lipid emulsions with various co-emulsifiers" Int. J. Pharm. 289(1-2): 197-208 (2005).

(Continued)

Primary Examiner — Yunsoo Kim

(57) ABSTRACT

This invention generally relates to cationic oil-in-water emulsions that can be used to deliver negatively charged molecules, such as an RNA molecule. The emulsion particles comprise an oil core and a cationic lipid. The cationic lipid can interact with the negatively charged molecule thereby anchoring the molecule to the emulsion particles. The cationic emulsions described herein are particularly suitable for delivering nucleic acid molecules (such as an RNA molecule encoding an antigen) to cells and formulating nucleic acid-based vaccines.

32 Claims, 24 Drawing Sheets

Specification includes a Sequence Listing.

(56) References Cited

OTHER PUBLICATIONS

Kang, et al., "Delivery of interleukin-18 gene to lung cancer cells using cationic emulsion", J. Drug Target 17(1): 19-28 (2009).

Kim, TW., et al., "Optimization of Lipid Composition in Cationic Emulsion as In Vitro and In Vivo Transfection Agents", Pharm. Res. 18(1): 54-60 (2001).

Kim, et al., "Polycations enhance emulsion-mediated in vitro and in vivo transfection", In!. J. Pharrn. 295(1-2): 35-45 (2005).

Kim, et al., "Airway gene transfer using cationic emulsion as a mucosal gene carrier", J. Gene Med, 7(6): 749-758 (2005).

Kwon, et al., "In vivo time-dependent gene expression of cationic lipid-based emulsion as a stable and biocompatible non-viral gene carrier", J. Control Release 128(1): 89-97 (2008).

Lee, et al (2005). Novel molecular approaches to cystic fibrosis gene therapy. The Biochemical Journal, 387(Pt 1), 1-15.

Malone et al., "Catonic liposome-mediated RNA transfection", Proc. Natl. Acad. Sci. USA 86:16 6077-6081 (1989).

Martinon et al., "Induction of virus-specific cytotoxic T lymphocytes in vivo by liposome-entrapped mRNA", Eur. J. Immunol. 23: 1719-1722 (1993).

Min et ai, "Improved gene expression pattern using Epstein-Barr virus (EBV)-based plasmid and cationic emulsion", Biomaterials 26: 1063-1070 (2005).

Montana, "Employment of Cationic Solid-Lipid Nanoparticles as RNA Carriers", Bioconjugate Chem. 18: 302-308 (2007).

Moret et al., "Stability of PEI-DNA and DOTAP-DNA complexes: effect of alkaline pH, heparin and serum", J. Controlled Release 76:169-181 (2001).

Muhlen et al., "Solid Lipid Nanoparticles (SLN) for Controled Drug Delivery—Drug Release and Release Mechanism", Eur. J. of Pharmaceutics and Biopharmaceutics 45:149-155 (1998).

Nam, et al., "Lipid-based emulsion system as non-viral gene carriers", Arch. Pharm. Res. 32(5): 639-646 (2009).

Ott, G., et al., "A cationic sub-micron emulsion (MF59/DOTAP) is an effective delivery system for DNA vaccines", J. Control Release, 79(1-3): 1-5 (2002).

Perrie, Y., et al., "Liposome-mediated DNA vaccination: the effect of vesicle composition", Vaccine 19:3301-3310 (2001 ).

Shi et al., "TLR4 links innate immunity and fatty acid-induced insulin resistance", J. Clin. Invest. 116: 3015-3025 (2006).

Simberg. D., et al., "DOTAP (and Other Cationic Lipids): Chemistry, Biophysics, and Transfection", Crit. Rev. In Therapeu. Drug Carrier Systems 21(4):257-317 (2004).

Tabatt et al., "Effect of Cationic Lipid and Matrix Lipid Composition on Solid Lipid Nanoparticle-mediated Gene Transfer", Eur. J. Pharmaceut. Biopharmaceut. 57:155-162 (2004).

Vajdy, et al., "Mucosal adjuvants and delivery systems for protein-, DNA- and RNA-based vaccines", Immunol. Cell Biol. 82(6): 617-627 (2004).

Walker, C., et al., "Cationic lipids direct a viral glycoprotein into the class I major histocompatibility complex antigen—presentation pathway", Proc. Natl. Acad. Sci. USA 89:7915-7918 (1992).

Yew, N.S., et al., "Toxicity of Cationic Lipid-DNA Complexes", Adv. In Genetics 53: 189-214 (2005).

Yi, SW.,et ai, "A cationic lipid emulsion/DNA complex as a physically stable and serum-resistant gene delivery system", Pharm. Res. 17(3): 314-320 (2000).

Ying "Cancer therapy using a self-replicating RNA vaccine", Nature Medicine, 5: 823-827 (1999).

Yoo, et al., "In vivo gene therapy of type 1 diabetic mellitus using a cationic emulsion containing an Epstein Barr Virus (EBY) based plasmid vector", J. Control Release 112(1): 139-144 (2006).

Bramson, J.L., et al., "Activiation of host antitumoral respones by cationic lipid/DNA complexes", Cancer Gene Therapy 7(3):353-359 (2000).

Dow, S.W., et al., "Lipid-DNA Complexes Induce Potent Activiation of Innate Immune Responses and Antitumor Activity When Administered Intravenously", J_ Immunol. 163:1552-1561 (1999).

\* cited by examiner

FIG. 7A

ATAGGCGGCGCATGAGAGAAGCCCAGACCAATTACCTACCCAAAATGGAGAAAGTTCACGTTGACATC
GAGGAAGACAGCCCATTCCTCAGAGCTTTGCAGCGGAGCTTCCCGCAGTTTGAGGTAGAAGCCAAGCA
GGTCACTGATAATGACCATGCTAATGCCAGAGCGTTTTCGCATCTGGCTTCAAAACTGATCGAAACGG
AGGTGGACCCATCCGACACGATCCTTGACATTGGAAGTGCGCCCGCCCGCAGAATGTATTCTAAGCAC
AAGTATCATTGTATCTGTCCGATGAGATGTGCGGAAGATCCGGACAGATTGTATAAGTATGCAACTAA
GCTGAAGAAAACTGTAAGGAAATAACTGATAAGGAATTGGACAAGAAAATGAAGGAGCTCGCCGCCG
TCATGAGCGACCCTGACCTGGAAACTGAGACTATGTGCCTCCACGACGACGAGTCGTGTCGCTACGAA
GGGCAAGTCGCTGTTTACCAGGATGTATACGCGGTTGACGGACCGACAAGTCTCTATCACCAAGCCAA
TAAGGGAGTTAGAGTCGCCTACTGGATAGGCTTTGACACCACCCCTTTTATGTTTAAGAACTTGGCTG
GAGCATATCCATCATACTCTACCAACTGGGCCGACGAAACCGTGTTAACGGCTCGTAACATAGGCCTA
TGCAGCTCTGACGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTTACTGAGGAGCT
GGCACCTGCCGTCTGTATTTCACTTACGTGGCAAGCAAAATTACACATGTCGGTGTGAGACTATAGTT
AGTTGCGACGGGTACGTCGTTAAAAGAATAGCTATCAGTCCAGGCCTGTATGGGAAGCCTTCAGGCTA
TGCTGCTACGATGCACCGCGAGGGATTCTTGTGCTGCAAAGTGACAGACACATTGAACGGGGAGAGGG
TCTCTTTTCCCGTGTGCACGTATGTGCCAGCTACATTGTGTGACCAAATGACTGGCATACTGGCAACA
GATGTCAGTGCGGACGACGCGCAAAAACTGCTGGTTGGGCTCAACCAGCGTATAGTCGTCAACGGTCG
CACCCAGAGAAACACCAATACCATGAAAAATTACCTTTTGCCCGTAGTGGCCCAGGCATTTGCTAGGT
GGGCAAAGGAATATAAGGAAGATCAAGAAGATGAAAGGCCACTAGGACTACGAGATAGACAGTTAGTC
ATGGGGTGTTGTTGGGCTTTTAGAAGGCACAAGATAACATCTATTTATAAGCGCCCGGATACCCAAAC
CATCATCAAAGTGAACAGCGATTTCCACTCATTCGTGCTGCCCAGGATAGGCAGTAACACATTGGAGA
TCGGGCTGAGAACAAGAATCAGGAAAATGTTAGAGGAGCACAAGGAGCCGTCACCTCTCATTACCGCC
GAGGACGTACAAGAAGCTAAGTGCGCAGCCGATGAGGCTAAGGAGGTGCGTGAAGCCGAGGAGTTGCG
CGCAGCTCTACCACCTTTGGCAGCTGATGTTGAGGAGCCCACTCTGGAAGCCGATGTAGACTTGATGT
TACAAGAGGCTGGGGCCGGCTCAGTGGAGACACCTCGTGGCTTGATAAAGGTTACCAGCTACGATGGC
GAGGACAAGATCGGCTCTTACGCTGTGCTTTCTCCGCAGGCTGTACTCAAGAGTGAAAAATTATCTTG
CATCCACCCTCTCGCTGAACAAGTCATAGTGATAACACACTCTGGCCGAAAAGGGCGTTATGCCGTGG
AACCATACCATGGTAAAGTAGTGGTGCCAGAGGGACATGCAATACCCGTCCAGGACTTTCAAGCTCTG
AGTGAAAGTGCCACCATTGTGTACAACGAACGTGAGTTCGTAAACAGGTACCTGCACCATATTGCCAC
ACATGGAGGAGCGCTGAACACTGATGAAGAATATTACAAAACTGTCAAGCCCAGCGAGCACGACGGCG
AATACCTGTACGACATCGACAGGAAACAGTGCGTCAAGAAAGAACTAGTCACTGGGCTAGGCTCACA
GGCGAGCTGGTGGATCCTCCCTTCCATGAATTCGCCTACGAGAGTCTGAGAACACGACCAGCCGCTCC
TTACCAAGTACCAACCATAGGGGTGTATGGCGTGCCAGGATCAGGCAAGTCTGGCATCATTAAAAGCG
CAGTCACCAAAAAAGATCTAGTGGTGAGCGCCAAGAAAGAAAACTGTGCAGAAATTATAAGGGACGTC
AAGAAAATGAAAGGGCTGGACGTCAATGCCAGAACTGTGGACTCAGTGCTCTTGAATGGATGCAAACA
CCCCGTAGAGACCCTGTATATTGACGAAGCTTTTGCTTGTCATGCAGGTACTCTCAGAGCGCTCATAG
CCATTATAAGACCTAAAAAGGCAGTGCTCTGCGGGGATCCCAAACAGTGCGGTTTTTTAACATGATG
TGCCTGAAAGTGCATTTTAACCACGAGATTTGCACACAAGTCTTCCACAAAAGCATCTCTCGCCGTTG
CACTAAATCTGTGACTTCGGTCGTCTCAACCTTGTTTACGACAAAAAAATGAGAACGACGAATCCGA
AAGAGACTAAGATTGTGATTGACACTACCGGCAGTACCAAACCTAAGCAGGACGATCTCATTCTCACT
TGTTTCAGAGGGTGGGTGAAGCAGTTGCAAATAGATTACAAAGGCAACGAAATAATGACGGCAGCTGC
CTCTCAAGGGCTGACCCGTAAAGGTGTGTATGCCGTTCGGTACAAGGTGAATGAAAATCCTCTGTACG
CACCCACCTCAGAACATGTGAACGTCCTACTGACCCGCACGGAGGACCGCATCGTGTGGAAAACACTA
GCCGGCGACCCATGGATAAAAACACTGACTGCCAAGTACCCTGGGAATTTCACTGCCACGATAGAGGA
GTGGCAAGCAGAGCATGATGCCATCATGAGGCACATCTTGGAGAGACCGGACCCTACCGACGTCTTCC
AGAATAAGGCAAACGTGTGTTGGGCCAAGGCTTTAGTGCCGGTGCTGAAGACCGCTGGCATAGACATG
ACCACTGAACAATGGAACACTGTGGATTATTTTGAAACGGACAAAGCTCACTCAGCAGAGATAGTATT
GAACCAACTATGCGTGAGGTTCTTTGGACTCGATCTGGACTCCGGTCTATTTTCTGCACCCACTGTTC
CGTTATCCATTAGGAATAATCACTGGGATAACTCCCCGTCGCCTAACATGTACGGGCTGAATAAAGAA
GTGGTCCGTCAGCTCTCTCGCAGGTACCCACAACTGCCTCGGGCAGTTGCCACTGGAAGAGTCTATGA
CATGAACACTGGTACACTGCGCAATTATGA

FIG. 7A(contd.)

```
TCCGCGCATAAACCTAGTACCTGTAAACAGAAGACTGCCTCATGCTTTAGTCCTCCACCATAATGAAC
ACCCACAGAGTGACTTTTCTTCATTCGTCAGCAAATTGAAGGGCAGAACTGTCCTGGTGGTCGGGGAA
AAGTTGTCCGTCCCAGGCAAAATGGTTGACTGGTTGTCAGACCGGCCTGAGGCTACCTTCAGAGCTCG
GCTGGATTTAGGCATCCCAGGTGATGTGCCCAAATATGACATAATATTTGTTAATGTGAGGACCCCAT
ATAAATACCATCACTATCAGCAGTGTGAAGACCATGCCATTAAGCTTAGCATGTTGACCAAGAAAGCT
TGTCTGCATCTGAATCCCGGCGGAACCTGTGTCAGCATAGGTTATGGTTACGCTGACAGGGCCAGCGA
AAGCATCATTGGTGCTATAGCGCGGCAGTTCAAGTTTTCCCGGGTATGCAAACCGAAATCCTCACTTG
AAGAGACGGAAGTTCTGTTTGTATTCATTGGGTACGATCGCAAGGCCCGTACGCACAATCCTTACAAG
CTTTCATCAACCTTGACCAACATTTATACAGGTTCCAGACTCCACGAAGCCGGATGTGCACCCTCATA
TCATGTGGTGCGAGGGGATATTGCCACGGCCACCGAAGGAGTGATTATAAATGCTGCTAACAGCAAAG
GACAACCTGGCGGAGGGGTGTGCGGAGCGCTGTATAAGAAATTCCCGGAAAGCTTCGATTTACAGCCG
ATCGAAGTAGGAAAAGCGCGACTGGTCAAAGGTGCAGCTAAACATATCATTCATGCCGTAGGACCAAA
CTTCAACAAAGTTTCGGAGGTTGAAGGTGACAAACAGTTGGCAGAGGCTTATGAGTCCATCGCTAAGA
TTGTCAACGATAACAATTACAAGTCAGTAGCGATTCCACTGTTGTCCACCGGCATCTTTTCCGGGAAC
AAAGATCGACTAACCCAATCATTGAACCATTTGCTGACAGCTTTAGACACCACTGATGCAGATGTAGC
CATATACTGCAGGGACAAGAAATGGGAAATGACTCTCAAGGAAGCAGTGGCTAGGAGAGAAGCAGTGG
AGGAGATATGCATATCCGACGACTCTTCAGTGACAGAACCTGATGCAGAGCTGGTGAGGGTGCATCCG
AAGAGTTCTTTGGCTGGAAGGAAGGGCTACAGCACAAGCGATGGCAAAACTTTCTCATATTTGGAAGG
GACCAAGTTTCACCAGGCGGCCAAGGATATAGCAGAAATTAATGCCATGTGGCCCGTTGCAACGGAGG
CCAATGAGCAGGTATGCATGTATATCCTCGGAGAAAGCATGAGCAGTATTAGGTCGAAATGCCCCGTC
GAAGAGTCGGAAGCCTCCACACCACCTAGCACGCTGCCTTGCTTGTGCATCCATGCCATGACTCCAGA
AAGAGTACAGCGCCTAAAAGCCTCACGTCCAGAACAAATTACTGTGTGCTCATCCTTTCCATTGCCGA
AGTATAGAATCACTGGTGTGCAGAAGATCCAATGCTCCCAGCCTATATTGTTCTCACCGAAAGTGCCT
GCGTATATTCATCCAAGGAAGTATCTCGTGGAAACACCACCGGTAGACGAGACTCCGGAGCCATCGGC
AGAGAACCAATCCACAGAGGGGACACCTGAACAACCACCACTTATAACCGAGGATGAGACCAGGACTA
GAACGCCTGAGCCGATCATCATCGAAGAGGAAGAAGAGGATAGCATAAGTTTGCTGTCAGATGGCCCG
ACCCACCAGGTGCTGCAAGTCGAGGCAGACATTCACGGGCCGCCCTCTGTATCTAGCTCATCCTGGTC
CATTCCTCATGCATCCGACTTTGATGTGGACAGTTTATCCATACTTGACACCCTGGAGGGAGCTAGCG
TGACCAGCGGGCAACGTCAGCCGAGACTAACTCTTACTTCGCAAAGAGTATGGAGTTTCTGGCGCGA
CCGGTGCCTGCGCCTCGAACAGTATTCAGGAACCCTCCACATCCCGCTCCGCGCACAAGAACACCGTC
ACTTGCACCCAGCAGGGCCTGCTCGAGAACCAGCCTAGTTTCCACCCCGCCAGGCGTGAATAGGGTGA
TCACTAGAGAGGAGCTCGAGGCGCTTACCCCGTCACGCACTCCTAGCAGGTCGGTCTCGAGAACCAGC
CTGGTCTCCAACCCGCCAGGCGTAAATAGGGTGATTACAAGAGAGGAGTTTGAGGCGTTCGTAGCACA
ACAACAATGACGGTTTGATGCGGGTGCATACATCTTTTCCTCCGACACCGGTCAAGGGCATTTACAAC
AAAAATCAGTAAGGCAAACGGTGCTATCCGAAGTGGTGTTGGAGAGGACCGAATTGGAGATTTCGTAT
GCCCCGCGCCTCGACCAAGAAAAAGAAGAATTACTACGCAAGAAATTACAGTTAAATCCCACACCTGC
TAACAGAAGCAGATACCAGTCCAGGAAGGTGGAGAACATGAAAGCCATAACAGCTAGACGTATTCTGC
AAGGCCTAGGGCATTATTTGAAGGCAGAAGGAAAAGTGGAGTGCTACCGAACCCTGCATCCTGTTCCT
TTGTATTCATCTAGTGTGAACCGTGCCTTTTCAAGCCCCAAGGTCGCAGTGGAAGCCTGTAACGCCAT
GTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTGCCCTGCAAAGCTGCGCAGCTTTCCA
AAGAAACACTCCTATTTGGAACCCACAATACGATCGGCAGTGCCTTCAGCGATCCAGAACACGCTCCA
GAACGTCCTGGCAGCTGCCACAAAAGAAATTGCAATGTCACGCAAATGAGAGAATTGCCCGTATTGG
ATTCGGCGGCCTTTAATGTGGAATGCTTCAAGAAATATGCGTGTAATAATGAATATTGGGAAACGTTT
AAAGAAAACCCCATCAGGCTTACTGAAGAAAACGTGGTAAATTACATTACCAAATTAAAAGGACCAAA
AGCTGCTGCTCTTTTTGCGAAGACACATAATTTGAATATGTTGCAGGACATACCAATGGACAGGTTTG
TAATGGACTTAAAGAGAGACGTGAAAGTGACTCCAGGAACAAAACATACTGAAGAACGGCCCAAGGTA
CAGGTGATCCAGGCTGCCGATCCGCTAGCAACAGCGTATCTGTGCGGAATCCACCGAGAGCTGGTTAG
GAGATTAAATGCGGTCCTGCTTCCGAACATTCATACACTGTTTGATATGTCGGCTGAAGACTTTGACG
CTATTATAGCCGAGCACTTCCAGCCTGGGGATTGTGTTCTGGAAACTGACATCGCGTCGTTTGATAAA
AGTGAGGACGACGCCATGGCTCTGACCGCG
```

FIG. 7A(contd.)

```
TTAATGATTCTGGAAGACTTAGGTGTGGACGCAGAGCTGTTGACGCTGATTGAGGCGGCTTTCGGCGA
AATTTCATCAATACATTTGCCCACTAAAACTAAATTTAAATTCGGAGCCATGATGAAATCTGGAATGT
TCCTCACACTGTTTGTGAACACAGTCATTAACATTGTAATCGCAAGCAGAGTGTTGAGAGAACGGCTA
ACCGGATCACCATGTGCAGCATTCATTGGAGATGACAATATCGTGAAAGGAGTCAAATCGGACAAATT
AATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCA
GACCCCCTAAAAAGGCTGTTTAAGCTTGGCAAACCTCTGGCAGCAGACGATGAACATGATGATGACAG
GAGAAGGGCATTGCATGAAGAGTCAACACGCTGGAACCGAGTGGGTATTCTTTCAGAGCTGTGCAAGG
CAGTAGAATCAAGGTATGAAACCGTAGGAACTTCCATCATAGTTATGGCCATGACTACTCTAGCTAGC
AGTGTTAAATCATTCAGCTACCTGAGAGGGCCCCTATAACTCTCTACGGCTAACCTGAATGGACTAC
GACATAGTCTAGTCGACGCCACCATGGAACTGCTGATCCTGAAGGCCAACGCCCATCACCACCATCCTG
ACCGCCGTGACCTTCTGCTTCGCCAGCGGCCAGAACATCACCGAGGAATTCTACCAGAGCACCTGCAG
CGCCGTGAGCAAGGGCTACCTGAGCGCCCTGCGGACCGGCTGGTACACCAGCGTGATCACCATCGAGC
TGTCCAACATCAAAGAAAACAAGTGCAACGGCACCGACGCCAAGGTGAAACTGATCAAGCAGGAACTG
GACAAGTACAAGAACGCCGTGACCGAGCTGCAGCTGCTGATGCAGAGCACCCCGCCAACAACCC
GGCCAGAAGAGAGCTGCCCCGGTTCATGAACTACACCCTGAACAACGCCAAGAAAAACAACGTGACCC
TGAGCAAGAAGCGGAAGCGGCGGTTCCTGGGCTTCCTGCTGGGCGTGGGCAGCGCCATCGCCAGCGGC
GTGGCCGTGTCCAAGGTGCTGCACCTGGAAGGCGAGGTGAACAAGATCAAGTCCGCCCTGCTGTCCAC
CAACAAGGCCGTGGTGTCCCTGAGCAACGGCGTGAGCGTGCTGACCAGCAAGGTGCTGGATCTGAAGA
ACTACATCGACAAGCAGCTGCTGCCCATCGTGAACAAGCAGAGCTGCAGCATCAGCAACATCGAGACC
GTGATCGAGTTCCAGCAGAAGAACAACCGGCTGCTGGAAATCACCCGGGAGTTCAGCGTGAACGCCGG
CGTGACCACCCCCGTGAGCACCTACATGCTGACCAACAGCGAGCTGCTGTCCCTGATCAATGACATGC
CCATCACCAACGACCAGAAAAGCTGATGAGCAACAACGTGCAGATCGTGCGGCAGCAGAGCTACTCC
ATCATGAGCATCATCAAAGAAGAGGTGCTGGCCTACGTGGTGCAGCTGCCCCTGTACGCCGTGATCGA
CACCCCCTGCTGGAAGCTGCACACCAGCCCCCTGTGCACCACCAACACCAAAGAGGGCAGCAACATCT
GCCTGACCCGGACCGACCGGGGCTGGTACTGCGACAACGCCGGCAGCGTGAGCTTCTTCCCCCAAGCC
GAGACCTGCAAGGTGCAGAGCAACCGGGTGTTCTGCGACACCATGAACAGCCTGACCCTGCCCTCCGA
GGTGAACCTGTGCAACGTGGACATCTTCAACCCCAAGTACGACTGCAAGATCATGACCTCCAAGACCG
ACGTGAGCAGCTCCGTGATCACCTCCCTGGGCGCCATCGTGAGCTGCTACGGCAAGACCAAGTGCACC
GCCAGCAACAAGAACCGGGGCATCATCAAGACCTTCAGCAACGGCTGCGACTACGTGAGCAACAAGGG
CGTGGACACCGTGAGCGTGGGCAACACACTGTACTACGTGAATAAGCAGGAAGGCAAGAGCCTGTACC
TGAAGGGCGAGCCCATCATCAACTTCTACGACCCCCTGGTGTTCCCCAGCGACGAGTTCGACGCCAGC
ATCAGCCAGGTCAACGAGAAGATCAACCAGAGCCTGGCCTTCATCCGGAAGAGCGACGAGCTGCTGCA
CAATGTGAATGCCGGCAAGAGCACCACCAATATCATGATCACCACAATCATCATCGTGATCATTGTGA
TCCTGCTGTCTCTGATTGCCGTGGGCCTGCTGCTGTACTGCAAGGCCCGCAGCACCCCTGTGACCCTG
TCCAAGGACCAGCTGTCCGGCATCAACAATATCGCCTTCTCCAACTGA AGTCTAGACGGCGCGCCCAC
CCAGCGGCCGCATACAGCAGCAATTGGCAAGCTGCTTACATAGAACTCGCGGCGATTGGCATGCCGCC
TTAAAATTTTTATTTTATTTTTCTTTTCTTTTCCGAATCGGATTTTGTTTTTAATATTTCAAAAAAAA
AAAAAAAAAAAAAAAAAAAAAAAAAAAGGGTCGGCATGGCATCTCCACCTCCTCGCGGTCCGACCTGG
GCATCCGAAGGAGGACGCACGTCCACTCGGATGGCTAAGGGAGAGCCACGTTTAAACCAGCTCCAATT
CGCCCTATAGTGAGTCGTATTACGCGCGCTCACTGGCCGTCGTTTTACAACGTCGTGACTGGGAAAAC
CCTGGCGTTACCCAACTTAATCGCCTTGCAGCACATCCCCCTTTCGCCAGCTGGCGTAATAGCGAAGA
GGCCCGCACCGATCGCCCTTCCCAACAGTTGCGCAGCCTGAATGGCGAATGGGACGCGCCCTGTAGCG
GCGCATTAAGCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAGCTCTAAA
TCGGGGGCTCCCTTTAGGGTTCCGATTTAGTGCTTTACGGCACCTCGACCCCAAAAAACTTGATTAGG
GTGATGGTTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGTCTATTCTTTTGA
TTTATAAGGGATTTTGCCGATTTCGGCCTATTGGTTAAAAAATGAGCTGATTTAACAAAAATTTAACG
CGAATTTTAACAAAATATTAACGCTTACAATTTAGGTGGCACTTTTCGGGGAAATGTGCGCGGAACCC
CTATTTGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGCTGAAGATC
```

```
AGTTGGGTGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATCCCGTAT
TGACGCCGGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCATAACCATG
AGTGATAACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGAGCGTGGGTCTC
GCGGTATCATTGCAGCACTGGGGCCAGATGGTAAGCCCTCCCGTATCGTAGTTATCTACACGACGGGG
AGTCAGGCAACTATGGATGAACGAAATAGACAGATCGCTGAGATAGGTGCCTCACTGATTAAGCATTG
GTAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTTCTTCTAGTGTAGCCGTAG
TTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGG
CGCAGCGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCTTTGAGTGAGCTG
ATACCGCTCGCCGCAGCCGAACGACCGAGCGCAGCGAGTCAGTGAGCGAGGAAGCGGAAGAGCGCCCA
ATACGCAAACCGCCTCTCCCCGCGCGTTGGCCGATTCATTAATGCAGCTGGCACGACAGGTTTCCCGA
CTGGAAAGCGGGCAGTGAGCGCAACGCAATTAATGTGAGTTAGCTCACTCATTAGGCACCCCAGGCTT
TACACTTTATGCTCCCGGCTCGTATGTTGTGTGGAATTGTGAGCGGATAACAATTTCACACAGGAAAC
AGCTATGACCATGATTACGCCAAGCGCGCAATTAACCCTCACTAAAGGGAACAAAAGCTGGGTACCGG
GCCCACGCGTAATACGACTCACTATAG
```

ATAGGCGGCGCATGAGAGAAGCCCAGACCAATTACCTACCCAAAATGGAGAAAGTTCACGTTGACATC
GAGGAAGACAGCCCATTCCTCAGAGCTTTGCAGCGGAGCTTCCCGCAGTTTGAGGTAGAAGCCAAGCA
GGTCACTGATAATGACCATGCTAATGCCAGAGCGTTTTCGCATCTGGCTTCAAAACTGATCGAAACGG
AGGTGGACCCATCCGACACGATCCTTGACATTGGAAGTGCGCCCGCCCGCAGAATGTATTCTAAGCAC
AAGTATCATTGTATCTGTCCGATGAGATGTGCGGAAGATCCGGACAGATTGTATAAGTATGCAACTAA
GCTGAAGAAAAACTGTAAGGAAATAACTGATAAGGAATTGGACAAGAAAATGAAGGAGCTCGCCGCCG
TCATGAGCGACCCTGACCTGGAAACTGAGACTATGTGCCTCCACGACGACGAGTCGTGTCGCTACGAA
GGGCAAGTCGCTGTTTACCAGGATGTATACGCGGTTGACGGACCGACAAGTCTCTATCACCAAGCCAA
TAAGGGAGTTAGAGTCGCCTACTGGATAGGCTTTGACACCACCCCTTTTATGTTTAAGAACTTGGCTG
GAGCATATCCATCATACTCTACCAACTGGGCCGACGAAACCGTGTTAACGGCTCGTAACATAGGCCTA
TGCAGCTCTGACGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTTACTGAGGAGCT
GGCACCTGCCGTCTGTATTTCACTTACGTGGCAAGCAAAATTACACATGTCGGTGTGAGACTATAGTT
AGTTGCGACGGGTACGTCGTTAAAAGAATAGCTATCAGTCCAGGCCTGTATGGGAAGCCTTCAGGCTA
TGCTGCTACGATGCACCGCGAGGGATTCTTGTGCTGCAAAGTGACAGACACATTGAACGGGGAGAGGG
TCTCTTTTCCCGTGTGCACGTATGTGCCAGCTACATTGTGTGACCAAATGACTGGCATACTGGCAACA
GATGTCAGTGCGGACGACGCGCAAAAACTGCTGGTTGGGCTCAACCAGCGTATAGTCGTCAACGGTCG
CACCCAGAGAAACACCAATACCATGAAAAATTACCTTTTGCCCGTAGTGGCCCAGGCATTTGCTAGGT
GGGCAAAGGAATATAAGGAAGATCAAGAAGATGAAAGGCCACTAGGACTACGAGATAGACAGTTAGTC
ATGGGGTGTTGTTGGGCTTTTAGAAGGCACAAGATAACATCTATTTATAAGCGCCCGGATACCCAAAC
CATCATCAAAGTGAACAGCGATTTCCACTCATTCGTGCTGCCCAGGATAGGCAGTAACACATTGGAGA
TCGGGCTGAGAACAAGAATCAGGAAAATGTTAGAGGAGCACAAGGAGCCGTCACCTCTCATTACCGCC
GAGGACGTACAAGAAGCTAAGTGCGCAGCCGATGAGGCTAAGGAGGTGCGTGAAGCCGAGGAGTTGCG
CGCAGCTCTACCACCTTTGGCAGCTGATGTTGAGGAGCCCACTCTGGAAGCCGATGTAGACTTGATGT
TACAAGAGGCTGGGGCCGGCTCAGTGGAGACACCTCGTGGCTTGATAAAGGTTACCAGCTACGATGGC
GAGGACAAGATCGGCTCTTACGCTGTGCTTTCTCCGCAGGCTGTACTCAAGAGTGAAAAATTATCTTG
CATCCACCCTCTCGCTGAACAAGTCATAGTGATAACACACTCTGGCCGAAAAGGGCGTTATGCCGTGG
AACCATACCATGGTAAAGTAGTGGTGCCAGAGGGACATGCAATACCCGTCCAGGACTTTCAAGCTCTG
AGTGAAAGTGCCACCATTGTGTACAACGAACGTGAGTTCGTAAACAGGTACCTGCACCATATTGCCAC
ACATGGAGGAGCGCTGAACACTGATGAAGAATATTACAAAACTGTCAAGCCCAGCGAGCACGACGGCG
AATACCTGTACGACATCGACAGGAAACAGTGCGTCAAGAAAGAACTAGTCACTGGGCTAGGGCTCACA
GGCGAGCTGGTGGATCCTCCCTTCCATGAATTCGCCTACGAGAGTCTGAGAACACGACCAGCCGCTCC
TTACCAAGTACCAACCATAGGGGTGTATGGCGTGCCAGGATCAGGCAAGTCTGGCATCATTAAAAGCG
CAGTCACCAAAAAAGATCTAGTGGTGAGCGCCAAGAAAGAAAACTGTGCAGAAATTATAAGGGACGTC
AAGAAAATGAAAGGGCTGGACGTCAATGCCAGAACTGTGGACTCAGTGCTCTTGAATGGATGCAAACA
CCCCGTAGAGACCCTGTATATTGACGAAGCTTTTGCTTGTCATGCAGGTACTCTCAGAGCGCTCATAG
CCATTATAAGACCTAAAAAGGCAGTGCTCTGCGGGGATCCCAAACAGTGCGGTTTTTTAACATGATG
TGCCTGAAAGTGCATTTTAACCACGAGATTTGCACACAAGTCTTCCACAAAAGCATCTCTCGCCGTTG
CACTAAATCTGTGACTTCGGTCGTCTCAACCTTGTTTTACGACAAAAAAATGAGAACGACGAATCCGA
AAGAGACTAAGATTGTGATTGACACTACCGGCAGTACCAAACCTAAGCAGGACGATCTCATTCTCACT
TGTTTCAGAGGGTGGGTGAAGCAGTTGCAAATAGATTACAAAGGCAACGAAATAATGACGGCAGCTGC
CTCTCAAGGGCTGACCCGTAAAGGTGTGTATGCCGTTCGGTACAAGGTGAATGAAAATCCTCTGTACG
CACCCACCTCAGAACATGTGAACGTCCTACTGACCCGCACGGAGGACCGCATCGTGTGGAAAACACTA
GCCGGCGACCCATGGATAAAAACACTGACTGCCAAGTACCCTGGGAATTTCACTGCCACGATAGAGGA
GTGGCAAGCAGAGCATGATGCCATCATGAGGCACATCTTGGAGAGACCGGACCCTACCGACGTCTTCC
AGAATAAGGCAAACGTGTGTTGGGCCAAGGCTTTAGTGCCGGTGCTGAAGACCGCTGGCATAGACATG
ACCACTGAACAATGGAACACTGTGGATTATTTTGAAACGGACAAAGCTCACTCAGCAGAGATAGTATT
GAACCAACTATGCGTGAGGTTCTTTGGACTCGATCTGGACTCCGGTCTATTTTCTGCACCCACTGTTC
CGTTATCCATTAGGAATAATCACTGG

FIG. 7B(contd.)

```
GATAACTCCCCGTCGCCTAACATGTACGGGCTGAATAAAGAAGTGGTCCGTCAGCTCTCTCGCAGGTA
CCCACAACTGCCTCGGGCAGTTGCCACTGGAAGAGTCTATGACATGAACACTGGTACACTGCGCAATT
ATGATCCGCGCATAAACCTAGTACCTGTAAACAGAAGACTGCCTCATGCTTTAGTCCTCCACCATAAT
GAACACCCACAGAGTGACTTTTCTTCATTCGTCAGCAAATTGAAGGGCAGAACTGTCCTGGTGGTCGG
GGAAAAGTTGTCCGTCCCAGGCAAAATGGTTGACTGGTTGTCAGACCGGCCTGAGGCTACCTTCAGAG
CTCGGCTGGATTTAGGCATCCCAGGTGATGTGCCCAAATATGACATAATATTTGTTAATGTGAGGACC
CCATATAAATACCATCACTATCAGCAGTGTGAAGACCATGCCATTAAGCTTAGCATGTTGACCAAGAA
AGCTTGTCTGCATCTGAATCCCGGCGGAACCTGTGTCAGCATAGGTTATGGTTACGCTGACAGGGCCA
GCGAAAGCATCATTGTGCTATAGCGCGGCAGTTCAAGTTTTCCCGGGTATGCAAACCGAAATCCTCA
CTTGAAGAGACGGAAGTTCTGTTTGTATTCATTGGGTACGATCGCAAGGCCCGTACGCACAATCCTTA
CAAGCTTTCATCAACCTTGACCAACATTTATACAGGTTCCAGACTCCACGAAGCCGGATGTGCACCCT
CATATCATGTGGTGCGAGGGGATATTGCCACGGCCACCGAAGGAGTGATTATAAATGCTGCTAACAGC
AAAGGACAACCTGGCGGAGGGGTGTGCGGAGCGCTGTATAAGAAATTCCCGGAAAGCTTCGATTTACA
GCCGATCGAAGTAGGAAAAGCGCGACTGGTCAAAGGTGCAGCTAAACATATCATTCATGCCGTAGGAC
CAAACTTCAACAAAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGCATCTTTTCCGG
GAACAAAGATCGACTAACCCAATCATTGAACCATTTGCTGACAGCTTTAGACACCACTGATGCAGATG
TAGCCATATACTGCAGGGACAAGAAATGGGAAATGACTCTCAAGGAAGCAGTGGCTAGGAGAGAAGCA
GTGGAGGAGATATGCATATCCGACGACTCTTCAGTGACAGAACCTGATGCAGAGCTGGTGAGGGTGCA
TCCGAAGAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTTGCAACG
GAGGCCAATGAGCAGGTATGCATGTATATCCTCGGAGAAAGCATGAGCAGTATTAGGTCGAAATGCCC
CGTCGAAGAGTCGGAAGCCTCCACACCACCTAGCACGCTGCCTTGCTTGTGCATCCATGCCATGACTC
CAGAAAGAGTACAGCGCCTAAAAGCCTCACGTCCAGAACAAATTACTGTGTGCTCATCCTTTCCATTG
CCGAAGTATAGAATCACTGGTGTGCAGAAGATCCAATGCTCCCAGCCTATATTGTTCTCACCGAAAGT
GCCTGCGTATATTCATCCAAGGAAGTATCTCGTGGAAACACCACCGGTAGACGAGACTCCGGAGCCAT
CGGCAGAGAACCAATCCACAGAGGGGACACCTGAACAACCACCACTTATAACCGAGGATGAGACCAGG
ACTAGAACGCCTGAGCCGATCATCATCGAAGAGGAAGAAGAGGATAGCATAAGTTTGCTGTCAGATGG
CCCGACCCACCAGGTGCTGCAAGTCGAGGCAGACATTCACGGGCCGCCCTCTGTATCTAGCTCATCCT
GGTCCATTCCTCATGCATCCGACTTTGATGTGGACAGTTTATCCATACTTGACACCCTGGAGGGAGCT
AGCGTGACCAGCGGGGCAACGTCAGCCGAGACTAACTCTTACTTCGCAAAGAGTATGGAGTTTCTGGC
GCGACCGGTGCCTGCGCCTCGAACAGTATTCAGGAACCCTCCACATCCCGCTCCGCGCACAAGAACAC
CGTCACTTGCACCCAGCAGGGCCTGCTCGAGAACCAGCCTAGTTTCCACCCCGCCAGGCGTGAATAGG
GTGATCACTAGAGAGGAGCTCGAGGCGCTTACCCCGTCACGCACTCCTAGCAGGTCGGTCTCGAGAAC
CAGCCTGGTCTCCAACCCGCCAGGCGTAAATAGGGTGATTACAAGAGAGGAGTTTGAGGCGTTCGTAG
CACAACAACAATGACGGTTTGATGCGGGTGCATACATCTTTTCCTCCGACACCGGTCAAGGGCATTTA
CAACAAAATCAGTAAGGCAAACGGTGCTATCCGAAGTGGTGTTGGAGAGGACCGAATTGGAGATTTC
GTATGCCCCGCGCCTCGACCAAGAAAAAGAAGAATTACTACGCAAGAAATTACAGTTAAATCCCACAC
CTGCTAACAGAAGCAGATACCAGTCCAGGAAGGTGGAGAACATGAAAGCCATAACAGCTAGACGTATT
CTGCAAGGCCTAGGGCATTATTGAAGGCAGAAGGAAAAGTGGAGTGCTACCGAACCCTGCATCCTGT
TCCTTTGTATTCATCTAGTGTGAACCGTGCCTTTTCAAGCCCCAAGGTCGCAGTGGAAGCCTGTAACG
CCATGTTGAAAGAGAACTTTCCGACTGTGGCTTCTTACTGTATTATTCCAGAGTACGATGCCTATTTG
GACATGGTTGACGGAGCTTCATGCTGCTTAGACACTGCCAGTTTTGCCCTGCAAAGCTGCGCAGCTT
TCCAAAGAAACACTCCTATTTGGAACCCACAATACGATCGGCAGTGCCTTCAGCGATCCAGAACACGC
TCCAGAACGTCCTGGCAGCTGCCACAAAAAGAAATTGCAATGTCACGCAAATGAGAGAATTGCCCGTA
TTGGATTCGGCGGCCTTTAATGTGGAATGCTTCAAGAAATATGCGTGTAATAATGAATATTGGGAAAC
GTTTAAAGAAAACCCCATCAGGCTTACTGAAGAAAACGTGGTAAATTACATTACCAAATTAAAAGGAC
CAAAAGCTGCTGCTCTTTTTGCGAAGACACATAATTTGAATATGTTGCAGGACATACCAATGGACAGG
TTTGTAATGGACTTAAAGAGAGACGTGAAAGTGACTCCAGGAACAAAACATACTGAAGAACGGCCCAA
GGTACAGGTGATCCAGGCTGCCGATCCGCTAGCAACAGCGTATCTGTGCGGAATCCACCGAGAGCTGG
TTAGGAGATTAAATGCGGTCCTGCTTCCGA
```

FIG. 7B(contd.)

```
ACATTCATACACTGTTTGATATGTCGGCTGAAGACTTTGACGCTATTATAGCCGAGCACTTCCAGCCT
GGGGATTGTGTTCTGGAAACTGACATCGCGTCGTTTGATAAAAGTGAGGACGACGCCATGGCTCTGAC
CGCGTTAATGATTCTGGAAGACTTAGGTGTGGACGCAGAGCTGTTGACGCTGATTGAGGCGGCTTTCG
GCGAAATTTCATCAATACATTTGCCCACTAAAACTAAATTTAAATTCGGAGCCATGATGAAATCTGGA
ATGTTCCTCACACTGTTTGTGAACACAGTCATTAACATTGTAATCGCAAGCAGAGTGTTGAGAGAACG
GCTAACCGGATCACCATGTGCAGCATTCATTGGAGATGACAATATCGTGAAAGGAGTCAAATCGGACA
AATTAATGGCAGACAGGTGCGCCACCTGGTTGAATATGGAAGTCAAGATTATAGATGCTGTGGTGGGC
GAGAAAGCGCCTTATTTCTGTGGAGGGTTTATTTTGTGTGACTCCGTGACCGGCACAGCGTGCCGTGT
GGCAGACCCCCTAAAAAGGCTGTTTAAGCTTGGCAAACCTCTGGCAGCAGACGATGAACATGATGATG
ACAGGAGAAGGGCATTGCATGAAGAGTCAACACGCTGGAACCGAGTGGGTATTCTTTCAGAGCTGTGC
AAGGCAGTAGAATCAAGGTATGAAACCGTAGGAACTTCCATCATAGTTATGGCCATGACTACTCTAGC
TAGCAGTGTTAAATCATTCAGCTACCTGAGAGGGCCCCTATAACTCTCTACGGCTAACCTGAATGGA
CTACGACATAGTCTAGTCGACGCCACCATGCTGCTGCTGCTGCTGCTGGGCCTGAGGCTACAGCT
CTCCCTGGCCATCATCCCAGTTGAGGAGGAGAACCCGGACTTCTGGAACCGCGAGGCAGCCGAGGCCC
TGGGTGCCGCCAAGAAGCTGCAGCCTGCACAGACAGCCGCCAAGAACCTCATCATCTTCCTGGGCGAT
GGGATGGGGGTGTCTACGGTGACAGCTGCCAGGATCCTAAAAGGGCAGAAGAAGGACAAACTGGGGCC
TGAGATACCCCTGGCCATGGACCGCTTCCCATATGTGGCTCTGTCCAAGACATACAATGTAGACAAAC
ATGTGCCAGACAGTGGAGCCACAGCCACGGCCTACCTGTGCGGGGTCAAGGGCAACTTCCAGACCATT
GGCTTGAGTGCAGCCGCCCGCTTTAACCAGTGCAACACGACACGCGGCAACGAGGTCATCTCCGTGAT
GAATCGGGCCAAGAAAGCAGGGAAGTCAGTGGGAGTGGTAACCACCACGAGTGCAGCACGCCTCGC
CAGCCGGCACCTACGCCCACACGGTGAACCGCAACTGGTACTCGGACGCCGACGTGCCTGCCTCGGCC
CGCCAGGAGGGGTGCCAGGACATCGCTACGCAGCTCATCTCCAACATGGACATTGACGTGATCCTAGG
TGGAGGCCGAAAGTACATGTTTCGCATGGGAACCCCAGACCCTGAGTACCCAGATGACTACAGCCAAG
GTGGGACCAGGCTGGACGGGAAGAATCTGGTGCAGGAATGGCTGGCGAAGCGCCAGGGTGCCCGGTAT
GTGTGGAACCGCACTGAGCTCATGCAGGCTTCCCTGGACCCGTCTGTGACCCATCTCATGGGTCTCTT
TGAGCCTGGAGACATGAAATACGAGATCCACCGAGACTCCACACTGGACCCCTCCCTGATGGAGATGA
CAGAGGCTGCCCTGCGCCTGCTGAGCAGGAACCCCCGCGGCTTCTTCCTCTTCGTGGAGGGTGGTCGC
ATCGACCATGGTCATCATGAAAGCAGGGCTTACCGGGCACTGACTGAGACGATCATGTTCGACGACGC
CATTGAGAGGCGGGCCAGCTCACCAGCGAGGAGGACACGCTGAGCCTCGTCACTGCCGACCACTCCC
ACGTCTTCTCCTTCGGAGGCTACCCCCTGCGAGGGAGCTCCATCTTCGGGCTGGCCCCTGGCAAGGCC
CGGGACAGGAAGGCCTACACGGTCCTCCTATACGGAAACGGTCCAGGCTATGTGCTCAAGGACGGCGC
CCGGCCGGATGTTACCGAGAGCGAGAGCGGGAGCCCCGAGTATCGGCAGCAGTCAGCAGTGCCCCTGG
ACGAAGAGACCCACGCAGGCGAGGACGTGGCGGTGTTCGCGCGCGGCCCGCAGGCGCACCTGGTTCAC
GGCGTGCAGGAGCAGACCTTCATAGCCGCACGTCATCGCCTTCGCCGCCTGCCTGGAGCCCTACACCGC
CTGCGACCTGGCGCCCCCGCCGGCACCACCGACCGCGCGCACCCGCGTTACTCTAGAGTCGGGGCC
CGGCCCCGTTCCAGCCAGACATGAACTAGACGGCGCGCCCACCCAGCGGCCGCATACAGCAGCAATTGG
CAAGCTGCTTACATAGAACTCGCGGCGATTGGCATGCCGCCTTAAAAATTTTTATTTTATTTTTCTTTT
CTTTTCCGAATCGGATTTTGTTTTTAATATTTCAAAAAAAAAAAAAAAAAAAAAAAAAAAAAAAAAAA
AAAAGGGTCGGCATGGCATCTCCACCTCCTCGCGGTCCGACCTGGGCATCCGAAGGAGGACGCACGT
CCACTCGGATGGCTAAGGGAGAGCCACGTTTAAACCAGCTCCAATTCGCCCTATAGTGAGTCGTATTA
CGCGCGCTCACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATCGCCCTTCC
CAACAGTTGCGCAGCCTGAATGGCGAATGGGACGCGCCCTGTAGCGGCGCATTAAGCGCGGCGGGTGT
GGTGGTTACGCGCAGCGTGACCGCTACACTTGCCAGCGCCCTAGCGCCCGCTCCTTTCGCTTTCTTCC
CTTCCTTTCTCGCCACGTTCGCCGGCTTTCCCCGTCAAGCTCTAAATCGGGGGCTCCCTTTAGGGTTC
CGATTTAGTGCTTTACGGCACCTCGACCCCAAAAAACTTGATTAGGGTGATGGTTCACGTAGTGGGCC
ATCGCCCTGATAGACGGTTTTTCGCCCTTTGACGTTGGAGTCCACGTTCTTTAATAGTGGACTCTTGT
TCCAAACTGGAACAACACTCAACCCTATCTCGGTCTATTCTTTTGATTTATAAGGGATTTTGCCGATT
TCGGCCTATTGGTTAAAAAATGAGCTGATTTAACAAAAATTTAACGCGAATTTTAACAAAATATTAAC
GCTTACAATTTAGGTGGCACTTTTCGGGGAAATGTGCGCGGAACCCCTATTTGTTTATTTTTCTAAAT
ACATTCAAATATGTATCCGCTCATGAGACA
```

```
ATAACCCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGAAAGTA
AAAGATGCTGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCTATGTGGCG
CGGTATTATCCCGTATTGACGCCGGGCAAGAGCAACTCGGTCGCCGCATACACTATTCTCAGAATGAC
TTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGAGCTG
AATGAAGCCATACCAAACGACGAGCGTGACACCACGATGCCTGTAGCAATGGCAACAACGTTGCGCAA
ACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCGTATCGTAGT
TATCTACACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGCTTGGAGCG
AACGACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTACGGTTCCTGGCCT
TTTGCTGGCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATTCATTAATGCAGCTGGC
ACGACAGGTTTCCCGACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGTGAGCGGATAACA
ATTTCACACAGGAAACAGCTATGACCATGATTACGCCAAGCGCGCAATTAACCCTCACTAAAGGGAAC
AAAAGCTGGGTACCGGGCCCACGCGTAATACGACTCACTATAG
```

```
gcagtcaccaaaaaagatctagtggtgagcgccaagaaagaaaactgtgcagaaattataag
ggacgtcaagaaaatgaaagggctggacgtcaatgccagaactgtggactcagtgctcttga
atggatgcaaacaccccgtagagaccctgtatattgacgaagcttttgcttgtcatgcaggt
actctcagagcgctcatagccattataagacctaaaaaggcagtgctctgcggggatcccaa
acagtgcggttttttaacatgatgtgcctgaaagtgcattttaaccacgagatttgcacac
aagtcttccacaaaagcatctctcgccgttgcactaaatctgtgacttcggtcgtctcaacc
ttgttttacgacaaaaaaatgagaacgacgaatccgaagagactaagattgtgattgacac
taccggcagtaccaaacctaagcaggacgatctcattctcacttgtttcagagggtgggtga
agcagttgcaaatagattacaaaggcaacgaaataatgacggcagctgcctctcaagggctg
acccgtaaaggtgtgtatgccgttcggtacaaggtgaatgaaaatcctctgtacgcacccac
ctcagaacatgtgaacgtcctactgaccgcacggaggaccgcatcgtgtggaaaacactag
ccggcgacccatggataaaaacactgactgccaagtaccctgggaatttcactgccacgata
gaggagtggcaagcagagcatgatgccatcatgaggcacatcttggagagaccggaccctac
cgacgtcttccagaataaggcaaacgtgtgttgggccaaggctttagtgccggtgctgaaga
ccgctggcatagacatgaccactgaacaatggaacactgtggattattttgaaacggacaaa
gctcactcagcagagatagtattgaaccaactatgcgtgaggttctttggactcgatctgga
ctccggtctatttctgcacccactgttccgttatccattaggaataatcactgggataact
ccccgtcgcctaacatgtacgggctgaataaagaagtggtccgtcagctctctcgcaggtac
ccacaactgcctcgggcagttgccactggaagagtctatgacatgaacactggtacactgcg
caattatgatccgcgcataaacctagtacctgtaaacagaagactgcctcatgctttagtcc
tccaccataatgaacacccacagagtgacttttcttcattcgtcagcaaattgaagggcaga
actgtcctggtggtcggggaaaagttgtccgtcccaggcaaaatggttgactggttgtcaga
ccggcctgaggctaccttcagagctcggctggatttaggcatcccaggtgatgtgcccaaat
atgacataatatttgttaatgtgaggacccatataaataccatcactatcagcagtgtgaa
gaccatgccattaagcttagcatgttgaccaagaaagcttgtctgcatctgaatcccggcgg
aacctgtgtcagcataggttatggttacgctgacagggccagcgaaagcatcattggtgcta
tagcgcggcagttcaagttttcccgggtatgcaaaccgaaatcctcacttgaagagacggaa
gttctgtttgtattcattgggtacgatcgcaaggcccgtacgcacaatccttacaagctttc
atcaaccttgaccaacatttatacaggttccagactccacgaagccggatgtgcaccctcat
atcatgtggtgcgaggggatattgccacggccaccgaaggagtgattataaatgctgctaac
agcaaaggacaacctggcggagggtgtgcggagcgctgtataagaaattcccggaaagctt
cgatttacagccgatcgaagtaggaaaagcgcgactggtcaaggtgcagctaaacatatca
ttcatgccgtaggaccaaacttcaacaaagtttcggaggttgaaggtgacaaacagttggca
gaggcttatgagtccatcgctaagattgtcaacgataacaattacaagtcagtagcgattcc
actgttgtccaccggcatcttttccgggaacaaagatcgactaacccaatcattgaaccatt
tgctgacagctttagacaccactgatgcagatgtagccatatactgcagggacaagaaatgg
gaaatgactctcaaggaagcagtggctaggagagaagcagtggaggagatatgcatatccga
cgactcttcagtgacagaacctgatgcagagctggtgaggtgcatccgaagagttctttgg
ctggaaggaagggctacagcacaagcgatggcaaaactttctcatatttggaagggaccaag
tttcaccaggcggccaaggatatagcagaaattaatgccatgtggcccgttgcaacggaggc
caatgagcaggtatgcatgtatatcctcggagaaagcatgagcagtattaggtcgaaatgcc
ccgtcgaagagtcggaagcctccacaccacctagcacgctgccttgcttgtgcatccatgcc
atgactccagaaagagtacagcgcctaaaagcctcacgtccagaacaaattactgtgtgctc
atcctttccattgccgaagtatagaatcactggtgtgcagaagatccaatgctcccagccta
tattgttctcaccgaaagtgcctg
```

FIG. 7C(contd.)

cgtatattcatccaaggaagtatctcgtggaaacaccaccggtagacgagactccggagcca
tggcagagaaccaatccacagaggggacacctgaacaaccaccacttataaccgaggatga
gaccaggactagaacgcctgagccgatcatcatcgaagaggaagaagaggatagcataagtt
tgctgtcagatggcccgacccaccaggtgctgcaagtcgaggcagacattcacgggccgccc
tctgtatctagctcatcctggtccattcctcatgcatccgactttgatgtggacagtttatc
catacttgacaccctggagggagctagcgtgaccagcggggcaacgtcagccgagactaact
cttacttcgcaagagtatggagtttctggcgcgaccggtgcctgcgcctcgaacagtattc
aggaaccctccacatcccgctccgcgcacaagaacaccgtcacttgcacccagcagggcctg
ctcgagaaccagcctagttccaccccgccaggcgtgaatagggtgatcactagagaggagc
tcgaggcgcttacccgtcacgcactcctagcaggtcggtctcgagaaccagcctggtctcc
aacccgccaggcgtaaatagggtgattacaagagaggagtttgaggcgttcgtagcacaaca
acaatgacggtttgatgcgggtgcatacatcttttcctccgacaccggtcaagggcatttac
aacaaaaatcagtaaggcaaacggtgctatccgaagtggtgttggagaggaccgaattggag
atttcgtatgccccgcgcctcgaccaagaaaaagaagaattactacgcaagaaattacagtt
aaatcccacacctgctaacagaagcagataccagtccaggaaggtggagaacatgaaagcca
taacagctagacgtattctgcaaggcctagggcattatttgaaggcagaaggaaaagtggag
tgctaccgaaccctgcatcctgttcctttgtattcatctagtgtgaaccgtgccttttcaag
ccccaaggtcgcagtggaagcctgtaacgccatgttgaaagagaactttccgactgtggctt
cttactgtattattccagagtacgatgcctatttggacatggttgacggagcttcatgctgc
ttagacactgccagttttgccctgcaaagctgcgcagctttccaaagaaacactcctattt
ggaacccacaatacgatcggcagtgccttcagcgatccagaacacgctccagaacgtcctgg
cagctgccacaaaaagaaattgcaatgtcacgcaaatgagagaattgcccgtattggattcg
gcggcctttaatgtggaatgcttcaagaaatatgcgtgtaataatgaatattgggaaacgtt
taaagaaaaccccatcaggcttactgaagaaaacgtggtaaattacattaccaaattaaaag
gaccaaaagctgctgctctttttgcgaagacacataatttgaatatgttgcaggacatacca
atggacaggtttgtaatggacttaaagagagacgtgaaagtgactccaggaacaaaacatac
tgaagaacggcccaaggtacaggtgatccaggctgccgatccgctagcaacagcgtatctgt
gcggaatccaccgagagctggttaggagattaaatgcggtcctgcttccgaacattcataca
ctgtttgatatgtcggctgaagactttgacgctattatagccgagcacttccagcctgggga
ttgtgttctggaaactgacatcgcgtcgtttgataaagtgaggacgacgccatggctctga
ccgcgttaatgattctggaagacttaggtgtggacgcagagctgttgacgctgattgaggcg
gctttcggcgaaatttcatcaatacatttgcccactaaaactaaatttaaattcggagccat
gatgaaatctggaatgttcctcacactgtttgtgaacacagtcattaacattgtaatcgcaa
gcagagtgttgagagaacggctaaccggatcaccatgtgcagcattcattggagatgacaat
atcgtgaaaggagtcaaatcggacaaattaatggcagacaggtgcgccacctggttgaatat
ggaagtcaagattatagatgctgtggtgggcgagaaagcgccttatttctgtggaggttta
ttttgtgtgactccgtgaccggcacagcgtgccgtgtggcagacccctaaaaaggctgttt
aagcttggcaaacctctggcagcagacgatgaacatgatgatgacaggagaagggcattgca
tgaagagtcaacacgctggaaccgagtgggtattctttcagagctgtgcaaggcagtagaat
caaggtatgaaaccgtaggaacttccatcatagttatggccatgactactctagctagcagt
gttaaatcattcagctacctgagagggcccctataactctctacggctaacctgaatggac
tacgacatagtctagtcgacgccacc<mark>atggaactgctgatcctgaaggcaacgccatcacc
accatcctgaccgccgtgac</mark>

FIG. 7C(contd.)

```
ttctgcttcgccagcggccagaacatcaccgaggaattctaccagagcacctgcagcgccg
tgagcaagggctacctgagcgccctgcggaccggctggtacaccagcgtgatcaccatcgag
ctgtccaacatcaaagaaaacaagtgcaacggcaccgacgccaaggtgaaactgatcaagca
ggaactggacaagtacaagaacgccgtgaccgagctgcagctgctgatgcagagcacccccg
ccaccaacaaccggggccagaagagagctgccccggttcatgaactacaccctgaacaacgcc
aagaaaccaacgtgaccctgagcaagaagcggaagcggcggagcgccatcgccagcgggt
ggccgtgtccaaggtgctgcacctggaaggcgaggtgaacaagatcaagtccgccctgctgt
ccaccaacaaggccgtggtgtccctgagcaacggcgtgagcgtgctgaccagcaaggtgctg
atctgaagaactacatcgacaagcagctgctgcccatcgtgaacaagcagagctgcagcat
cagcaacatcgagaccgtgatcgagttccagcagaagaacaaccggctgctggaaatcaccc
gggagttcagcgtgaacgccggcgtgaccaccccgtgagcacctacatgctgaccaacagc
gagctgctgtccctgatcaatgacatgcccatcaccaacgaccagaaaagctgatgagcaa
caacgtgcagatcgtgcggcagcagagctactccatcatgagcatcatcaagaagaggtgc
tggcctacgtggtgcagctgcccctgtacggcgtgatcgacaccccctgctggaagctgcac
accagcccctgtgcaccaccaacaccaaagagggcagcaacatctgcctgaccggaccga
ccggggctggtactgcgacaacgccggcagcgtgagcttcttccccaagccgagacctgca
aggtgcagagcaaccgggtgttctgcgacaccatgaacagcctgaccctgccctccgaggtg
aacctgtgcaacgtggacatcttcaaccccaagtacgactgcaagatcatgacctccaagac
cgacgtgagcagctccgtgatcacctccctgggcgccatcgtgagctgctacggcaagacca
agtgcaccgccagcaacaagaaccggggcatcatcaagaccttcagcaacggctgcgactac
gtgagcaacaagggcgtggacaccgtgagcgtgggcaacacactgtactacgtgaataagca
ggaaggcaagagcctgtacgtgaagggcgagcccatcatcaacttctacgacccctggtgt
tccccagcgacgagttcgacgccagcatcagccaggtcaacgagaagatcaaccagagcctg
gccttcatccggaagtccgacgagctgctgcacaatgtgaatgccggcaagagcaccaccaa
tatcatgatcaccacaatcatcatcgtgatcattgtgatcctgctgtctctgattgccgtgg
gctgctgctgtactgcaaggcccgcagcacccctgtgaccctgtccaaggaccagctgtcc
ggcatcaacaatatcgccttctccaactga
```
gtctagacggcgcgccacccagcggccgca
tacagcagcaattggcaagctgcttacatagaactcgcggcgattggcatgccgccttaaaa
ttttatttattttctttcttttccgaatcggattttgtttttaatatttcaaaaaaaa
aaaaaaaaaaaaaaaaaaaaaaaaaaaaagaagagcgtttaaacacgtgatatctggcc
tcatgggccttcctttcactgccgctttccagtcgggaaacctgtcgtgccagctgcatta
acatggtcatagctgtttccttgcgtattgggcgctctccgcttcctcgctcactgactcgc
tgcgctcggtcgttcgggtaaagcctggggtgcctaatgagcaaaaggccagcaaaaggcca
ggaaccgtaaaaaggccgcgttgctggcgttttccataggctccgcccccctgacgagcat
cacaaaaatcgacgctcaagtcagaggtggcgaaacccgacaggactataaagataccaggc
gtttccccctggaagctccctcgtgcgctctcctgttccgaccctgccgcttaccggatacc
tgtccgcctttctcccttcgggaagcgtggcgctttctcatagctcacgctgtaggtatctc
agttcggtgtaggtcgttcgctccaagctgggctgtgtgcacgaacccccgttcagcccga
ccgctgcgccttatccggtaactatcgtcttgagtccaacccggtaagacacgacttatcgc
cactggcagcagccactggtaacaggattagcagagcgaggtatgtaggcggtgctacagag
ttcttgaagtggtggcctaactacggctacactagaagaacagtatttggtatctgcgctct
gctgaagccagttaccttcggaaaaagagttggtagctcttgatccggcaaacaaaccaccg
ctggtagcggtggtttttttgtttgcaagcagcagattacgcgcagaaaaaaggatctcaa
gaagatcctttgatcttttctacggggtctgacgctcagtggaacgaaaactcacgttaagg
gattttggtcatgaatacacggtg

FIG. 7C(contd.)

cctgactgcgttagcaatttaactgtgataaactaccgcattaaagcttatcgatgataagc
tgtcaaacatgagaattcttagaaaaactcatcgagcatcaaatgaaactgcaatttattca
tatcaggattatcaataccatattttttgaaaaagccgtttctgtaatgaaggagaaaactca
ccgaggcagttccataggatggcaagatcctggtatcggtctgcgattccgactcgtccaac
atcaatacaacctattaatttcccctcgtcaaaaataaggttatcaagtgagaaatcaccat
gagtgacgactgaatccggtgagaatggcaaaagcttatgcatttctttccagacttgttca
acaggccagccattacgctcgtcatcaaaatcactcgcatcaaccaaaccgttattcattcg
tgattgcgcctgagcgagacgaaatacgcgatcgctgttaaaaggacaattacaaacaggaa
tcgaatgcaaccggcgcaggaacactgccagcgcatcaacaatatttttcacctgaatcagga
tattcttctaatacctggaatgctgttttcccggggatcgcagtggtgagtaaccatgcatc
atcaggagtacggataaaatgcttgatggtcggaagaggcataaattccgtcagccagttta
gtctgaccatctcatctgtaacatcattggcaacgctacctttgccatgtttcagaaacaac
tctggcgcatcgggcttcccatacaatcgatagattgtcgcacctgattgcccgacattatc
gcgagcccatttatacccatataaatcagcatccatgttggaatttaatcgcggcctcgagc
aagacgtttcccgttgaatatggctcataacacccccttgtattactgtttatgtaagcagac
agttttattgttcatgagcggatacatatttgaatgtatttagaaaaataaacaaatagggg
ttccgcgcacatttccccgaaaagtgccacctaaattgtaagcgttaatatttttgttaaaat
tcgcgttaaattttttgttaaatcagctcattttttaaccaataggccgaaatcggcaaaatc
ccttataaatcaaaagaatagaccgagatagggttgagtggccgctacagggcgctcccatt
cgccattcaggctgcgcaactgttgggaagggcgtttcggtgcgggcctcttcgctattacg
ccagctggcgaaaggggggatgtgctgcaaggcgattaagttgggtaacgccagggttttccc
agtcacacgcgtaatacgactcactatagataggcggcgcatgagagaagcccagaccaatt
acctacccaaaatggagaaagttcacgttgacatcgaggaagacagcccattcctcagagct
ttgcagcggagcttcccgcagtttgaggtagaagccaagcaggtcactgataatgaccatgc
taatgccagagcgttttcgcatctggcttcaaaactgatcgaaacggaggtggacccatccg
acacgatccttgacattggaagtgcgcccgcccgcagaatgtattctaagcacaagtatcat
tgtatctgtccgatgagatgtgcggaagatccggacagattgtataagtatgcaactaagct
gaagaaaaactgtaaggaaataactgataaggaattggacaagaaaatgaaggagctcgccg
ccgtcatgagcgaccctgacctggaaactgagactatgtgcctccacgacgacgagtcgtgt
cgctacgaagggcaagtcgctgtttaccaggatgtatacgcggttgacggaccgacaagtct
ctatcaccaagccaataagggagttagagtcgcctactggataggctttgacaccacccctt
ttatgtttaagaacttggctggagcatatccatcatactctaccaactgggccgacgaaacc
gtgttaacggctcgtaacataggcctatgcagctctgacgttatggagcggtcacgtagagg
gatgtccattcttagaaagaagtatttgaaaccatccaacaatgttctattctctgttggct
cgaccatctaccacgagaagagggacttactgaggagctggcacctgccgtctgtatttcac
ttacgtggcaagcaaaattacacatgtcggtgtgagactatagttagttgcgacgggtacgt
cgttaaaagaatagctatcagtccaggcctgtatgggaagccttcaggctatgctgctacga
tgcaccgcgagggattcttgtgctgcaaagtgacagacacattgaacggggagagggtctct
tttcccgtgtgcacgtatgtgccagctacattgtgtgaccaaatgactggcatactggcaac
agatgtcagtgcggacgacgcgcaaaaactgctggttgggctcaaccagcgtatagtcgtca
acggtcgcacccagagaaacaccaataccatgaaaaattaccttttgcccgtagtggcccag
gcatttgctaggtgggcaaaggaatataaggaagatcaagaagatgaaaggccactaggact
acgagatagacagttagtcatggggtgttgttgggcttttagaaggcacaagataacatcta
tttataagcgcccggatacccaaaccatcatcaaagtgaacagcgatttccactcattcgtg
ctgcccaggataggcagtaacaca

```
ttggagatcgggctgagaacaagaatcaggaaaatgttagaggagcacaaggagccgtcacc
tctcattaccgccgaggacgtacaagaagctaagtgcgcagccgatgaggctaaggaggtgc
gtgaagccgaggagttgcgcgcagctctaccacctttggcagctgatgttgaggagcccact
ctggaagccgatgtagacttgatgttacaagaggctggggccggctcagtggagacacctcg
tggcttgataaaggttaccagctacgatggcgaggacaagatcggctcttacgctgtgcttt
ctccgcaggctgtactcaagagtgaaaaattatcttgcatccaccctctcgctgaacaagtc
atagtgataacacactctggccgaaaagggcgttatgccgtggaaccataccatggtaaagt
agtggtgccagagggacatgcaatacccgtccaggactttcaagctctgagtgaaagtgcca
ccattgtgtacaacgaacgtgagttcgtaaacaggtacctgcaccatattgccacacatgga
ggagcgctgaacactgatgaagaatattacaaaactgtcaagcccagcgagcacgacggcga
atacctgtacgacatcgacaggaaacagtgcgtcaagaaagaactagtcactgggctagggc
tcacaggcgagctggtggatcctcccttccatgaattcgcctacgagagtctgagaacacga
ccagccgctccttaccaagtaccaaccataggggtgtatggcgtgccaggatcaggcaagtc
tggcatcattaaaagc
```

FIG. 7C(contd.)

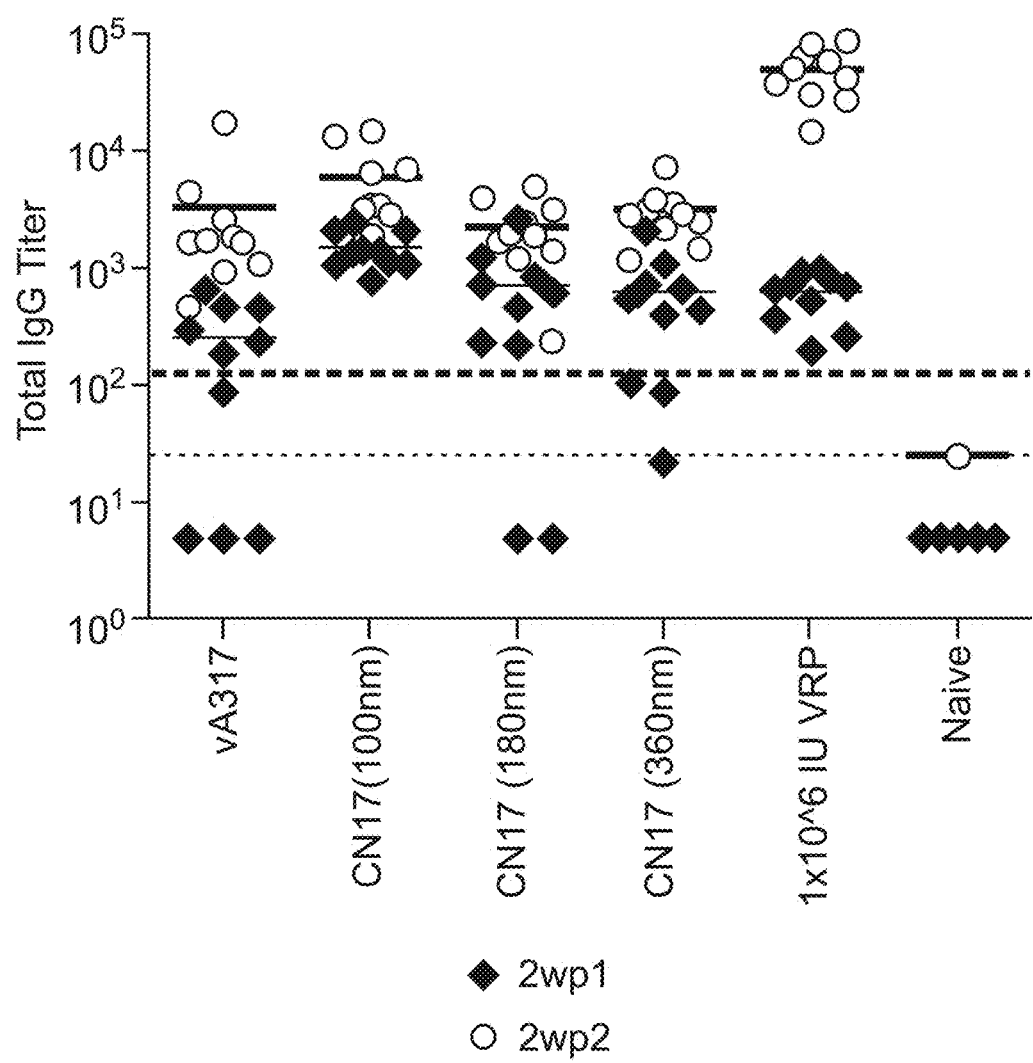

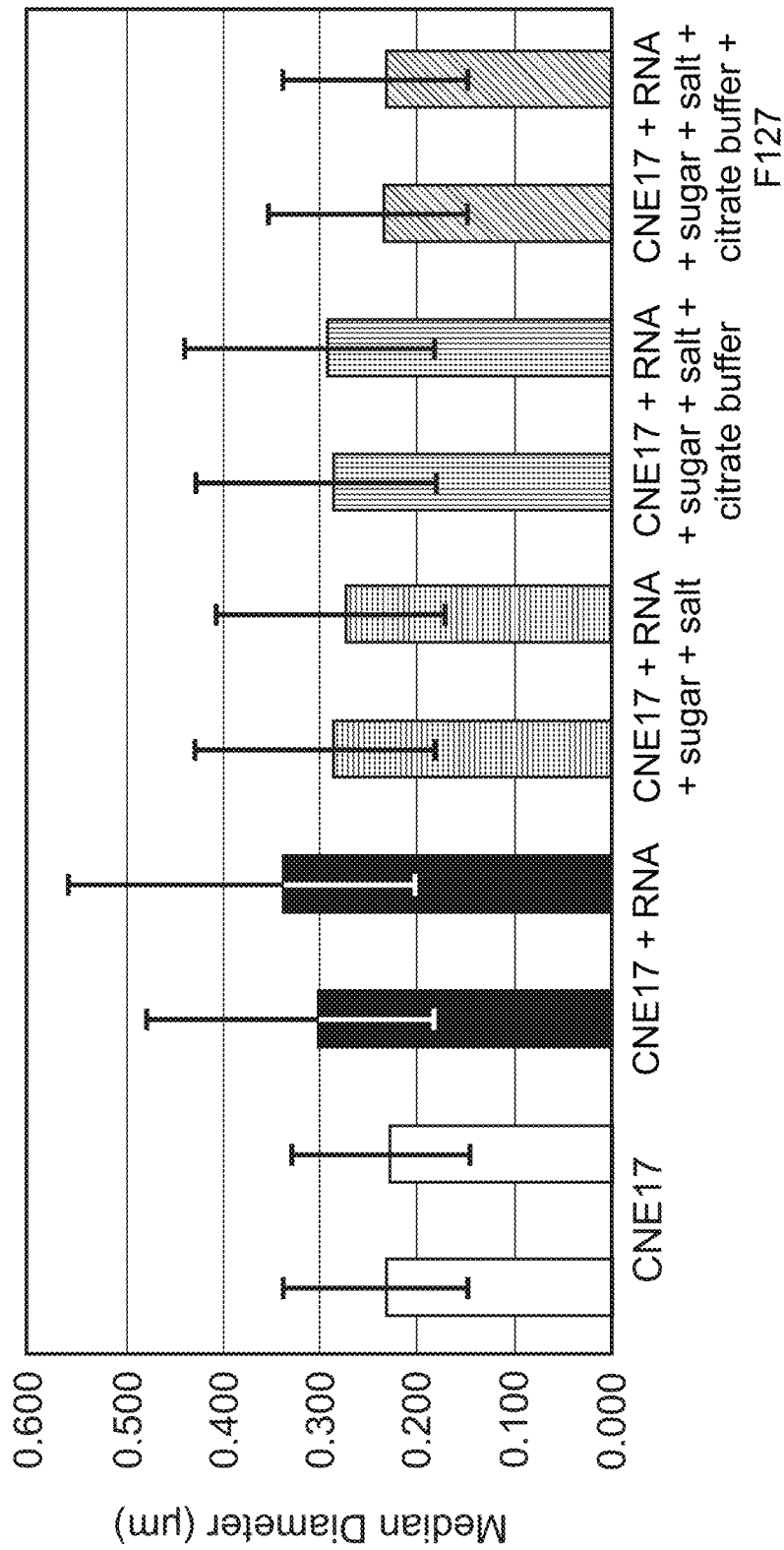

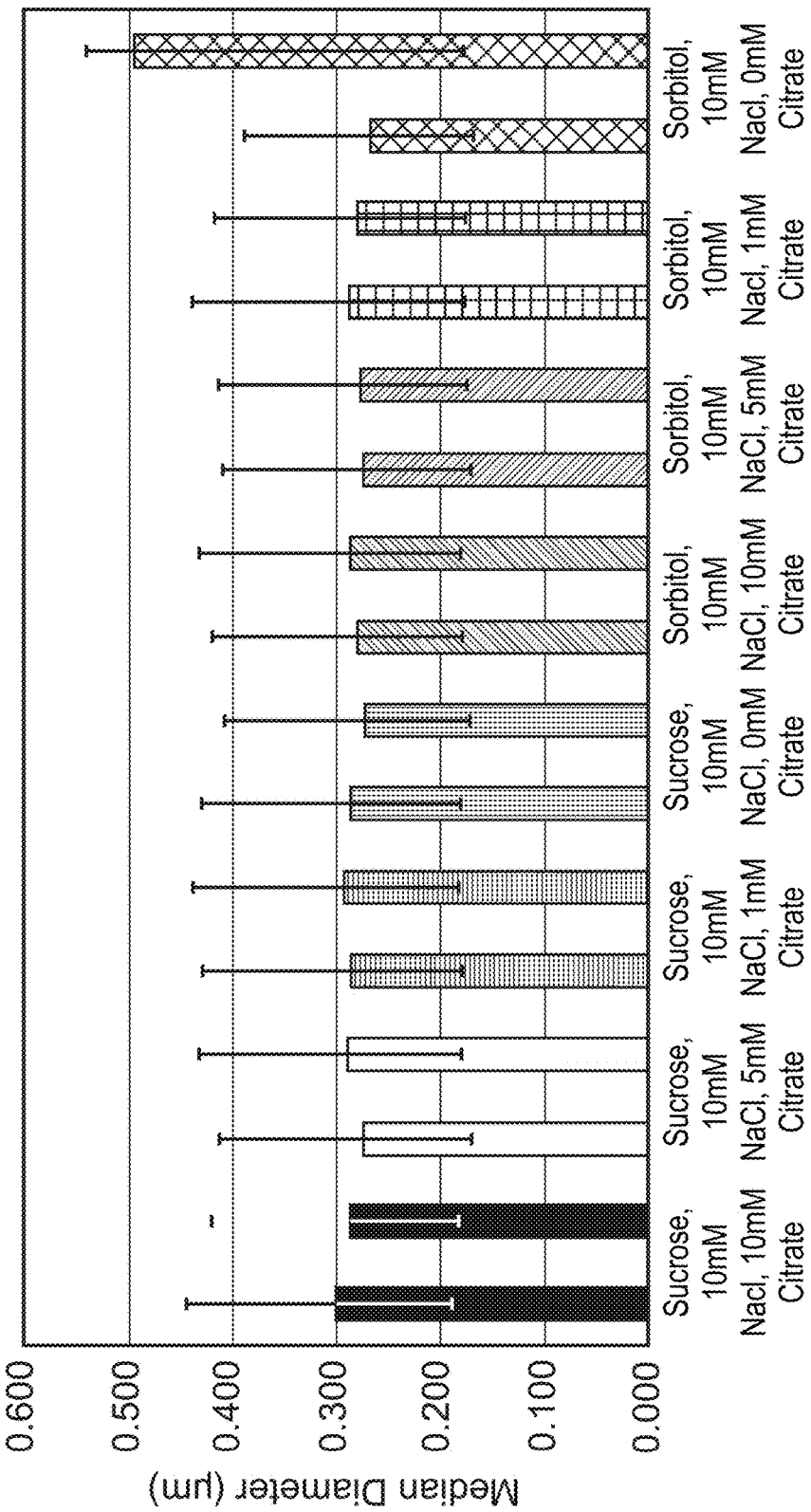

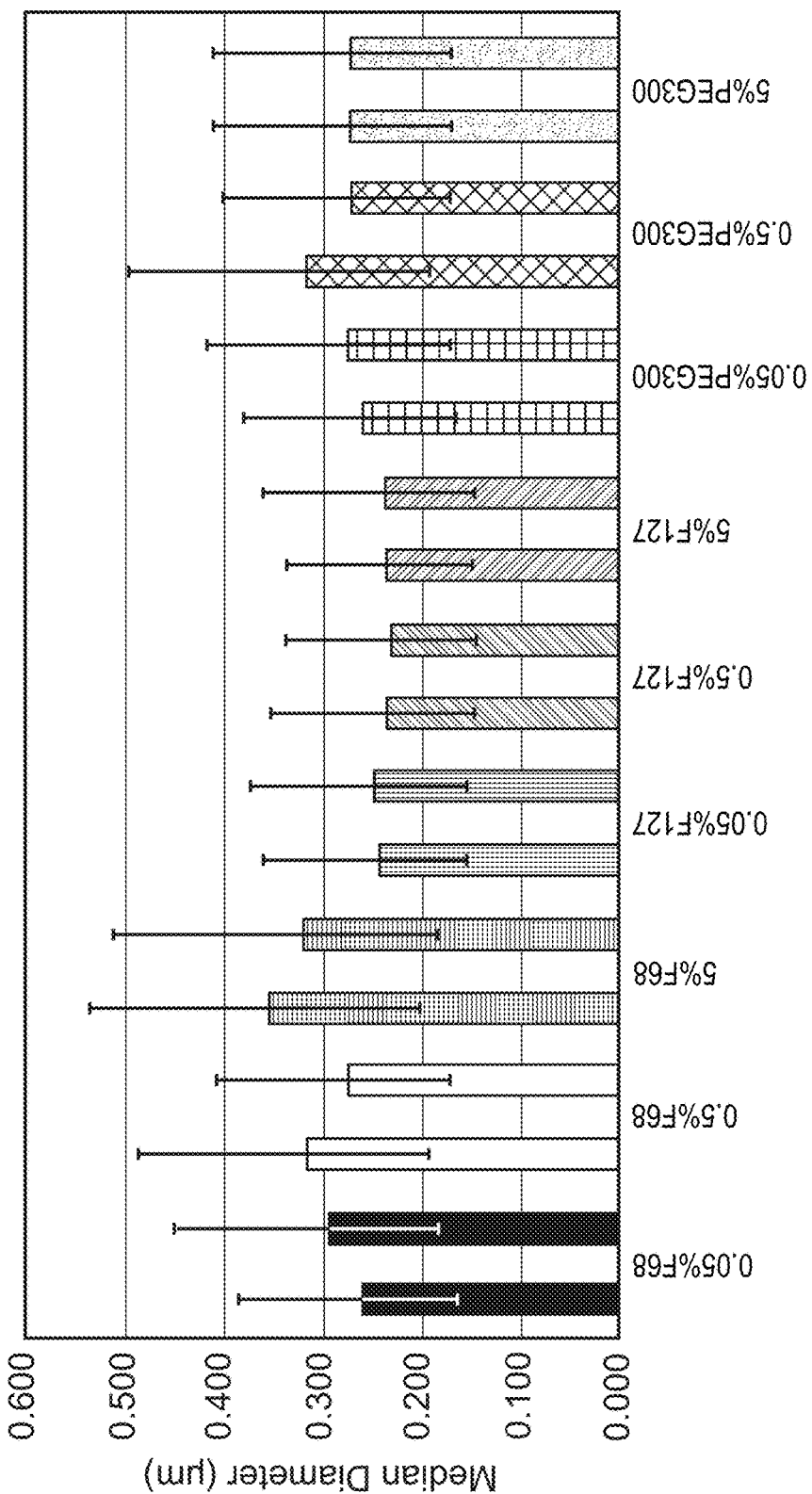

SEQUENCE LISTING

<160> NUMBER OF SEQ ID NOS: 3

<210> SEQ ID NO 1
<211> LENGTH: 12463
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1
ataggcggcg catgagagaa gcccagacca attacctacc caaaatggag aaagttcacg    60

-continued

```
ttgacatcga ggaagacagc ccattcctca gagctttgca gcggagcttc ccgcagtttg        120
aggtagaagc caagcaggtc actgataatg accatgctaa tgccagagcg ttttcgcatc        180
tggcttcaaa actgatcgaa acggaggtgg acccatccga cacgatcctt gacattggaa        240
gtgcgcccgc ccgcagaatg tattctaagc acaagtatca ttgtatctgt ccgatgagat        300
gtgcggaaga tccggacaga ttgtataagt atgcaactaa gctgaagaaa aactgtaagg        360
aaataactga taaggaattg gacaagaaaa tgaaggagct cgccgccgtc atgagcgacc        420
ctgacctgga aactgagact atgtgcctcc acgacgacga gtcgtgtcgc tacgaagggc        480
aagtcgctgt ttaccaggat gtatacgcgg ttgacggacc gacaagtctc tatcaccaag        540
ccaataaggg agttagagtc gcctactgga taggctttga caccacccct tttatgttta        600
agaacttggc tggagcatat ccatcatact ctaccaactg ggccgacgaa accgtgttaa        660
cggctcgtaa cataggccta tgcagctctg acgttatgga gcggtcacgt agagggatgt        720
ccattcttag aaagaagtat ttgaaaccat ccaacaatgt tctattctct gttggctcga        780
ccatctacca cgagaagagg gacttactga ggagctggca cctgccgtct gtatttcact        840
tacgtggcaa gcaaaattac acatgtcggt gtgagactat agttagttgc gacgggtacg        900
tcgttaaaag aatagctatc agtccaggcc tgtatgggaa gccttcaggc tatgctgcta        960
cgatgcaccg cgagggattc ttgtgctgca aagtgacaga cacattgaac ggggagaggg       1020 tctctttttcc cgtgtgcacg tatgtgccag ctacattgtg tgaccaaatg actggcatac       1080
tggcaacaga tgtcagtgcg gacgacgcgc aaaaactgct ggttgggctc aaccagcgta       1140
tagtcgtcaa cggtcgcacc cagagaaaca ccaataccat gaaaaattac cttttgcccg       1200
tagtggccca ggcatttgct aggtgggcaa aggaatataa ggaagatcaa gaagatgaaa       1260
ggccactagg actacgagat agacagttag tcatggggtg ttgttgggct tttagaaggc       1320
acaagataac atctatttat aagcgcccgg atacccaaac catcatcaaa gtgaacagcg       1380
atttccactc attcgtgctg cccaggatag gcagtaacac attggagatc gggctgagaa       1440
caagaatcag gaaaatgtta gaggagcaca aggagccgtc acctctcatt accgccgagg       1500
acgtacaaga agctaagtgc gcagccgatg aggctaagga ggtgcgtgaa gccgaggagt       1560
tgcgcgcagc tctaccacct ttggcagctg atgttgagga gcccactctg gaagccgatg       1620
tagacttgat gttacaagag gctggggccg gctcagtgga gacacctcgt ggcttgataa       1680
aggttaccag ctacgatggc gaggacaaga tcggctctta cgctgtgctt tctccgcagg       1740
ctgtactcaa gagtgaaaaa ttatcttgca tccaccctct cgctgaacaa gtcatagtga       1800
taacacactc tggccgaaaa gggcgttatg ccgtggaacc ataccatggt aaagtagtgg       1860
tgccagaggg acatgcaata cccgtccagg actttcaagc tctgagtgaa agtgccacca       1920
ttgtgtacaa cgaacgtgag ttcgtaaaca ggtacctgca ccatattgcc acacatggag       1980
gagcgctgaa cactgatgaa gaatattaca aaactgtcaa gcccagcgag cacgacggcg       2040
aatacctgta cgacatcgac aggaaacagt gcgtcaagaa agaactagtc actgggctag       2100
ggctcacagg cgagctggtg gatcctcc tt ccatgaatt cgcctacgag agtctgagaa       2160
cacgaccagc cgctccttac caagtaccaa ccataggggt gtatggcgtg ccaggatcag       2220
gcaagtctgg catcattaaa agcgcagtca ccaaaaaaga tctagtggtg agcgccaaga       2280
aagaaaactg tgcagaaatt ataagggacg tcaagaaaat gaaagggctg acgtcaatg        2340 ccagaactgt ggactcagtg ctcttgaatg gatgcaaaca ccccgtagag accctgtata       2400
ttgacgaagc ttttgcttgt catgcaggta ctctcagagc gctcatagcc attataagac       2460
```

```
ctaaaaaggc agtgctctgc ggggatccca aacagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaagg    4080
gagtgattat aaatgctgct aacagcaaag gacaacctgg cggagggtg tgcggagcgc    4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag gctacagca    4620 caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
```

```
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg     5160 aagaagagga tagcataagt tgctgtcag atggcccgac ccaccaggtg ctgcaagtcg     5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagccagtt tccaccccgc     5520 caggcgtgaa tagggtgatc actagagagg agctcgaggc gcttacccg tcacgcactc     5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
```

```
aagcgcctta tttctgtgga gggtttattt tgtgtgactc cgtgaccggc acagcgtgcc   7260
gtgtggcaga cccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgacgcc   7560
accatggaac tgctgatcct gaaggccaac gccatcacca ccatcctgac cgccgtgacc   7620
ttctgcttcg ccagcggcca gaacatcacc gaggaattct accagagcac ctgcagcgcc   7680
gtgagcaagg gctacctgag cgccctgcgg accggctggt acaccagcgt gatcaccatc   7740
gagctgtcca acatcaaaga aaacaagtgc aacggcaccg acgccaaggt gaaactgatc   7800
aagcaggaac tggacaagta caagaacgcc gtgaccgagc tgcagctgct gatgcagagc   7860 accccccgcca ccaacaaccg ggccagaaga gagctgcccc ggttcatgaa ctacaccctg   7920
aacaacgcca gaaaaccaa cgtgaccctg agcaagaagc ggaagcggcg gttcctgggc   7980
ttcctgctgg gcgtgggcag cgccatcgcc agcggggtgg ccgtgtccaa ggtgctgcac   8040
ctggaaggcg aggtgaacaa gatcaagtcc gccctgctgt ccaccaacaa ggccgtggtg   8100
tccctgagca acggcgtgag cgtgctgacc agcaaggtgc tggatctgaa gaactacatc   8160
gacaagcagc tgctgcccat cgtgaacaag cagagctgca gcatcagcaa catcgagacc   8220
gtgatcgagt ccagcagaa gaacaaccgg ctgctggaaa tcaccgggga gttcagcgtg   8280
aacgccggcg tgaccacccc cgtgagcacc tacatgctga ccaacagcga gctgctgtcc   8340
ctgatcaatg acatgcccat caccaacgac cagaaaaagc tgatgagcaa caacgtgcag   8400
atcgtgcggc agcagagcta ctccatcatg agcatcatca agaagaggt gctggcctac   8460 gtggtgcagc tgcccctgta cggcgtgatc gacaccccct gctggaagct gcacaccagc   8520
cccctgtgca ccaccaacac caaagagggc agcaacatct gcctgacccg gaccgaccgg   8580
ggctggtact gcgacaacgc cggcagcgtg agcttcttcc cccaagccga gacctgcaag   8640
gtgcagagca accgggtgtt ctgcgacacc atgaacagct gaccctgcc ctccgaggtg   8700 aacctgtgca acgtggacat cttcaacccc aagtacgact gcaagatcat gacctccaag   8760
accgacgtga gcagctccgt gatcacctcc ctgggcgcca tcgtgagctg ctacggcaag   8820
accaagtgca ccgccagcaa caagaaccgg ggcatcatca gaccttcag caacggctgc   8880 gactacgtga gcaacaaggg cgtggacacc gtgagcgtgg caacacact gtactacgtg   8940 aataagcagg aaggcaagag cctgtacgtg aagggcgagc ccatcatcaa cttctacgac   9000
cccctggtgt tccccagcga cgagttcgac gccagcatca gccaggtcaa cgagaagatc   9060
aaccagagcc tggccttcat ccggaagagc gacgagctgc tgcacaatgt gaatgccggc   9120
aagagcacca ccaatatcat gatcaccaca atcatcatcg tgatcattgt gatcctgctg   9180
tctctgattg ccgtgggcct gctgctgtac tgcaaggccc gcagcacccc tgtgaccctg   9240
tccaaggacc agctgtccgg catcaacaat atcgccttct ccaactgaag tctagacggc   9300
gcgcccaccc agcggccgca tacagcagca attggcaagc tgcttacata gaactcgcgg   9360
cgattggcat gccgccttaa aatttttatt ttatttttct tttcttttcc gaatcggatt   9420 ttgttttaa tatttcaaaa aaaaaaaaaa aaaaaaaaa aaaaaaaaa agggtcggca   9480 tggcatctcc acctcctcgc ggtccgacct gggcatccga aggaggacgc acgtccactc   9540
```

```
ggatggctaa gggagagcca cgtttaaacc agctccaatt cgccctatag tgagtcgtat   9600
tacgcgcgct cactggccgt cgttttacaa cgtcgtgact gggaaaaccc tggcgttacc   9660
caacttaatc gccttgcagc acatccccct ttcgccagct ggcgtaatag cgaagaggcc   9720
cgcaccgatc gcccttccca cagttgcgc agcctgaatg gcgaatggga cgcgccctgt    9780
agcggcgcat taagcgcggc gggtgtggtg gttacgcgca gcgtgaccgc tacacttgcc   9840
agcgccctag cgcccgctcc tttcgctttc ttcccttcct ttctcgccac gttcgccggc   9900
tttccccgtc aagctctaaa tcgggggctc cctttagggt tccgatttag tgctttacgg   9960
cacctcgacc ccaaaaaact tgattagggt gatggttcac gtagtgggcc atcgccctga  10020
tagacggttt ttcgcccttt gacgttggag tccacgttct ttaatagtgg actcttgttc  10080
caaactggaa caacactcaa ccctatctcg gtctattctt ttgatttata agggattttg  10140
ccgatttcgg cctattggtt aaaaaatgag ctgatttaac aaaaatttaa cgcgaatttt  10200
aacaaaatat taacgcttac aatttaggtg cacttttcg gggaaatgtg cgcggaaccc    10260
ctatttgttt attttctaa atacattcaa atatgtatcc gctcatgaga caataaccct    10320
gataaatgct tcaataatat tgaaaaagga agagtatgag tattcaacat ttccgtgtcg   10380
cccttattcc cttttttgcg gcattttgcc ttcctgtttt tgctcaccca gaaacgctgg   10440
tgaaagtaaa agatgctgaa gatcagttgg gtgcacgagt gggttacatc gaactggatc   10500
tcaacagcgg taagatcctt gagagttttc gccccgaaga acgttttcca atgatgagca   10560
cttttaaagt tctgctatgt ggcgcggtat tatcccgtat tgacgccggg caagagcaac   10620
tcggtcgccg catacactat tctcagaatg acttggttga gtactcacca gtcacagaaa   10680
agcatcttac ggatggcatg acagtaagag aattatgcag tgctgccata accatgagtg   10740
ataacactgc ggccaactta cttctgacaa cgatcgagg accgaaggag ctaaccgctt    10800
ttttgcacaa catgggggat catgtaactc gccttgatcg ttgggaaccg gagctgaatg   10860
aagccatacc aaacgacgag cgtgacacca cgatgcctgt agcaatggca acaacgttgc   10920
gcaaactatt aactggcgaa ctacttactc tagcttcccg gcaacaatta atagactgga   10980
tggaggcgga taaagttgca ggaccacttc tgcgctcggc ccttccggct ggctggttta   11040
ttgctgataa atctggagcc ggtgagcgtg ggtctcgcgg tatcattgca gcactggggc   11100
cagatggtaa gccctcccgt atcgtagtta tctacacgac ggggagtcag gcaactatgg   11160
atgaacgaaa tagacagatc gctgagatag gtgcctcact gattaagcat tggtaactgt   11220
cagaccaagt ttactcatat atactttaga ttgatttaaa acttcatttt taatttaaaa   11280
ggatctaggt gaagatcctt tttgataatc tcatgaccaa aatcccttaa cgtgagtttt   11340
cgttccactg agcgtcagac cccgtagaaa agatcaaagg atcttcttga gatccttttt   11400
ttctgcgcgt aatctgctgc ttgcaaacaa aaaaaccacc gctaccagcg gtggtttgtt   11460
tgccggatca agagctacca actctttttc cgaaggtaac tggcttcagc agagcgcaga   11520
taccaaatac tgttcttcta gtgtagccgt agttaggcca ccacttcaag aactctgtag   11580
caccgcctac atacctcgct ctgctaatcc tgttaccagt ggctgctgcc agtggcgata   11640
agtcgtgtct taccgggttg gactcaagac gatagttacc ggataaggcg cagcggtcgg   11700
gctgaacggg gggttcgtgc acacagccca gcttggagcg aacgacctac accgaactga   11760
gatacctaca gcgtgagcta tgagaaagcg ccacgcttcc cgaagggaga aaggcggaca   11820
ggtatccggt aagcggcagg gtcggaacag gagagcgcac gagggagctt ccaggggaa    11880
acgcctggta tctttatagt cctgtcgggt ttcgccacct ctgacttgag cgtcgatttt   11940
```

-continued

```
tgtgatgctc gtcagggggg cggagcctat ggaaaaacgc cagcaacgcg gccttttac     12000 ggttcctggc cttttgctgg cctttgctc acatgttctt tcctgcgtta tccctgatt      12060 ctgtggataa ccgtattacc gcctttgagt gagctgatac cgctcgccgc agccgaacga   12120
ccgagcgcag cgagtcagtg agcgaggaag cggaagagcg cccaatacgc aaaccgcctc   12180
tccccgcgcg ttggccgatt cattaatgca gctggcacga caggtttccc gactggaaag   12240
cgggcagtga gcgcaacgca attaatgtga gttagctcac tcattaggca ccccaggctt   12300
tacactttat gctcccggct cgtatgttgt gtggaattgt gagcggataa caatttcaca   12360
caggaaacag ctatgaccat gattacgcca agcgcgcaat taaccctcac taaagggaac   12420
aaaagctggg taccgggccc acgcgtaata cgactcacta tag                      12463
```

<210> SEQ ID NO 2
<211> LENGTH: 12301
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccaccct tttatgttta    600 agaacttggc tggagcatat ccatcatact ctaccaactg ggccgacgaa accgtgttaa    660
cggctcgtaa cataggccta tgcagctctg acgttatgga gcggtcacgt agaggatgt     720 ccattcttag aaagaagtat ttgaaaccat ccaacaatgt tctattctct gttggctcga    780
ccatctacca cgaagagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
```

```
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct tggcagctg atgttgagga gcccactctg gaagccgatg     1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct ccatgaatt cgcctacgag agtctgagaa     2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc      2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg      2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc gggaaaagt tgtccgtccc aggcaaaatg gttgactggt     3600
tgtcagaccg gcctgaggct accttcagag ctcggctgga tttaggcatc ccaggtgatg    3660
tgcccaaata tgcataata tttgttaatg tgaggacccc atataaatac catcactatc     3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
```

```
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag     4080 gagtgattat aaatgctgct aacagcaaag acaacctgg cggaggggtg tgcggagcgc     4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttacccg tcacgcactc     5580 ctagcaggtc ggtctcgaga accagcctgg tctccaaccc gccaggcgta ataggggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaagaagaa ttactacgca agaaattaca gttaaatccc acacctgcta     5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
```

```
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta gcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgacgcc    7560
accatgctgc tgctgctgct gctgctgggc ctgaggctac agctctccct gggcatcatc    7620
ccagttgagg aggagaaccc ggacttctgg aaccgcgagg cagccgaggc cctgggtgcc    7680
gccaagaagc tgcagcctgc acagacagcc gccaagaacc tcatcatctt cctgggcgat    7740
gggatggggg tgtctacggt gacagctgcc aggatcctaa aagggcagaa gaaggacaaa    7800
ctggggcctg agataccct ggccatggac cgcttcccat atgtggctct gtccaagaca    7860
tacaatgtag acaaacatgt gccagacagt ggagccacag ccacggccta cctgtgcggg    7920
gtcaagggca acttccagac cattggcttg agtgcagccg cccgctttaa ccagtgcaac    7980
acgacacgcg gcaacgaggt catctccgtg atgaatcggg ccaagaaagc agggaagtca    8040
gtgggagtgg taaccaccac acgagtgcag cacgcctcgc cagccggcac ctacgcccac    8100
acggtgaacc gcaactggta ctcggacgcc gacgtgcctg cctcggcccg ccaggagggg    8160
tgccaggaca tcgctacgca gctcatctcc aacatggaca ttgacgtgat cctaggtgga    8220
ggccgaaagt acatgtttcg catgggaacc ccagaccctg agtacccaga tgactacagc    8280
caaggtggga ccaggctgga cggaagaat ctggtcagg aatggctggc gaagcgccag    8340
ggtgcccggt atgtgtggaa ccgcactgag ctcatgcagg cttccctgga cccgtctgtg    8400
acccatctca tgggtctctt tgagcctgga gacatgaaat acgagatcca ccgagactcc    8460
acactggacc cctccctgat ggagatgaca gaggctgccc tgcgcctgct gagcaggaac    8520
ccccgcggct tcttcctctt cgtggagggt ggtcgcatcg accatggtca tcatgaaagc    8580
```

```
agggcttacc gggcactgac tgagacgatc atgttcgacg acgccattga gagggcgggc   8640
cagctcacca gcgaggagga cacgctgagc ctcgtcactg ccgaccactc ccacgtcttc   8700
tccttcggag gctacccct gcgagggagc tccatcttcg ggctggcccc tggcaaggcc    8760
cgggacagga aggcctacac ggtcctccta tacggaaacg gtccaggcta tgtgctcaag   8820
gacggcgccc ggccggatgt taccgagagc gagagcggga gccccgagta tcggcagcag   8880
tcagcagtgc ccctggacga agagacccac gcaggcgagg acgtggcggt gttcgcgcgc   8940
ggcccgcagg cgcacctggt tcacggcgtg caggagcaga ccttcatagc gcacgtcatg   9000
gccttcgccg cctgcctgga gccctacacc gcctgcgacc tggcgccccc cgccggcacc   9060
accgacgccg cgcacccggg ttactctaga gtcggggcgg ccggccgctt cgagcagaca   9120
tgaactagac ggcgcgccca cccagcggcc gcatacagca gcaattggca agctgcttac   9180
atagaactcg cggcgattgg catgccgcct taaaattttt atttattttt ctttctttt   9240 tccgaatcga attttgtttt taatatttca aaaaaaaaa aaaaaaaaa aaaaaaaaa   9300 aaaaaaaag ggtcggcatg gcatctccac ctcctcgcgg tccgacctgg gcatccgaag    9360
gaggacgcac gtccactcgg atggctaagg gagagccacg tttaaaccag ctccaattcg   9420
ccctatagtg agtcgtatta cgcgcgctca ctggccgtcg ttttacaacg tcgtgactgg   9480
gaaaaccctg gcgttaccca acttaatcgc cttgcagcac atccccttt cgccagctgg    9540 cgtaatagcg aagaggcccg caccgatcgc ccttcccaac agttgcgcag cctgaatggc   9600
gaatgggacg cgccctgtag cggcgcatta agcgcggcgg gtgtggtggt tacgcgcagc   9660
gtgaccgcta cacttgccag cgccctagcg cccgctcctt tcgctttctt cccttcctt    9720 ctcgccacgt tcgccggctt tccccgtcaa gctctaaatc gggggctccc tttagggttc   9780
cgatttagtg ctttacggca cctcgacccc aaaaaacttg attagggtga tggttcacgt   9840
agtgggccat cgccctgata acggttttt cgccctttga cgttggagtc cacgttcttt    9900
aatagtggac tcttgttcca aactggaaca acactcaacc ctatctcggt ctattctttt   9960
gatttataag ggattttgcc gatttcggcc tattggttaa aaatgagct gatttaacaa    10020 aaatttaacg cgaattttaa caaaatatta acgcttacaa tttaggtggc acttttcggg   10080
gaaatgtgcg cggaacccct atttgtttat ttttctaaat acattcaaat atgtatccgc   10140
tcatgagaca ataaccctga taaatgcttc aataatattg aaaaggaag agtatgagta   10200 ttcaacattt ccgtgtcgcc cttattccct tttttgcggc attttgcctt cctgtttttg   10260
ctcacccaga aacgctggtg aaagtaaaag atgctgaaga tcagttgggt gcacgagtgg   10320
gttacatcga actggatctc aacagcggta agatccttga gttttcgc cccgaagaac    10380 gttttccaat gatgagcact tttaaagttc tgctatgtgg cgcggtatta tcccgtattg   10440
acgccgggca agagcaactc ggtcgccgca tacactattc tcagaatgac ttggttgagt   10500
actcaccagt cacagaaaag catcttacgg atggcatgac agtaagagaa ttatgcagtg   10560
ctgccataac catgagtgat aacactgcgg ccaacttact tctgacaacg atcggaggac   10620
cgaaggagct aaccgctttt ttgcacaaca tgggggatca tgtaactcgc cttgatcgtt   10680
gggaaccgga gctgaatgaa gccataccaa acgacgagc tgacaccacg atgcctgtag    10740
caatggcaac aacgttgcgc aaactattaa ctggcgaact acttactcta gcttcccggc   10800
aacaattaat agactggatg gaggcggata aagttgcagg accacttctg cgctcggccc   10860
ttccggctgg ctggtttatt gctgataaat ctggagccgg tgagcgtggg tctcgcggta   10920
```

```
tcattgcagc actggggcca gatggtaagc cctcccgtat cgtagttatc tacacgacgg    10980
ggagtcaggc aactatggat gaacgaaata gacagatcgc tgagataggt gcctcactga    11040
ttaagcattg gtaactgtca gaccaagttt actcatatat actttagatt gatttaaaac    11100
ttcattttta atttaaaagg atctaggtga agatccttt tgataatctc atgaccaaaa    11160
tcccttaacg tgagttttcg ttccactgag cgtcagaccc cgtagaaaag atcaaaggat    11220
cttcttgaga tccttttttt ctgcgcgtaa tctgctgctt gcaaacaaaa aaaccaccgc    11280
taccagcggt ggtttgtttg ccggatcaag agctaccaac tcttttccg aaggtaactg    11340 gcttcagcag agcgcagata ccaaatactg tccttctagt gtagccgtag ttaggccacc    11400
acttcaagaa ctctgtagca ccgcctacat acctcgctct gctaatcctg ttaccagtgg    11460
ctgctgccag tggcgataag tcgtgtctta ccgggttgga ctcaagacga tagttaccgg    11520
ataaggcgca gcggtcgggc tgaacggggg gttcgtgcac acagcccagc ttggagcgaa    11580
cgacctacac cgaactgaga tacctacagc gtgagctatg agaaagcgcc acgcttcccg    11640
aagggagaaa ggcggacagg tatccggtaa gcggcagggt cggaacagga gagcgcacga    11700
gggagcttcc agggggaaac gcctggtatc tttatagtcc tgtcgggttt cgccacctct    11760
gacttgagcg tcgatttttg tgatgctcgt caggggggcg gagcctatgg aaaaacgcca    11820
gcaacgcggc cttttacgg ttcctggcct tttgctggcc ttttgctcac atgttctttc    11880
ctgcgttatc ccctgattct gtggataacc gtattaccgc ctttgagtga gctgataccg    11940
ctcgccgcag ccgaacgacc gagcgcagcg agtcagtgag cgaggaagcg gaagagcgcc    12000
caatacgcaa accgcctctc cccgcgcgtt ggccgattca ttaatgcagc tggcacgaca    12060
ggtttcccga ctggaaagcg ggcagtgagc gcaacgcaat taatgtgagt tagctcactc    12120
attaggcacc ccaggcttta cactttatgc ttccggctcg tatgttgtgt ggaattgtga    12180
gcggataaca atttcacaca ggaaacagct atgaccatga ttacgccaag cgcgcaatta    12240
accctcacta aagggaacaa aagctgggta ccgggcccac gcgtaatacg actcactata    12300
g                                                                    12301
```

<210> SEQ ID NO 3  
<211> LENGTH: 11702  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 3

```
gcagtcacca aaaagatct agtggtgagc gccaagaaag aaaactgtgc agaaattata     60
agggacgtca agaaaatgaa agggctggac gtcaatgcca gaactgtgga ctcagtgctc    120
ttgaatggat gcaaacaccc cgtagagacc ctgtatattg acgaagcttt tgcttgtcat    180
gcaggtactc tcagagcgct catagccatt ataagaccta aaaaggcagt gctctgcggg    240
gatcccaaac agtgcggttt ttttaacatg atgtgcctga agtgcatttt taaccacgag    300
atttgcacac aagtcttcca caaaagcatc tctcgccgtt gcactaaatc tgtgacttcg    360
gtcgtctcaa ccttgtttta cgacaaaaaa atgagaacga cgaatccgaa agagactaag    420
attgtgattg acactaccgg cagtaccaaa cctaagcagg acgatctcat tctcacttgt    480
ttcagagggt gggtgaagca gttgcaaata gattacaaag gcaacgaaat aatgacggca    540
gctgcctctc aagggctgac cgtaaaggt gtgtatgccg ttcggtacaa ggtgaatgaa    600
```

```
aatcctctgt acgcacccac ctcagaacat gtgaacgtcc tactgacccg cacggaggac      660
cgcatcgtgt ggaaaacact agccggcgac ccatggataa aaacactgac tgccaagtac      720
cctgggaatt tcactgccac gatagaggag tggcaagcag agcatgatgc catcatgagg      780
cacatcttgg agagaccgga ccctaccgac gtcttccaga ataaggcaaa cgtgtgttgg      840
gccaaggctt tagtgccggt gctgaagacc gctggcatag acatgaccac tgaacaatgg      900
aacactgtgg attattttga aacgacaaaa gctcactcag cagagatagt attgaaccaa      960
ctatgcgtga ggttctttgg actcgatctg gactccggtc tattttctgc acccactgtt     1020
ccgttatcca ttaggaataa tcactgggat aactccccgt cgcctaacat gtacgggctg     1080
aataaagaag tggtccgtca gctctctcgc aggtacccac aactgcctcg ggcagttgcc     1140
actggaagag tctatgacat gaacactggt acactgcgca attatgatcc gcgcataaac     1200
ctagtacctg taaacagaag actgcctcat gctttagtcc tccaccataa tgaacaccca     1260
cagagtgact tttcttcatt cgtcagcaaa ttgaagggca gaactgtcct ggtggtcggg     1320
gaaaagttgt ccgtcccagg caaaatggtt gactggttgt cagaccggcc tgaggctacc     1380
ttcagagctc ggctggattt aggcatccca ggtgatgtgc ccaaatatga cataatattt     1440
gttaatgtga ggaccccata taaataccat cactatcagc agtgtgaaga ccatgccatt     1500
aagcttagca tgttgaccaa gaaagcttgt ctgcatctga atcccggcgg aacctgtgtc     1560
agcataggtt atggttacgc tgacagggcc agcgaaagca tcattggtgc tatagcgcgg     1620
cagttcaagt tttcccgggt atgcaaaccg aaatcctcac ttgaagagac ggaagttctg     1680
tttgtattca ttgggtacga tcgcaaggcc cgtacgcaca atccttacaa gctttcatca     1740
accttgacca acatttatac aggttccaga ctccacgaag ccggatgtgc accctcatat     1800
catgtggtgc gagggatat tgccacggcc accgaaggag tgattataaa tgctgctaac     1860
agcaaaggac aacctggcgg aggggtgtgc ggagcgctgt ataagaaatt cccggaaagc     1920
ttcgatttac agccgatcga agtaggaaaa gcgcgactgg tcaaaggtgc agctaaacat     1980
atcattcatg ccgtaggacc aaacttcaac aaagtttcgg aggttgaagg tgacaaacag     2040
ttggcagagg cttatgagtc catcgctaag attgtcaacg ataacaatta caagtcagta     2100
gcgattccac tgttgtccac cggcatcttt tccgggaaca agatcgact aacccaatca     2160 ttgaaccatt tgctgacagc tttagacacc actgatgcag atgtagccat atactgcagg     2220
gacaagaaat gggaaatgac tctcaaggaa gcagtggcta ggagagaagc agtggaggag     2280
atatgcatat ccgacgactc ttcagtgaca gaacctgatg cagagctggt gagggtgcat     2340
ccgaagagtt cttggctgg aaggaagggc tacagcacaa gcgatggcaa aactttctca     2400
tatttggaag ggaccaagtt tcaccaggcg gccaaggata tagcagaaat taatgccatg     2460
tggccccgtg caacggaggc caatgagcag gtatgcatgt atatcctcgg agaaagcatg     2520
agcagtatta ggtcgaaatg ccccgtcgaa gagtcggaag cctccacacc acctagcacg     2580
ctgccttgct tgtgcatcca tgccatgact ccagaaagag tacagcgcct aaaagcctca     2640
cgtccagaac aaattactgt gtgctcatcc tttccattgc cgaagtatag aatcactggt     2700
gtgcagaaga tccaatgctc ccagcctata ttgttctcac cgaaagtgcc tgcgtatatt     2760
catccaagga agtatctcgt ggaaacacca ccggtagacg agactccgga gccatcggca     2820
gagaaccaat ccacagaggg gacacctgaa caaccaccac ttataaccga ggatgagacc     2880
aggactagaa cgcctgagcc gatcatcatc gaagaggaag aagaggatag cataagtttg     2940
```

```
ctgtcagatg gcccgaccca ccaggtgctg caagtcgagg cagacattca cgggccgccc    3000
tctgtatcta gctcatcctg gtccattcct catgcatccg actttgatgt ggacagttta    3060
tccatacttg acaccctgga gggagctagc gtgaccagcg gggcaacgtc agccgagact    3120
aactcttact tcgcaaagag tatggagttt ctggcgcgac cggtgcctgc gcctcgaaca    3180
gtattcagga accctccaca tcccgctccg cgcacaagaa caccgtcact tgcacccagc    3240
agggcctgct cgagaaccag cctagttttc accccgccag gcgtgaatag ggtgatcact    3300
agagaggagc tcgaggcgct taccccgtca cgcactccta gcaggtcggt ctcgagaacc    3360
agcctggtct ccaacccgcc aggcgtaaat agggtgatta caagagagga gtttgaggcg    3420
ttcgtagcac aacaacaatg acggtttgat gcgggtgcat acatcttttc ctccgacacc    3480
ggtcaagggc atttacaaca aaaatcagta aggcaaacgg tgctatccga agtggtgttg    3540
gagaggaccg aattggagat tcgtatgcc ccgcgcctcg accaagaaaa agaagaatta    3600
ctacgcaaga aattacagtt aaatcccaca cctgctaaca gaagcagata ccagtccagg    3660
aaggtggaga acatgaaagc cataacagct agacgtattc tgcaaggcct agggcattat    3720
ttgaaggcag aaggaaaagt ggagtgctac cgaaccctgc atcctgttcc tttgtattca    3780
tctagtgtga accgtgcctt tcaagcccc aaggtcgcag tggaagcctg taacgccatg    3840
ttgaaagaga actttccgac tgtggcttct tactgtatta ttccagagta cgatgcctat    3900
ttggacatgg ttgacggagc ttcatgctgc ttagacactg ccagttttg ccctgcaaag    3960
ctgcgcagct ttccaaagaa acactcctat ttggaaccca caatacgatc ggcagtgcct    4020
tcagcgatcc agaacacgct ccagaacgtc tggcagctg ccacaaaaag aaattgcaat    4080
gtcacgcaaa tgagagaatt gcccgtattg gattcggcgg cctttaatgt ggaatgcttc    4140
aagaaatatg cgtgtaataa tgaatattgg gaaacgttta agaaaaccc catcaggctt    4200
actgaagaaa acgtggtaaa ttacattacc aaattaaaag gaccaaaagc tgctgctctt    4260
tttgcgaaga cacataattt gaatatgttg caggacatac caatggacag gtttgtaatg    4320
gacttaaaga gagacgtgaa agtgactcca ggaacaaaac atactgaaga acggcccaag    4380
gtacaggtga tccaggctgc cgatccgcta gcaacagcgt atctgtgcgg aatccaccga    4440
gagctggtta ggagattaaa tgcggtcctg cttccgaaca ttcatacact gtttgatatg    4500
tcggctgaag actttgacgc tattatagcc gagcacttcc agcctgggga ttgtgttctg    4560
gaaactgaca tcgcgtcgtt tgataaaagt gaggacgacg ccatggctct gaccgcgtta    4620
atgattctgg aagacttagg tgtggacgca gagctgttga cgctgattga ggcggctttc    4680
ggcgaaattt catcaataca tttgcccact aaaactaaat ttaaattcgg agccatgatg    4740
aaatctggaa tgttcctcac actgtttgtg aacacagtca ttaacattgt aatcgcaagc    4800
agagtgttga gagaacggct aaccggatca ccatgtgcag cattcattgg agatgacaat    4860
atcgtgaaag gagtcaaatc ggacaaatta atggcagaca ggtgcgccac ctggttgaat    4920
atggaagtca agattataga tgctgtggtg gcgagaaag cgccttattt ctgtggaggg    4980
tttattttgt gtgactccgt gaccggcaca gcgtgccgtg tggcagaccc cctaaaaagg    5040
ctgtttaagc ttggcaaacc tctggcagca gacgatgaac atgatgatga caggagaagg    5100
gcattgcatg aagagtcaac acgctggaac cgagtgggta ttctttcaga gctgtgcaag    5160
gcagtagaat caaggtatga aaccgtagga acttccatca tagttatggc catgactact    5220
ctagctagca gtgttaaatc attcagctac ctgagagggg cccctataac tctctacggc    5280
taacctgaat ggactacgac atagtctagt cgacgccacc atggaactgc tgatcctgaa    5340
```

```
ggccaacgcc atcaccacca tcctgaccgc cgtgaccttc tgcttcgcca gcggccagaa   5400
catcaccgag gaattctacc agagcacctg cagcgccgtg agcaagggct acctgagcgc   5460
cctgcggacc ggctggtaca ccagcgtgat caccatcgag ctgtccaaca tcaaagaaaa   5520
caagtgcaac ggcaccgacg ccaaggtgaa actgatcaag caggaactgg acaagtacaa   5580
gaacgccgtg accgagctgc agctgctgat gcagagcacc cccgccacca caaccgggc    5640
cagaagagag ctgccccggt tcatgaacta caccctgaac aacgccaaga aaccaacgt    5700
gaccctgagc aagaagcgga agcggcggag cgccatcgcc agcggggtgg ccgtgtccaa   5760
ggtgctgcac ctggaaggcg aggtgaacaa gatcaagtcc gccctgctgt ccaccaacaa   5820
ggccgtggtg tccctgagca acggcgtgag cgtgctgacc agcaaggtgc tggatctgaa   5880
gaactacatc gacaagcagc tgctgcccat cgtgaacaag cagagctgca gcatcagcaa   5940
catcgagacc gtgatcgagt ccagcagaa gaacaaccgg ctgctggaaa tcacccggga    6000
gttcagcgtg aacgccggcg tgaccacccc cgtgagcacc tacatgctga ccaacagcga   6060
gctgctgtcc ctgatcaatg acatgcccat caccaacgac cagaaaaagc tgatgagcaa   6120
caacgtgcag atcgtgcggc agcagagcta ctccatcatg agcatcatca agaagaggt    6180
gctggcctac gtggtgcagc tgcccctgta cggcgtgatc gacaccccct gctggaagct   6240
gcacaccagc cccctgtgca ccaccaacac caaagagggc agcaacatct gcctgacccg   6300
gaccgaccgg ggctggtact gcgacaacgc cggcagcgtg agcttcttcc cccaagccga   6360
gacctgcaag gtgcagagca accgggtgtt ctgcgacacc atgaacagcc tgaccctgcc   6420
ctccgaggtg aacctgtgca acgtggacat cttcaacccc aagtacgact gcaagatcat   6480
gacctccaag accgacgtga gcagctccgt gatcacctcc ctgggcgcca tcgtgagctg   6540
ctacggcaag accaagtgca ccgccagcaa caagaaccgg ggcatcatca gacctttcag   6600
caacggctgc gactacgtga gcaacaaggg cgtggacacc gtgagcgtgg gcaacacact   6660
gtactacgtg aataagcagg aaggcaagag cctgtacgtg aagggcgagc ccatcatcaa   6720
cttctacgac cccctggtgt cccccagcga cgagttcgac gccagcatca gccaggtcaa   6780
cgagaagatc aaccagagcc tggccttcat ccggaagtcc gacgagctgc tgcacaatgt   6840
gaatgccggc aagagcacca ccaatatcat gatcaccaca atcatcatcg tgatcattgt   6900
gatcctgctg tctctgattg ccgtgggcct gctgctgtac tgcaaggccc gcagcacccc   6960
tgtgaccctg tccaaggacc agctgtccgg catcaacaat atcgccttct ccaactgaag   7020
tctagacggc gcgccaccc agcggccgca tacagcagca attggcaagc tgcttacata   7080
gaactcgcgg cgattggcat gccgccttaa aattttatt ttatttttct tttcttttcc    7140
gaatcggatt ttgtttttaa tatttcaaaa aaaaaaaaa aaaaaaaaa aaaaaaaaa      7200
aaaaagaag agcgtttaaa cacgtgatat ctggcctcat gggccttcct ttcactgccc    7260
gctttccagt cgggaaacct gtcgtgccag ctgcattaac atggtcatag ctgtttcctt   7320
gcgtattggg cgctctccgc ttcctcgctc actgactcgc tgcgctcggt cgttcgggta   7380
aagcctgggg tgcctaatga gcaaaaggcc agcaaaaggc caggaaccgt aaaaaggccg   7440
cgttgctggc gtttttccat aggctccgcc ccctgacga gcatcacaaa aatcgacgct     7500
caagtcagag gtggcgaaac ccgacaggac tataaagata ccaggcgttt cccctggaa    7560
gctcccccgt gcgctctcct gttccgaccc tgccgcttac cggatacctg tccgcctttc    7620
tcccttcggg aagcgtggcg ctttctcata gctcacgctg taggtatctc agttcggtgt   7680
```

```
aggtcgttcg ctccaagctg ggctgtgtgc acgaaccccc cgttcagccc gaccgctgcg    7740
ccttatccgg taactatcgt cttgagtcca acccggtaag acacgactta tcgccactgg    7800
cagcagccac tggtaacagg attagcagag cgaggtatgt aggcggtgct acagagttct    7860
tgaagtggtg gcctaactac ggctacacta gaagaacagt atttggtatc tgcgctctgc    7920
tgaagccagt taccttcgga aaaagagttg gtagctcttg atccggcaaa caaaccaccg    7980
ctggtagcgg tggttttttt gtttgcaagc agcagattac gcgcagaaaa aaggatctc    8040 aagaagatcc tttgatcttt tctacggggt ctgacgctca gtggaacgaa aactcacgtt    8100
aagggatttt ggtcatgaat acacggtgcc tgactgcgtt agcaatttaa ctgtgataaa    8160
ctaccgcatt aaagcttatc gatgataagc tgtcaaacat gagaattctt agaaaaactc    8220
atcgagcatc aaatgaaact gcaatttatt catatcagga ttatcaatac catattttg    8280 aaaaagccgt ttctgtaatg aaggagaaaa ctcaccgagg cagttccata ggatggcaag    8340
atcctggtat cggtctgcga ttccgactcg tccaacatca atacaaccta ttaatttccc    8400
ctcgtcaaaa ataaggttat caagtgagaa atcaccatga gtgacgactg aatccggtga    8460
gaatggcaaa agcttatgca tttctttcca gacttgttca acaggccagc cattacgctc    8520
gtcatcaaaa tcactcgcat caaccaaacc gttattcatt cgtgattgcg cctgagcgag    8580
acgaaatacg cgatcgctgt taaaaggaca attacaaaca ggaatcgaat gcaaccggcg    8640
caggaacact gccagcgcat caacaatatt tcacctgaa tcaggatatt cttctaatac    8700
ctggaatgct gttttccgg ggatcgcagt ggtgagtaac catgcatcat caggagtacg    8760
gataaaatgc ttgatggtcg gaagaggcat aaattccgtc agccagttta gtctgaccat    8820
ctcatctgta acatcattgg caacgctacc tttgccatgt ttcagaaaca actctggcgc    8880
atcgggcttc ccatacaatc gatagattgt cgcacctgat tgcccgacat tatcgcgagc    8940
ccatttatac ccatataaat cagcatccat gttggaattt aatcgcggcc tcgagcaaga    9000
cgtttcccgt tgaatatggc tcataacacc ccttgtatta ctgtttatgt aagcagacag    9060
ttttattgtt catgagcgga tacatatttg aatgtatttta gaaaaataaa caaataggg    9120 ttccgcgcac atttccccga aaagtgccac ctaaattgta agcgttaata ttttgttaaa    9180 attgcgcgtta aatttttgtt aaatcagctc attttttaac caataggccg aaatcggcaa    9240
aatcccttat aaatcaaaag aatagaccga gatagggttg agtggccgct acagggcgct    9300
cccattcgcc attcaggctg cgcaactgtt gggaagggcg tttcggtgcg ggcctcttcg    9360
ctattacgcc agctggcgaa aggggatgt gctgcaaggc gattaagttg ggtaacgcca    9420
gggttttccc agtcacacgc gtaatacgac tcactataga taggcggcgc atgagagaag    9480
cccagaccaa ttacctaccc aaaatggaga aagttcacgt tgacatcgag gaagacagcc    9540
cattcctcag agctttgcag cggagcttcc cgcagtttga ggtagaagcc aagcaggtca    9600
ctgataatga ccatgctaat gccagagcgt tttcgcatct ggcttcaaaa ctgatcgaaa    9660
cggaggtgga cccatccgac acgatccttg acattggaag tgcgcccgcc cgcagaatgt    9720
attctaagca caagtatcat tgtatctgtc cgatgagatg tgcggaagat ccggacagat    9780
tgtataagta tgcaactaag ctgaagaaaa actgtaagga ataactgat aaggaattgg    9840 acaagaaaat gaaggagctc gccgccgtca tgagcgaccc tgacctggaa actgagacta    9900
tgtgcctcca cgacgacgag tcgtgtcgct acgaagggca agtcgctgtt taccaggatg    9960
tatacgcggt tgacgaccg acaagtctct atcaccaagc caataaggga gttagagtcg    10020
cctactggat aggctttgac accacccctt ttatgtttaa gaacttggct ggagcatatc    10080
```

-continued

```
catcatactc taccaactgg gccgacgaaa ccgtgttaac ggctcgtaac ataggcctat  10140
gcagctctga cgttatggag cggtcacgta gagggatgtc cattcttaga aagaagtatt  10200
tgaaaccatc caacaatgtt ctattctctg ttggctcgac catctaccac gagaagaggg  10260
acttactgag gagctggcac ctgccgtctg tatttcactt acgtggcaag caaaattaca  10320
catgtcggtg tgagactata gttagttgcg acgggtacgt cgttaaaaga atagctatca  10380
gtccaggcct gtatgggaag ccttcaggct atgctgctac gatgcaccgc gagggattct  10440
tgtgctgcaa agtgacagac acattgaacg gggagagggt ctcttttccc gtgtgcacgt  10500
atgtgccagc tacattgtgt gaccaaatga ctggcatact ggcaacagat gtcagtgcgg  10560
acgacgcgca aaaactgctg gttgggctca accagcgtat agtcgtcaac ggtcgcaccc  10620
agagaaacac caataccatg aaaaattacc ttttgcccgt agtggcccag gcatttgcta  10680
ggtgggcaaa ggaatataag gaagatcaag aagatgaaag gccactagga ctacgagata  10740
gacagttagt catggggtgt tgttgggctt ttagaaggca caagataaca tctatttata  10800
agcgcccgga tacccaaacc atcatcaaag tgaacagcga tttccactca ttcgtgctgc  10860
ccaggatagg cagtaacaca ttggagatcg ggctgagaac aagaatcagg aaaatgttag  10920
aggagcacaa ggagccgtca cctctcatta ccgccgagga cgtacaagaa gctaagtgcg  10980
cagccgatga ggctaaggag gtgcgtgaag ccgaggagtt gcgcgcagct ctaccacctt  11040
tggcagctga tgttgaggag cccactctgg aagccgatgt agacttgatg ttacaagagg  11100
ctggggccgg ctcagtggag acacctcgtg gcttgataaa ggttaccagc tacgatggcg  11160
aggacaagat cggctcttac gctgtgcttt ctccgcaggc tgtactcaag agtgaaaaat  11220
tatcttgcat ccaccctctc gctgaacaag tcatagtgat aacacactct ggccgaaaag  11280
ggcgttatgc cgtggaacca taccatggta agtagtggt gccagaggga catgcaatac  11340
ccgtccagga ctttcaagct ctgagtgaaa gtgccaccat tgtgtacaac gaacgtgagt  11400
tcgtaaacag gtacctgcac catattgcca cacatggagg agcgctgaac actgatgaag  11460
aatattacaa aactgtcaag cccagcgagc acgacggcga atacctgtac gacatcgaca  11520
ggaaacagtg cgtcaagaaa gaactagtca ctgggctagg gctcacaggc gagctggtgg  11580
atcctccctt ccatgaattc gcctacgaga gtctgagaac acgaccagcc gctccttacc  11640
aagtaccaac catagggggtg tatggcgtgc caggatcagg caagtctggc atcattaaaa  11700
gc                                                                 11702
```

CATIONIC OIL-IN-WATER EMULSIONS

RELATED APPLICATIONS

This application is a continuation of U.S. application Ser. No. 13/235,454, filed on Sep. 18, 2011, which is a continuation of International Patent Application No. PCT/US2011/043108 filed on Jul. 6, 2011, which claims the benefit of U.S. Provisional Application No. 61/361,892, filed on Jul. 6, 2010, the entire teachings of each of which are incorporated herein by reference.

SEQUENCE LISTING

The instant application contains a Sequence Listing which has been submitted via EFS-Web and is hereby incorporated by reference in its entirety. The ASCII copy, created on Mar. 2, 2012, is named Seq_List.txt, and is 48,427 bytes in size.

BACKGROUND OF THE INVENTION

Nucleic acid therapeutics have promise for treating diseases ranging from inherited disorders to acquired conditions such as cancer, infectious disorders (AIDS), heart disease, arthritis, and neurodegenerative disorders (e.g., Parkinson's and Alzheimer's). Not only can functional genes be delivered to repair a genetic deficiency or induce expression of exogenous gene products, but nucleic acid can also be delivered to inhibit endogenous gene expression to provide a therapeutic effect. Inhibition of gene expression can be mediated by, e.g., antisense oligonucleotides, double-stranded RNAs (e.g., siRNAs, miRNAs), or ribozymes.

A key step for such therapy is to deliver nucleic acid molecules into cells in vivo. However, in vivo delivery of nucleic acid molecules, in particular RNA molecules, faces a number of technical hurdles. First, due to cellular and serum nucleases, the half life of RNA injected in vivo is only about 70 seconds (see, e.g., Kurreck, Eur. J. Bioch. 270: 1628-44 (2003)). Efforts have been made to increase stability of injected RNA by the use of chemical modifications; however, there are several instances where chemical alterations led to increased cytotoxic effects or loss of or decreased function. In one specific example, cells were intolerant to doses of an RNAi duplex in which every second phosphate was replaced by phosphorothioate (Harborth, et al, Antisense Nucleic Acid Drug Rev. 13(2): 83-105 (2003)). As such, there is a need to develop delivery systems that can deliver sufficient amounts of nucleic acid molecules (in particular RNA molecules) in vivo to elicit a therapeutic response, but that are not toxic to the host.

Nucleic acid based vaccines are an attractive approach to vaccination. For example, intramuscular (IM) immunization of plasmid DNA encoding for antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype.

Another limitation of nucleic acid based vaccines is that large doses of nucleic acid are generally required to obtain potent immune responses in non-human primates and humans. Therefore, delivery systems and adjuvants are required to enhance the potency of nucleic acid based vaccines. Various methods have been developed for introducing nucleic acid molecules into cells, such as calcium phosphate transfection, polyprene transfection, protoplast fusion, electroporation, microinjection and lipofection.

Cationic lipids have been widely formulated as liposomes to deliver genes into cells. However, even a small amount of serum (~10%) can dramatically reduce the transfection activity of liposome/DNA complexes because serum contains anionic materials. Recently, cationic lipid emulsion was developed to deliver DNA molecules into cells. See, e.g., Kim, et al., International Journal of Pharmaceutics, 295, 35-45 (2005).

U.S. Pat. Nos. 6,753,015 and 6,855,492 describe a method of delivering nucleic acid molecules to a vertebrate subject using cationic microparticles. The microparticles comprise a polymer, such as a poly($\alpha$-hydroxy acid), a polyhydroxy butyric acid, a polycaprolactone, a polyorthoester, a polyanhydride, and the like, and are formed using cationic surfactants. Nucleic acid molecules are adsorbed on the surfaces of the microparticles.

Kim et al. (Pharmaceutical Research, vol. 18, pages 54-60, 2001) and Chung et al. (Journal of Controlled Release, volume 71, pages 339-350, 2001) describe various oil-in-water emulsion formulations that are used to enhance in vitro and in vivo transfection efficiency of DNA molecules.

Ott et al. (Journal of Controlled Release, volume 79, pages 1-5, 2002) describes an approach involving a cationic sub-micron emulsion as a delivery system/adjuvant for DNA. The sub-micron emulsion approach is based on MF59, a potent squalene in water adjuvant which has been manufactured at large scale and has been used in a commercially approved product (Fluad®). 1,2-dioleoyl-3-trimethylammonium-propane (DOTAP) was used to facilitate intracellular delivery of plasmid DNA.

Although DNA-based vaccines hold great promise for prevention and treatment of diseases, general concerns have been raised regarding their safety. The introduced DNA molecules could potentially integrate into the host genome or, due to their distribution to various tissues, could lead to undesirable sustained expression of antigens. In addition, certain DNA viruses have also been used as a vehicle to deliver DNA molecules. Because of their infectious properties, such viruses achieve a very high transfection rate. The viruses used are genetically modified in such a manner that no functional infectious particles are formed in the transfected cell. Despite these precautions, however, it is not possible to rule out the risk of uncontrolled propagation of the introduced gene and viral genes, for example due to potential recombination events. This also entails the risk of the DNA being inserted into an intact gene of the host cell's genome by e.g. recombination, with the consequence that this gene may be mutated and thus completely or partially inactivated or may give rise to misinformation. In other words, synthesis of a gene product which is vital to the cell may be completely suppressed or, alternatively, a modified or incorrect gene product is expressed. In addition, it is generally difficult to scale up the manufacture and purification of clinical-grade viral vectors.

One particular risk occurs if the DNA is integrated into a gene which is involved in the regulation of cell growth. In this case, the host cell may become degenerate and lead to cancer or tumor formation. Furthermore, if the DNA introduced into the cell is to be expressed, it is necessary for the corresponding DNA vehicle to contain a strong promoter, such as the viral CMV promoter. The integration of such promoters into the genome of the treated cell may result in unwanted alterations of the regulation of gene expression in the cell. Another risk of using DNA as an agent to induce an immune response (e.g. as a vaccine) is the induction of pathogenic anti-DNA antibodies in the patient into whom the foreign DNA has been introduced, so bringing about an undesirable immune response.

RNA molecules encoding an antigen or a derivative thereof may also be used as vaccines. RNA vaccines offer certain advantages as compared to DNA vaccines. First, RNA cannot integrate into the host genome thus abolishing the risk of malignancies. Second, due to the rapid degradation of RNA, expression of the foreign transgene is often short-lived, avoiding uncontrolled long term expression of the antigen. Third, RNA molecules only need to be delivered to the cytoplasm to express the encoded antigen, whereas DNA molecules must permeate through the nuclear membrane.

Nonetheless, compared with DNA-based vaccines, relatively minor attention has been given to RNA-based vaccines. RNAs and oligonucleotides are hydrophilic, negatively charged molecules that are highly susceptible to degradation by nucleases when administered as a therapeutic or vaccine. Additionally, RNAs and oligonucleotides are not actively transported into cells. See, e.g., Vajdy, M., et al., *Mucosal adjuvants and delivery systems for protein-, DNA- and RNA-based vaccines*, Immunol Cell Biol, 2004. 82(6): p. 617-27.

Ying et al. (Nature Medicine, vol. 5, pages 823-827, 1999) describes a self-replicating RNA vaccine in which naked RNA encoding β-galactosidase was delivered and the induction of CD8+ cells was reported.

Montana et al. (Bioconjugate Chem. 2007, 18, pages 302-308) describes using cationic solid-lipid nanoparticles as RNA carriers for gene transfer. It was shown that solid-lipid nanoparticles protected the RNA molecule from degradation, and the expression of reporter protein (fluorescein) was detected after microinjecting the RNA-particle complex into sea urchin eggs.

WO 2010/009277 discloses Nano Lipid Peptide Particles (NLPPs) comprising (a) an amphipathic peptide, (b) a lipid, and (c) at least one immunogenic species. In certain embodiments, the NLPPs also incorporate a positively charged "capturing agent," such as a cationic lipid. The capturing agent is used to anchor a negatively charged immunogenic species (e.g., a DNA molecule or an RNA molecule). Preparation of NLPP requires amphipathic peptides, which are used to solubilize the lipid component and to form nano-particles.

Therefore, there is a need to provide delivery systems for nucleic acid molecules or other negatively charged molecules. The delivery systems are useful for nucleic acid-based vaccines, in particular RNA-based vaccines.

SUMMARY OF THE INVENTION

This invention generally relates to cationic oil-in-water emulsions that can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. The cationic emulsions described herein are particularly suitable for delivering nucleic acid molecules (such as an RNA molecule encoding an antigen) to cells and formulating nucleic acid-based vaccines.

In one aspect, the invention provides a composition comprising an RNA molecule complexed with a particle of a cationic oil-in-water emulsion, wherein the particle comprises (a) an oil core that is in liquid phase at 25° C., and (b) a cationic lipid. Preferably, the cationic oil-in-water emulsion particle is not a Nano Lipid Peptide Particle (NLPP). Preferably, the oil core is in liquid phase at 4° C. Optionally, the average diameter of the emulsion particles is from about 80 nm to about 180 nm and the N/P of the emulsion is at least 4:1. Optionally, the emulsion is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the emulsion further comprises a non-ionic tonicifying agent, such as a sugar, sugar alcohol or a combination thereof, in a sufficient quantity to make the emulsion isotonic.

In certain embodiments, the cationic oil-in-water emulsion further comprises a surfactant, such as a nonionic surfactant. Exemplary nonionic surfactants include, e.g., SPAN85 (sorbtian trioleate), Tween 80 (polysorbate 80; polyoxyethylenesorbitan monooleate), or a combination thereof. The cationic oil-in-water emulsion may comprise from about 0.01% to about 2.5% (v/v) surfactant. For example, the cationic oil-in-water emulsion may comprise about 0.08% (v/v) Tween 80, or alternatively, about 0.5% (v/v) Tween 80 and about 0.5% (v/v) SPAN85. A Polyethylene Glycol (PEG) or PEG-lipid, such as $PEG_{2000}PE$, $PEG_{5000}PE$, $PEG_{1000}DMG$, $PEG_{2000}DMG$, $PEG_{3000}DMG$, or a combination thereof, may also be used.

The composition comprising an RNA molecule complexed with a particle of a cationic oil-in-water emulsion may comprise from about 0.005% to about 1.25% (v/v) surfactant. For example, the composition comprising the RNA-emulsion complex may comprise about 0.04% (v/v) Tween 80 (polysorbate 80; polyoxyethylenesorbitan monooleate), or alternatively, about 0.25% (v/v) Tween 80 and about 0.25% (v/v) SPAN85 (sorbtian trioleate).

In certain embodiments, the cationic oil-in-water emulsion further comprises a phospholipid. Exemplary phospholipid include, 1,2-dioleoyl-sn-glycero-3-phosphatidylethanolamine (DOPE), 1,2-diphytanoyl-sn-glycero-3-phosphoethanolamine (DPyPE), or Egg phosphatidylcholine (egg PC). For example, the cationic oil-in-water emulsion may comprise from about 0.1 mg/ml to about 20 mg/ml (preferably, from about 0.1 mg/ml to about 10 mg/ml) DOPE, or alternatively, from about 0.1 mg/ml to about 20 mg/ml (preferably, from about 0.1 mg/ml to about 10 mg/ml) DPyPE, or alternatively, from about 0.1 mg/ml to about 20 mg/ml (preferably, from about 0.1 mg/ml to about 10 mg/ml) egg PC.

The composition comprising an RNA molecule complexed with a particle of a cationic oil-in-water emulsion may comprise from about 0.05 mg/ml to about 10 mg/ml (preferably, from about 0.05 mg/ml to about 5 mg/ml) DOPE, or alternatively, from about 0.05 mg/ml to about 10 mg/ml (preferably, from about 0.05 mg/ml to about 5 mg/ml) DPyPE, or alternatively, from about 0.05 mg/ml to about 10 mg/ml (preferably, from about 0.05 mg/ml to about 5 mg/ml) egg PC.

In certain embodiments, the cationic oil-in-water emulsion further comprises a polymer or a surfactant in the aqueous phase of the emulsion. Exemplary polymers include poloxamers such as Pluronic® F127 (Ethylene Oxide/Propylene Oxide Block Copolymer: $H(OCH_2CH_2)_x(OCH_3CH(CH_3))_y(OCH_2CH_2)_7OH)$. For example, the cationic oil-in-water emulsion may comprise from about 0.05% to about 20% (w/v) polymer, or from about 0.1% to about 10% (w/v) polymer, such as 0.5% (w/v) or 1% (w/v) Pluronic® F127. The composition comprising an RNA molecule complexed with a particle of a cationic oil-in-water emulsion may comprise from about 0.025% to about 10% (v/v) polymer, or from about 0.5% to about 5% (v/v) polymer, such as 0.25% (w/v), or 0.5% (w/v) Pluronic® F127.

The emulsions may comprise components that can promote particle formation, improve the complexation between the negatively charged molecules and the cationic particles, facilitate appropriate decomplexation/release of the negatively charged molecules (such as an RNA molecule), increase the stability of the negatively charged molecule (e.g., to prevent degradation of an RNA molecule), or prevent aggregation of the emulsion particles.

In certain embodiments, the oil core may comprise an oil that is selected from the following: Castor oil, Coconut oil, Corn oil, Cottonseed oil, Evening primrose oil, Fish oil, *Jojoba* oil, Lard oil, Linseed oil, Olive oil, Peanut oil, Safflower oil, Sesame oil, Soybean oil, Squalene, Sunflower oil, Wheatgerm oil, Mineral oil, or a combination thereof. Preferably, the oil is Soybean oil, Sunflower oil, Olive oil, Squalene, or a combination thereof. The cationic oil-in-water emulsion may comprise from about 0.2% to about 20% (v/v) oil, preferably about 0.08% to about 5% oil, about 0.08% oil, about 4% to about 5% oil, about 4% oil, about 4.3% oil, or about 5% oil. The composition comprising an RNA molecule complexed with a particle of a cationic oil-in-water emulsion may comprise from about 0.1% to about 10% (v/v) oil, preferably, from about 2% to about 2.5% (v/v) oil.

In certain embodiments, the cationic lipid is selected from one of the following: 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl ($C_{16:0}$)trimethyl ammonium propane (DPTAP), distearoyltrimethylammonium propane (DSTAP), Lipids E0001-E0118 or E0119-E0180 as disclosed in Table 6 (pages 112-139) of WO 2011/076807 (incorporated herein by reference), or a combination thereof. Particularly preferred cationic lipids include DOTAP, DC Cholesterol, and DDA.

In certain embodiments, the cationic lipid is selected from one of the following: 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl ($C_{16:0}$)trimethyl ammonium propane (DPTAP), distearoyltrimethylammonium propane (DSTAP), Lipids E0001-E0118 or E0119-E0180 as disclosed in Table 6 (pages 112-139) of WO 2011/076807 (incorporated herein by reference), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), or a combination thereof. Particularly preferred cationic lipids include DOTAP, DC Cholesterol, DDA, DOTMA, DOEPC, DSTAP, DODAC, DODAP, and DLinDMA.

In certain embodiments, the cationic oil-in-water emulsion comprises from about 0.8 mg/ml to about 3 mg/ml, preferably from about 0.8 mg/ml to about 1.6 mg/ml DOTAP.

The composition comprising an RNA molecule complexed with a particle of a cationic oil-in-water emulsion may comprise from about 0.4 mg/ml to about 1.5 mg/ml, preferably from about 0.4 mg/ml to about 0.8 mg/ml DOTAP. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In certain embodiments, the cationic oil-in-water emulsion comprises from about 0.62 mg/ml to about 4.92 mg/ml DC Cholesterol.

The composition comprising an RNA molecule complexed with a particle of a cationic oil-in-water emulsion may comprise from about 0.31 mg/ml to about 2.46 mg/ml DC Cholesterol. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In certain embodiments, the cationic oil-in-water emulsion comprises from about 0.73 mg/ml to about 1.45 mg/ml DDA.

The composition comprising an RNA molecule complexed with a particle of a cationic oil-in-water emulsion may comprise from about 0.365 mg/ml to about 0.725 mg/ml DDA. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In certain embodiments, the cationic oil-in-water emulsion comprises from about 0.8 mg/ml to about 3 mg/ml, preferably from about 0.8 mg/ml to about 1.6 mg/ml DOTMA.

The composition comprising an RNA molecule complexed with a particle of a cationic oil-in-water emulsion may comprise from about 0.4 mg/ml to about 1.5 mg/ml, preferably from about 0.4 mg/ml to about 0.8 mg/ml DOTMA. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In certain embodiments, the cationic oil-in-water emulsion comprises from about 0.8 mg/ml to about 3 mg/ml, preferably from about 0.8 mg/ml to about 1.8 mg/ml DOEPC.

The composition comprising an RNA molecule complexed with a particle of a cationic oil-in-water emulsion may comprise from about 0.4 mg/ml to about 1.5 mg/ml, preferably from about 0.4 mg/ml to about 0.9 mg/ml DOEPC. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In certain embodiments, the cationic oil-in-water emulsion comprises from about 0.73 mg/ml to about 1.45 mg/ml DODAC.

The composition comprising an RNA molecule complexed with a particle of a cationic oil-in-water emulsion may comprise from about 0.365 mg/ml to about 0.725 mg/ml DODAC. Optionally, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In one example, the invention provides a composition comprising a negatively charged molecule complexed with a particle of a cationic oil-in-water emulsion, wherein the cationic oil-in-water emulsion comprises (a) about 0.5% (v/v) oil, and (b) a cationic lipid.

In one example, the invention provides a composition comprising a negatively charged molecule complexed with a particle of a cationic oil-in-water emulsion, wherein the composition comprises (a) about 0.25% (v/v) oil, and (b) a cationic lipid.

In another example, the invention provides a composition comprising a negatively charged molecule complexed with a particle of a cationic oil-in-water emulsion, wherein the particle comprises (a) an oil core, (b) a cationic lipid, and (c) a phospholipid. Preferred phospholipids include, e.g., DPyPE, DOPE, and egg PC. Preferably, the composition (negatively charged molecule-emulsion complex) comprises from about 0.05 mg/ml to about 10 mg/ml (more preferably, from about 0.05 mg/ml to about 5 mg/ml) DOPE, or alternatively, from about 0.05 mg/ml to about 10 mg/ml (more preferably, from about 0.05 mg/ml to about 5 mg/ml) DPyPE, or alternatively, from about 0.05 mg/ml to about 10 mg/ml (more preferably, from about 0.05 mg/ml to about 5 mg/ml) egg PC.

In another example, the invention provides a composition comprising a negatively charged molecule complexed with a particle of a cationic oil-in-water emulsion, wherein the particle comprises (a) an oil core and (b) DOTAP, and wherein the oil-in-water emulsion comprises from about 0.8 mg/ml to about 3.0 mg/ml DOTAP, preferably from about 0.8 mg/ml to about 1.6 mg/ml DOTAP. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DOTAP, and wherein the composition comprises from about 0.4 mg/ml to about 1.5 mg/ml DOTAP, such as 0.4 mg/ml, 0.6 mg/ml, 0.7 mg/ml, 0.8 mg/ml, etc. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DC Cholesterol, and wherein the oil-in-water emulsion comprises from about 2.46 mg/ml to about 4.92 mg/ml DC Cholesterol. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0; preferably about 6.2 to about 6.8, and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DC Cholesterol, and wherein the composition comprises from about 1.23 mg/ml to about 2.46 mg/ml DC Cholesterol, such as 1.23 mg/ml. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DDA, and wherein the oil-in-water emulsion comprises from about 0.73 mg/ml to about 1.45 mg/ml DDA. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DDA, and wherein the composition comprises from about 0.365 mg/ml to about 0.725 mg/ml DDA, such as 0.725 mg/mL. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DOTMA, and wherein the composition comprises from about 0.4 mg/ml to about 1.5 mg/ml, preferably from about 0.4 mg/ml to about 0.8 mg/ml DOTMA. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DOEPC, and wherein the composition comprises from about 0.4 mg/ml to about 1.5 mg/ml, preferably from about 0.4 mg/ml to about 0.9 mg/ml DOEPC. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

In another example, the invention provides a composition comprising a negatively charged molecule complexed with a particle of a cationic oil-in-water emulsion, wherein the particle comprises (a) an oil core and (b) DODAC, and wherein the composition comprises from about 0.365 mg/ml to about 0.725 mg/ml DODAC. In some embodiments, the negatively charged molecule is RNA, the average diameter of the emulsion particles is from about 80 nm to about 180 nm and the N/P of the emulsion is at least 4:1. Optionally, the composition is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Optionally, the composition further comprises a nonionic tonicifying agent, such as a sugar, sugar alcohol or a combination thereof, in a sufficient quantity to make the composition isotonic.

Examples of negatively charged molecules include negatively charged peptide-containing antigens, nucleic acid molecules (e.g., RNA or DNA) that encode one or more peptide-containing antigens, negatively charged small molecules, and negatively charged immunological adjuvants. Negatively charged immunological adjuvants include, e.g., immunostimulatory oligonucleotides (e.g., CpG oligonucleotides), single-stranded RNAs, small molecule immune potentiators (SMIPs), etc. Negatively charged small molecules includes, e.g. phosphonate, fluorophosphonate, etc.

In certain embodiments, the negatively charged molecule is a nucleic acid molecule, such as an RNA molecule, that encodes an antigen. In certain embodiments, the RNA molecule is a self-replicating RNA molecule, such as an alphavirus-derived RNA replicon.

In another aspect, the invention provides immunogenic cationic oil-in-water emulsion comprising emulsion particles that contain an oil core (preferably that is in liquid phase at 25° C.) and a cationic lipid, and a nucleic acid molecule that is complexed to the emulsion particles, and wherein the average diameter of the emulsion particles is from about 80 nm to about 180 nm and the N/P of the emulsion is at least 4:1. In certain embodiments, the nucleic acid molecule is an RNA, such as a self replicating RNA. Preferably, the immunogenic cationic oil-in-water emulsion is buffered (e.g., with a citrate buffer, a succinate buffer, an acetate buffer etc.) and has a pH from about 6.0 to about 8.0, preferably about 6.2 to about 6.8; and contains no more than 30 mM inorganic salt (e.g., NaCl). Preferably, the the immunogenic cationic oil-in-water emulsion further comprises a nonionic tonicifying agent, such as a sugar, sugar alcohol or a combination thereof, in a sufficient quantity to make the emulsion isotonic.

In another aspect, the invention provides a method of preparing a composition that comprises a negatively charged molecule complexed with a particle of a cationic oil-in-water emulsion, comprising: (A) preparing a cationic oil-in-water emulsion wherein the emulsion comprises: (1) from about 0.2% to about 20% (v/v) oil, (2) from about 0.01% to about 2.5% (v/v) surfactant, and (3) a cationic lipid that is selected from the group consisting of: (i) from about 0.8 mg/ml to about 1.6 mg/ml DOTAP, (ii) from about 2.46 mg/ml to about 4.92 mg/ml DC Cholesterol, and (iii) from about 0.73 mg/ml to about 1.45 mg/ml DDA; and (B) adding the negatively charged molecule to the cationic oil-in-water emulsion so that the negatively charged molecule complexes with the particle of the emulsion.

In another aspect, the invention provides a method of preparing a composition that comprises a negatively charged molecule complexed with a particle of a cationic oil-in-water emulsion, comprising: (A) preparing a cationic oil-in-water emulsion wherein the emulsion comprises: (1) from about 0.2% to about 20% (v/v) oil, (2) from about 0.01% to about 2.5% (v/v) surfactant, and (3) a cationic lipid that is selected from the group consisting of: (i) from about 0.8 mg/ml to about 1.6 mg/ml DOTAP, (ii) from about 2.46 mg/ml to about 4.92 mg/ml DC Cholesterol, (iii) from about 0.73 mg/ml to about 1.45 mg/ml DDA, (iv) from about 0.8 mg/ml to about 1.6 mg/ml DOTMA, (v) from about 0.8 mg/ml to about 1.8 mg/ml DOEPC; and (vi) from about 0.73 mg/ml to about 1.45 mg/ml DODAC; and (B) adding the negatively charged molecule to the cationic oil-in-water emulsion so that the negatively charged molecule complexes with the particle of the emulsion.

In certain embodiments, the cationic oil-in-water emulsion is prepared by the process comprising: (1) combining the oil and the cationic lipid to form the oil phase of the emulsion; (2) providing the aqueous phase (i.e., continuous phase) of the emulsion; and (3) dispersing the oil phase in the aqueous phase by homogenization. The cationic lipid may be dissolved directly in the oil. Alternatively, the cationic lipid may be dissolved in any suitable solvent, such as chloroform ($CHCl_3$) or dichloromethane (DCM). Isopropyl alcohol may also be used. The solvent may be evaporated before the oil phase is added to the aqueous phase, or after the oil phase is added to the aqueous phase but before homogenization. Alternatively, in instances where lipid solubility can be an issue, a primary emulsion can be made with the solvent (e.g., DCM) still in the oil phase. In that case, the solvent would be allowed to evaporate directly from the emulsion prior to a secondary homogenization.

Additional optional steps to promote particle formation, to improve the complexation between the negatively charged molecules and the cationic particles, to increase the stability of the negatively charged molecule (e.g., to prevent degradation of an RNA molecule), to facilitate appropriate decomplexation/release of the negatively charged molecules (such as an RNA molecule), or to prevent aggregation of the emulsion particles may be included. For example, a polymer (e.g., Pluronic® F127) or a surfactant may be added to the aqueous phase of the emulsion. In one exemplary embodiment, Pluronic® F127 is added to the RNA molecule prior to complexation to the emulsion particles. Addition of Pluronic® F127 can increase the stability of the RNA molecule and further reduce RNA degradation. Poloxamer polymers can also promote the release of the RNA molecule and prevent aggregation of the emulsion particles. Finally, poloxamer polymers also have immune modulatory effect. See, e.g., Westerink et al., Vaccine. 2001 Dec. 12; 20(5-6): 711-23.

Preferably, the RNA molecule of the RNA-cationic particle complex is more resistant to RNase degradation as compared to uncomplexed RNA molecule.

In another aspect, the invention provides a pharmaceutical composition comprising a negatively charged molecule complexed with a particle of a cationic oil-in-water emulsion, as described herein, and may further comprise one or more pharmaceutically acceptable carriers, diluents, or excipients. In preferred embodiments, the pharmaceutical composition is a vaccine.

In another aspect, the invention provides a method of generating an immune response in a subject, comprising administering to a subject in need thereof a composition as described herein.

The invention also relates to a pharmaceutical composition as described herein for use in therapy, and to the use of a pharmaceutical composition as described herein for the manufacture of a medicament for potentiating or generating an immune response.

Figure 1:
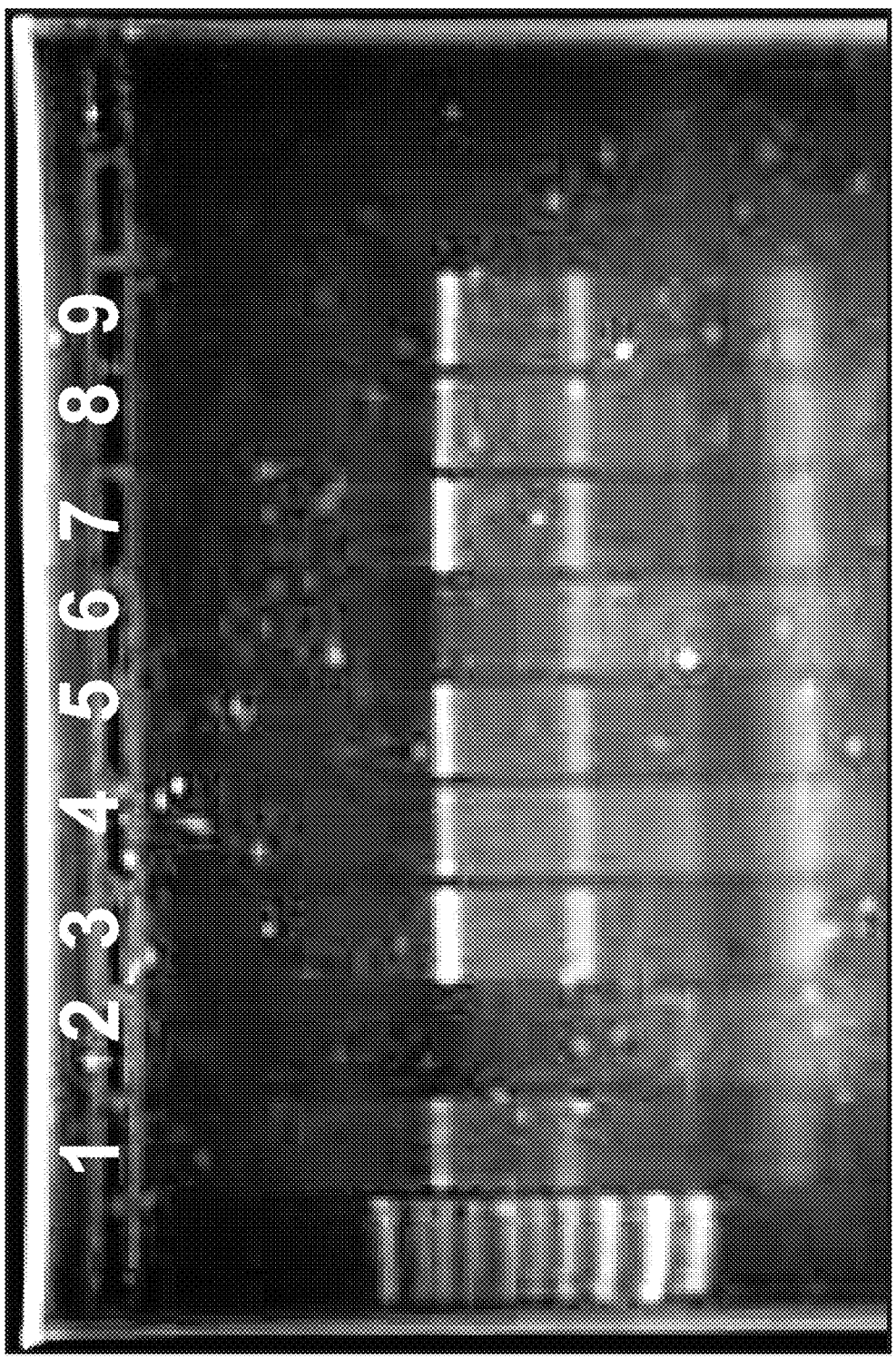
FIG. 1 shows the stability of mouse thymus RNA in the presence of RNase after the RNA molecule was complexed with cationic nano-emulsion (CNE) particles. All samples were incubated with RNase for 30 minutes. RNase was inactivated with proteinase K. Samples that were formulated with CNEs were decomplexed and analyzed for RNA integrity by denaturing gel electrophoresis. Unlabeled lane contains molecular weight markers. Lanes 1 and 2: mouse thymus RNA before (1) and after (2) RNase digestion; lanes 3 and 4: mouse thymus RNA complexed with CNE01 at an N/P ratio of 10:1 before (3) and after (4) RNase digestion; lanes 5 and 6: mouse thymus RNA complexed with CNE01 at an N/P ratio of 4:1 before (5) and after (6) RNase digestion; lanes 7 and 8: mouse thymus RNA complexed with CNE17 at an N/P ratio of 10:1 before (7) and after (8) RNase digestion; lane 9 mouse thymus RNA complexed with CNE17 at an N/P ratio of 4:1 before (9) RNase digestion.

and after (18) RNase digestion; lanes 19 and 20: mouse thymus RNA complexed with CNE04 at an N/P ratio of 4:1 before (19) and after (20) RNase digestion; lanes 21 and 22: mouse thymus RNA complexed with CNE05 at an N/P ratio of 10:1 before (21) and after (22) RNase digestion; lanes 23 and 24: mouse thymus RNA complexed with CNE05 at an N/P ratio of 4:1 before (23) and after (24) RNase digestion.

Figure 5:
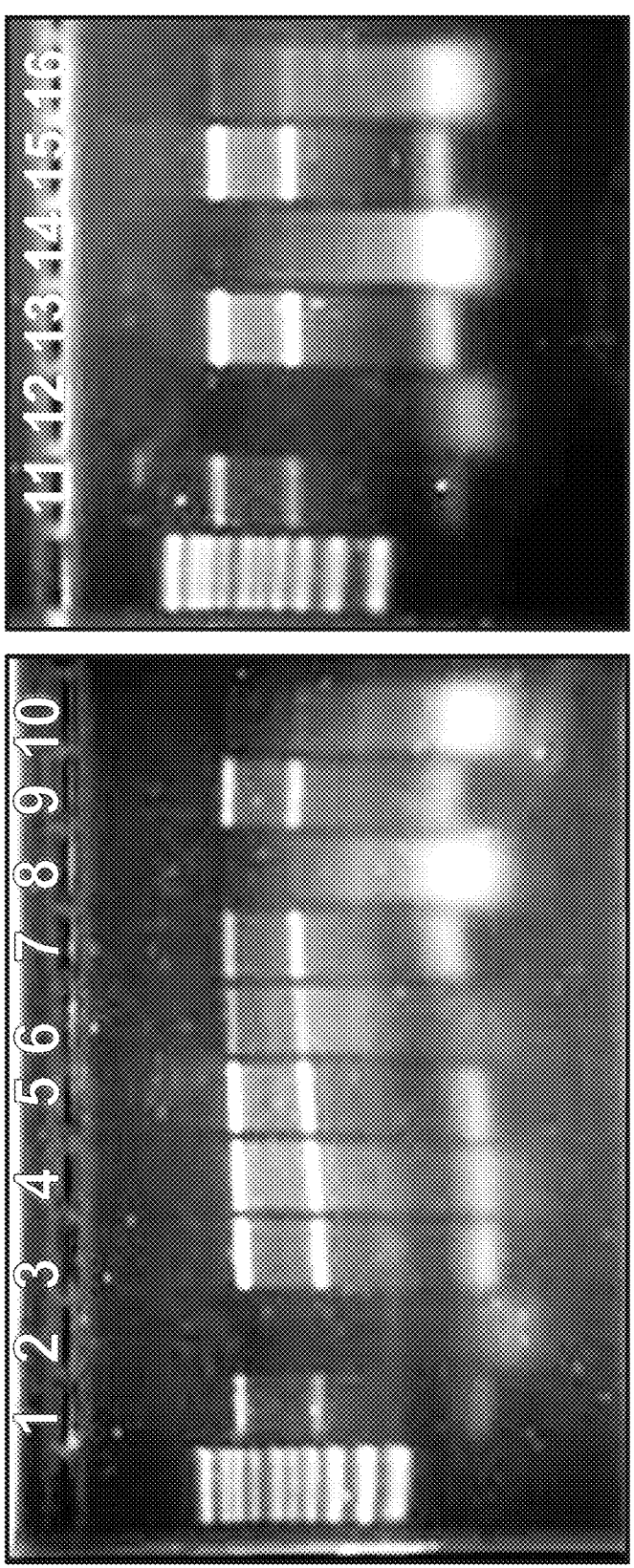

FIG. 5 shows the stability of mouse thymus RNA in the presence of RNase after the RNA molecule was complexed with CNE particles. All samples were incubated with RNase for 30 minutes. RNase was inactivated with proteinase K and samples that were formulated were decomplexed and analyzed for RNA integrity by denaturing gel electrophoresis. Unlabeled lanes contain molecular weight markers. Lanes 1 and 2: mouse thymus RNA before (1) and after (2) RNase digestion; lanes 3 and 4: mouse thymus RNA complexed with CNE17 at an N/P ratio of 10:1 before (3) and after (4) RNase digestion; lanes 5 and 6: mouse thymus RNA complexed with CNE17 at an N/P ratio of 4:1 before (5) and after (6) RNase digestion; lanes 7 and 8: mouse thymus RNA complexed with CNE27 at an N/P ratio of 10:1 before (7) and after (8) RNase digestion; lanes 9 and 10: mouse thymus RNA complexed with CNE27 at an N/P ratio of 4:1 before (9) and after (10) RNase digestion; lanes 11 and 12: mouse thymus RNA before (11) and after (12) RNase digestion; lanes 13 and 14: mouse thymus RNA complexed with CNE32 at an N/P ratio of 10:1 before (13) and after (14) RNase digestion; lanes 15 and 16: mouse thymus RNA complexed with CNE32 at an N/P ratio of 4:1 before (15) and after (16) RNase digestion.

Figure 6:
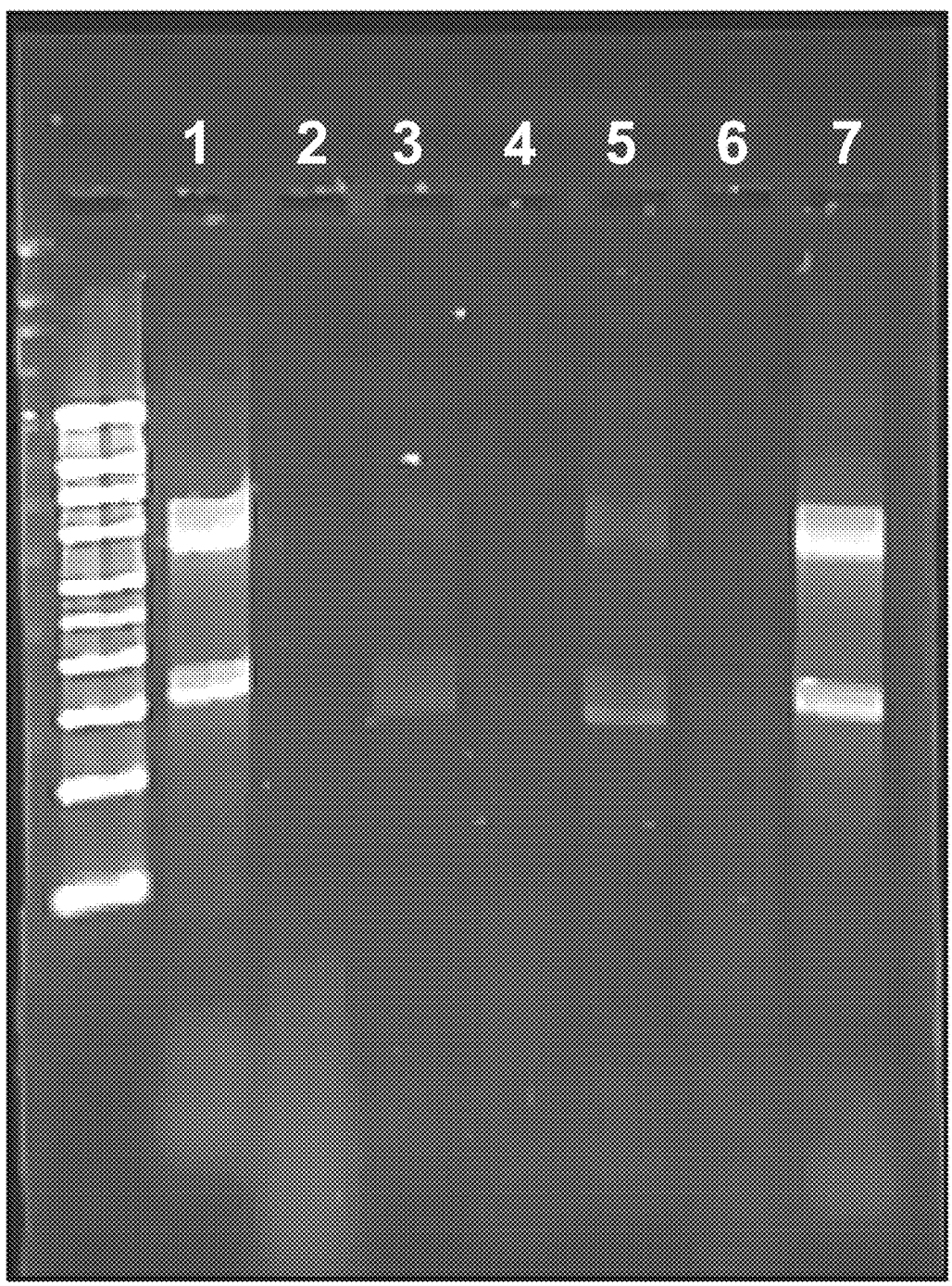

FIG. 6 shows the stability of mouse thymus RNA in the presence of RNase after the RNA molecule was complexed with CNE particles. All samples were incubated with RNase for 30 minutes. RNase was inactivated with proteinase K and samples that were formulated were decomplexed and analyzed for RNA integrity by denaturing gel electrophoresis. Unlabeled lanes contain molecular weight markers. Lanes 1 and 2: mouse thymus RNA before (1) and after (2) RNase digestion; lanes 3 and 4: mouse thymus RNA complexed with CNE35 at an N/P ratio of 10:1 before (3) and after (4) RNase digestion; lanes 5 and 6: mouse thymus RNA complexed with CNE35 at an N/P ratio of 4:1 before (5) and after (6) RNase digestion; lane 7: mouse thymus RNA before RNase digestion.

FIGS. 7A-7C show the sequences of the vectors used in the examples. FIG. 7A shows the sequence of plasmid A317 (SEQ ID NO:1), which encodes the RSV-F antigen. FIG. 7B shows the sequence of plasmid A306 (SEQ ID NO:2), which encodes secreted human placental alkaline phosphatase (SEAP). FIG. 7C shows the sequence of plasmid A375 (SEQ ID NO:3), which encodes an RSV-F antigen.

Figure 8A:
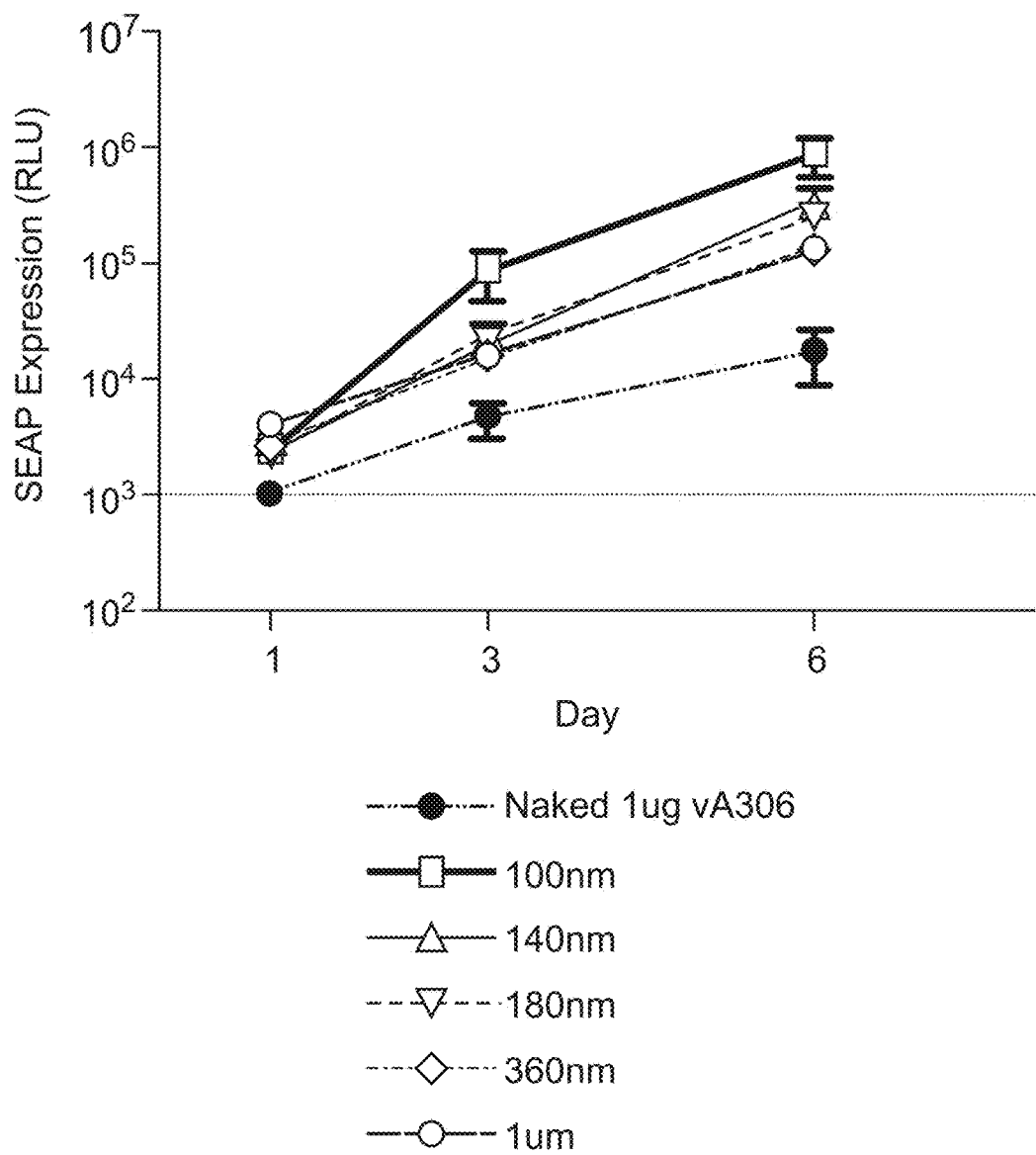

FIG. 8A shows the results of the in vivo SEAP assay, using 1 µg of RNA replicon A306 complexed with CNE17 at 10:1 N/P ratio. FIG. 8B the total IgG titers in BALB/c mice at 2wp1 and 2wp2 time points (RNA replicon A317 complexed with CNE17 were administered to the BALB/c).

FIGS. 9A-9C show the effects of different buffer compositions on particle size. FIG. 9A shows the effects of sugar, salt, and polymer F127 on particle size of CNE17 emulsions with RNA complexed at N/P of 10:1. FIG. 9B shows the effect of citrate buffer on particle size of CNE17 emulsion. FIG. 9C shows the effect of polymers (F68, F127 and PEG300) on particle size.

DETAILED DESCRIPTION OF THE INVENTION

1. Overview

This invention generally relates to cationic oil-in-water emulsions that can be used to deliver negatively charged molecules, such as an RNA molecule to cells. The emulsion particles comprise an oil core and a cationic lipid. The cationic lipid can interact with the negatively charged molecule, for example through electrostatic forces and hydrophobic/hydrophilic interactions, thereby anchoring the molecule to the emulsion particles. The cationic emulsions described herein are particularly suitable for delivering nucleic acid molecules, such as an RNA molecules (e.g., RNA that encoding a protein or peptide, small interfering RNA, self-replicating RNA, and the like) to cells in vivo.

The present invention is based on the discovery that cationic oil-in-water emulsions can be used to deliver negatively charged molecules to cells. The emulsion particles comprise an oil core, and a cationic lipid that can interact with the negatively charged molecule. In preferred embodiments, an RNA molecule is complexed, for example through electrostatic forces and hydrophobic/hydrophilic interactions, with a particle of a cationic oil-in-water emulsion. The complexed RNA molecule is stabilized and protected from RNase-mediated degradation, and is more efficiently taken up by cells relative to free RNA. In addition, when the RNA is delivered to induce expression of an encoded protein, such as in the context of an RNA vaccine, the immunogenicity of the encoded protein can be enhanced due to adjuvant effects of the emulsion. Therefore, in addition to more efficient delivery of a negatively charged molecule (e.g., an RNA molecule that encodes an antigen), the cationic emulsions can also enhance the immune response through adjuvant activity.

For example, as described and exemplified herein, the inventors evaluated the in vivo effects of a series of cationic oil-in-water emulsions, using a mouse model and a cotton rat model of respiratory syncytial virus (RSV) immunization. The results demonstrate that formulations in which the RNA molecules were complexed with cationic emulsions generated significantly higher immune responses as compared to free RNA formulations. In some cases, the average antibody titers against an RNA encoded protein that were obtained following administration of 1 µg of RNA complexed with a cationic oil-in-water emulsions, were comparable to titers obtained using 10 times more free RNA (10 µg dose of free RNA). Another advantage of the formulations as described herein, in addition to higher immune responses in the host, is that there was less fluctuation in the immune responses in the host animals between different studies and different host animals, as compared to free (unformulated) RNA.

Accordingly, in one aspect, the invention provides a composition comprising an RNA molecule complexed with a particle of a cationic oil-in-water emulsion, wherein the particle comprises (a) an oil core that is in liquid phase at 25° C., and (b) a cationic lipid. Preferably, the cationic oil-in-water emulsion particle is not a Nano Lipid Peptide Particle (NLPP). Preferably, the oil core is in liquid phase at 4° C.

The cationic emulsion particles may further comprises a surfactant (e.g., Tween 80 (polysorbate 80; polyoxyethylenesorbitan monooleate), SPAN85 (sorbtian trioleate), or a combination thereof), a phospholipid, or a combination thereof. The emulsion may also comprise a polymer (e.g., Pluronic® F127) in the aqueous phase (the continuous phase) of the emulsion.

In another aspect, the invention also provides several specific formulations of cationic oil-in-water emulsions that can be used to deliver negatively charged molecules.

In another aspect, the invention provides a method of preparing a composition that comprises a negatively charged molecule complexed with a particle of a cationic oil-in-water emulsion. One exemplary approach to produce cationic emulsions described herein is by dispersing the oil phase in the aqueous phase by homogenization. Additional optional steps to promote particle formation, to improve the complexation between the negatively charged molecules and the cationic particles, to increase the stability of the negatively charged molecule (e.g., to prevent degradation of an RNA molecule), to facilitate appropriate decomplexation/release of the negatively charged molecules (such as an RNA molecule), or to prevent aggregation of the emulsion particles include, for example, adding dichloromethane (DCM or methylene chloride) into the oil phase, and allowing DCM to evaporate before or after homogenization; mixing the cationic lipid with a suitable solvent to form a liposome suspension; or adding a polymer (e.g., Pluronic® F127) or a surfactant to the aqueous phase of the emulsion. Alternatively, the cationic lipid may be dissolved directly in the oil.

The cationic emulsions of the invention can be used to deliver a negatively charged molecule, such as a nucleic acid (e.g., RNA). The compositions may be administered to a subject in need thereof to generate or potentiate an immune response. The compositions can also be co-delivered with another immunogenic molecule, immunogenic composition or vaccine to enhance the effectiveness of the induced immune response.

2. Definitions

As used herein, the singular forms "a," "an" and "the" include plural references unless the content clearly dictates otherwise.

The term "about", as used here, refers to +/−10% of a value.

The term "surfactant" is a term of art and generally refers to any molecule having both a hydrophilic group (e.g., a polar group), which energetically prefers solvation by water, and a hydrophobic group which is not well solvated by water. The term "nonionic surfactant" is a known term in the art and generally refers to a surfactant molecule whose hydrophilic group (e.g., polar group) is not electrostatically charged.

The term "polymer" refers to a molecule consisting of individual chemical moieties, which may be the same or different, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. Exemplary polymers include, e.g., poloxamers. Poloxamers are nonionic triblock copolymers having a central hydrophobic chain of polyoxypropylene (poly(propylene oxide)) flanked by two hydrophilic chains of polyoxyethylene (poly(ethylene oxide)).

A "buffer" refers to an aqueous solution that resists changes in the pH of the solution.

As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate.

As use herein, "saccharide" encompasses monosaccharides, oligosaccharides, or polysaccharides in straight chain or ring forms, or a combination thereof to form a saccharide chain. Oligosaccharides are saccharides having two or more monosaccharide residues. Examples of saccharides include glucose, maltose, maltotriose, maltotetraose, sucrose and trehalose.

The terms "self-replicating RNA," "RNA replicon" or "RNA vector" is a term of art and generally refer to an RNA molecule which is capable of directing its own amplification or self-replication in vivo, typically within a target cell. The RNA replicon is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently. An alphavirus-derived self-replicating RNA may contain the following elements in sequential order: 5' viral sequences required in cis for replication (also referred to as 5' CSE, in background), sequences which, when expressed, code for biologically active alphavirus nonstructural proteins (e.g., nsP1, nsP2, nsP3, nsP4), 3' viral sequences required in cis for replication (also referred to as 3' CSE, in background), and a polyadenylate tract. The alphavirus-derived self-replicating RNA may also contain a viral subgenomic "junction region" promoter, sequences from one or more structural protein genes or portions thereof, extraneous nucleic acid molecule(s) which are of a size sufficient to allow production of recombinant alphavirus particles, as well as heterologous sequence(s) to be expressed.

The term "adjuvant" refers to any substance that assists or modifies the action of a pharmaceutical, including but not limited to immunological adjuvants, which increase and/or diversify the immune response to an antigen. Hence, immunological adjuvants include compounds that are capable of potentiating an immune response to antigens. Immunological adjuvants can potentiate humoral and/or cellular immunity. Substances that stimulate an innate immune response are included within the definition of immunological adjuvants herein. Immunological adjuvants may also be referred to as "immunopotentiators."

As used herein, an "antigen" or "immunogen" refers to a molecule containing one or more epitopes (e.g., linear, conformational or both) that elicit an immunological response. As used herein, an "epitope" is that portion of given species (e.g., an antigenic molecule or antigenic complex) that determines its immunological specificity. An epitope is within the scope of the present definition of antigen. The term "antigen" or "immunogen" as used herein includes subunit antigens, i.e., antigens which are separate and discrete from a whole organism with which the antigen is associated in nature. Antibodies such as anti-idiotype antibodies, or fragments thereof, and synthetic peptide mimotopes, which can mimic an antigen or antigenic determinant, are also captured under the definition of antigen as used herein.

An "immunological response" or "immune response" is the development in a subject of a humoral and/or a cellular immune response to an antigen or an immunological adjuvant.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be used as immunogenic molecule in various embodiments of the invention) include the following: TLR1 (bacterial lipoproteins from Mycobacteria, Neisseria), TLR2 (zymosan yeast particles, peptidoglycan, lipoproteins, lipopeptides, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, Nature Medicine 11, S63-S68 (2005), K. S. Rosenthal and D. H. Zimmerman, Clinical and Vaccine Immunology, 13(8), 821-829 (2006), and the references cited therein.

For purposes of the present invention, a humoral immune response refers to an immune response mediated by antibody molecules, while a cellular immune response is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) J. Immunol 151:4189-4199; Doe et al. (1994) Eur. J. Immunol 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined using standard immunoassays and neutralization assays, well known in the art.

Compositions in accordance with the present invention display "enhanced immunogenicity" for a given antigen when they possess a greater capacity to elicit an immune response than the immune response elicited by an equivalent amount of the antigen in a differing composition (e.g., wherein the antigen is administered as a soluble protein). Thus, a composition may display enhanced immunogenicity, for example, because the composition generates a stronger immune response, or because a lower dose or fewer doses of antigen is necessary to achieve an immune response in the subject to which it is administered. Such enhanced immunogenicity can be determined, for example, by administering a composition of the invention and an antigen control to animals and comparing assay results of the two.

3. Cationic Oil-in-Water Emulsions

The cationic oil-in-water emulsions disclosed herein are generally described in the manner that is conventional in the art, by concentrations of components that are used to prepare the emulsions. It is understood in the art that during the process of producing emulsions, including sterilization and other downstream processes, small amounts of oil (e.g., squalene), cationic lipid (e.g., DOTAP), or other components may be lost, and the actual concentrations of these components in the final product (e.g., a packaged, sterilized emulsion that is ready for administration) might be slightly lower than starting amounts, sometimes by up to about 10% or by up to about 20%.

This invention generally relates to cationic oil-in-water emulsions that can be used to deliver negatively charged molecules, such as an RNA molecule. The emulsion particles comprise an oil core and a cationic lipid. The cationic lipid can interact with the negatively charged molecule, for example through electrostatic forces and hydrophobic/hydrophilic interactions, thereby anchoring the molecule to the emulsion particles. The cationic emulsions described herein are particularly suitable for delivering a negatively charged molecule, such as an RNA molecule encoding an antigen or small interfering RNA to cells in vivo. For example, the cationic emulsions described herein provide advantages for delivering RNA that encode antigens, including self-replicating RNAs, as vaccines.

The particles of the oil-in-water emulsions resemble a micelle with a central core of oil. The oil core is coated with the cationic lipid, which disperses the oil droplet in the aqueous (continuous) phase as micelle-like droplets. One or more optional components may be present in the emulsion, such as surfactants and/or phospholipids as described below. For example, one or more surfactants may be used to promote particle formation and/or to stabilize the emulsion particles. In that case, the oil core is coated with the cationic lipid as well as the surfactant(s) to form micelle-like droplets. Similarly, one or more lipids (e.g., neutral lipids, glycol-lipids or phospholipids) may also be present on the surface of the emulsion particles, if such lipids are used as emulsifiers to disperse the oil droplets.

The particles of the oil-in-water emulsions have an average diameter (i.e., the number average diameter) of 1 micrometer or less. It is particularly desirable that the average particle size (i.e., the number average diameter) of the cationic emulsions is about 900 nm or less, about 800 nm or less, about 700 nm or less, about 600 nm or less, about 500 nm or less, about 400 nm or less, 300 nm or less, or 200 nm or less, for example, from about 1 nm to about 1 µm, from about 1 nm to about 900 nm, from about 1 nm to about 800 nm, from about 1 nm to about 700 nm, from about 1 nm to about 600 nm, from about 1 nm to about 500 nm, from about 1 nm to about 400 nm, from about 1 nm to about 300 nm, from about 1 nm to about 200 nm, from about 1 nm to about 175 nm, from about 1 nm to about 150 nm, from about 1 nm to about 125 nm, from about 1 nm to about 100 nm, from about 1 nm to about 75 nm, or from about 1 nm to about 50 nm.

It is particularly desirable that the average particle diameter of the cationic emulsions is about 180 nm or less, about 170 nm or less, about 160 nm or less, about 150 nm or less, about 140 nm or less, about 130 nm or less, about 120 nm or less, about 110 nm or less, or about 100 nm or less; for example, from about 80 nm to 180 nm, from about 80 nm to 170 nm, from about 80 nm to 160 nm, from about 80 nm to 150 nm, from about 80 nm to 140 nm, from about 80 nm to 130 nm, from about 80 nm to 120 nm; from about 80 nm to 110 nm, or from about 80 nm to 100 nm. Particularly preferred average particle diameter is about 100 nm.

The size of the emulsion particles can be varied by changing the ratio of surfactant to oil (increasing the ratio decreases droplet size), operating pressure of homogenization (increasing operating pressure of homogenization typically reduces droplet size), temperature (increasing temperature decreases droplet size), changing the type of oil, and other process parameters, as described in detail below. Inclusion of certain types of buffers in the aqueous phase may also affect the particle size.

In some cases, in the context of an RNA vaccine, the size of the emulsion particles may affect the immunogenicity of the RNA-emulsion complex. Therefore, the preferred range of the average particle size for emulsions should be from about 80 nm to about 180 nm in diameter.

The emulsion particles described herein can be complexed with a negatively charged molecule. Prior to complexation with the negatively charged molecule, the overall net charge of the particles (typically measured as zeta-potential) should be positive (cationic). The overall net charge of the particles may vary, depending on the type of the cationic lipid and the amount of the cationic lipid in the emulsion, the amount of oil in the emulsion (e.g. higher percentage of oil typically results in less charge on the surface of the particles), and may also be affected by any additional component (e.g., surfactant(s) and/or phospholipid(s)) that is present in the emulsion. In the exemplary embodiments, the zeta-potential of the pre-complexation particles are typically above 10 mV.

Preferably, the zeta-potential of the pre-complexation particles are no more than about 50 mV, no more than about 45 mV, no more than about 40 mV, no more than about 35 mV, no more than about 30 mV, no more than about 25 mV, no more than about 20 mV; from about 5 mV to about 50 mV, from about 10 mV to about 50 mV, from about 10 mV to about 45 mV, from about 10 mV to about 40 mV, from about 10 mV to about 35 mV, from about 10 mV to about 30 mV, from about 10 mV to about 25 mV, or from about 10 mV to about 20 mV. Zeta potential can be affected by (i) pH of the emulsion, (ii) conductivity of the emulsion (e.g., salinity), and (iii) the concentration of the various components of the emulsion (polymer, non-ionic surfactants etc.). Zeta potential of CNEs is measured using a Malvern Nanoseries Zetasizer (Westborough, Mass.). The sample is diluted 1:100 in water (viscosity: 0.8872cp, RI: 1.330, Dielectric constant: 78.5) and is added to a polystyrene latex capillary cell (Malvern, Westborough, Mass.). Zeta potential is measured at 25° C. with a 2 minute equilibration time and analyzed using the Smoluchowski model (F(Ka) value=1.5). Data is reported in mV.

An exemplary cationic emulsion of the invention is CNE17. The oil core of CNE17 is squalene (at 4.3% w/v) and the cationic lipid is DOTAP (at 1.4 mg/mL). CNE17 also includes the surfactants SPAN85 ((sorbtian trioleate) at 0.5% v/v) and Tween 80 ((polysorbate 80; polyoxyethylenesorbitan monooleate) at 0.5% v/v). Thus, the particles of CNE17 comprise a squalene core coated with SPAN85, Tween80, and DOTAP. RNA molecules were shown to complex with CNE17 particles efficiently at 4:1 N/P ratio and 10:1 N/P ratio. Other exemplary cationic emulsions include, e.g., CNE05 (0.5% w/v squalene, 0.08% Tween 80, and 1.2 mg/mL DOTAP), CNE12 (4.3% squalene, 0.5% SPAN85, 0.5% Tween 80, and 2.46 mg/mL DC Cholesterol), CNE13 (4.3% squalene, 0.5% SPAN85, 0.5% Tween 80, and 1.45 mg/mL DDA), and other emulsions described herein.

The individual components of the oil-in-water emulsions of the present invention are known in the art, although such compositions have not been combined in the manner described herein. Accordingly, the individual components, although described below both generally and in some-detail for preferred embodiments, are well known in the art, and the terms used herein, such as oil core, surfactant, phospholipids, etc., are sufficiently well known to one skilled in the art without further description. In addition, while preferred ranges of the amount of the individual components of the emulsions are provided, the actual ratios of the components of a particular emulsion may need to be adjusted such that emulsion particles of desired size and physical property can be properly formed. For example, if a particular amount of oil is used (e.g. 5% v/v oil), then, the amount of surfactant should be at level that is sufficient to disperse the oil droplet into aqueous phase to form a stable emulsion. The actual amount of surfactant required to disperse the oil droplet into aqueous phase depends on the type of surfactant and the type of oil core used for the emulsion; and the amount of oil may also vary according to droplet size (as this changes the surface area between the two phases). The actual amounts and the relative proportions of the components of a desired emulsion can be readily determined by a skilled artisan.

A. Oil Core

The particles of the cationic oil-in-water emulsions comprise an oil core. Preferably, the oil is a metabolizable, non-toxic oil; more preferably one of about 6 to about 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil that can be metabolized by the body of the subject to which the emulsion will be administered, and is not toxic to the subject. The subject may be an animal, typically a mammal, and preferably a human.

In certain embodiments, the oil core is in liquid phase at 25° C. The oil core is in liquid phase at 25° C., when it displays the properties of a fluid (as distinguished from solid and gas; and having a definite volume but no definite shape) when stored at 25° C. The emulsion, however, may be stored and used at any suitable temperature. Preferably, the oil core is in liquid phase at 4° C.

The oil may be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will generally have from about 6 to about 30 carbon atoms. The moiety may have a straight or branched chain structure. It may be fully saturated or have one or more double or triple bonds. Where mono or poly ester- or ether-based oils are employed, the limitation of about 6 to about 30 carbons applies to the individual fatty acid or fatty alcohol moieties, not the total carbon count.

It is particularly desirable that the oil can be metabolized by the host to which the emulsion is administered.

Any suitable oils from an animal, fish or vegetable source may be used. Sources for vegetable oils include nuts, seeds and grains, and suitable oils peanut oil, soybean oil, coconut oil, and olive oil and the like. Other suitable seed oils include safflower oil, cottonseed oil, sunflower seed oil, sesame seed oil and the like. In the grain group, corn oil, and the oil of other cereal grains such as wheat, oats, rye, rice, teff, triticale and the like may also be used. The technology for obtaining vegetable oils is well developed and well known. The compositions of these and other similar oils may be found in, for example, the Merck Index, and source materials on foods, nutrition and food technology.

About six to about ten carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEES from PVO International, Inc., Chemical Specialties Division, 416 Division Street, Boongon, N.J. and others.

Animal oils and fats are often in solid phase at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene (2,6,10,15,19,23-hexamethyl-2,6,10,14,18,22-tetracosa-hexaene), a branched, unsaturated terpenoid, is particularly preferred herein. A major source of squalene is shark liver oil, although plant oils (primarily vegetable oils), including amaranth seed, rice bran, wheat germ, and olive oils, are also suitable sources. Squalane, the saturated analog to squalene, is also preferred. Fish oils, including squalene and squalane, are readily available from commercial sources or may be obtained by methods known in the art.

In certain embodiments, the oil core comprises an oil that is selected from the group consisting of: Castor oil, Coconut oil, Corn oil, Cottonseed oil, Evening primrose oil, Fish oil, *Jojoba* oil, Lard oil, Linseed oil, Olive oil, Peanut oil, Safflower oil, Sesame oil, Soybean oil, Squalene, Sunflower oil, Wheatgerm oil, and Mineral oil. In exemplary embodiments, the oil core comprises Soybean oil, Sunflower oil, Olive oil, Squalene, or a combination thereof. Squalane can also be used as the oil. In exemplary embodiments, the oil core comprises Squalene, Squalane, or a combination thereof.

The oil component of the emulsion may be present in an amount from about 0.2% to about 20% (v/v). For example, the cationic oil-in-water emulsion may comprise from about 0.2% to about 20% (v/v) oil, from about 0.2% to about 15% (v/v) oil, from about 0.2% to about 10% (v/v) oil, from about 0.2% to about 9% (v/v) oil, from about 0.2% to about 8% (v/v) oil, from about 0.2% to about 7% (v/v) oil, from about 0.2% to about 6% (v/v) oil, from about 0.2% to about 5% (v/v) oil, from about 0.2% to about 4.3% (v/v) oil, from about 0.3% to about 20% (v/v) oil, from about 0.4% to about 20% (v/v) oil, from about 0.5% to about 20% (v/v) oil, from about 1% to about 20% (v/v) oil, from about 2% to about 20% (v/v) oil, from about 3% to about 20% (v/v) oil, from about 4% to about 20% (v/v) oil, from about 4.3% to about 20% (v/v) oil, from about 5% to about 20% (v/v) oil, about 0.5% (v/v) oil, about 1% (v/v) oil, about 1.5% (v/v) oil, about 2% (v/v) oil, about 2.5% (v/v) oil, about 3% (v/v) oil, about 3.5% (v/v) oil, about 4% (v/v) oil, about 4.3% (v/v) oil, about 5% (v/v) oil, or about 10% (v/v) oil.

Alternativley, the cationic oil-in-water emulsion may comprise from about 0.2% to about 10% (w/v) oil, from about 0.2% to about 9% (w/v) oil, from about 0.2% to about 8% (w/v) oil, from about 0.2% to about 7% (w/v) oil, from about 0.2% to about 6% (w/v) oil, from about 0.2% to about 5% (w/v) oil, from about 0.2% to about 4.3% (w/v) oil, or about 4.3% (w/v) oil.

In an exemplary embodiment, the cationic oil-in-water emulsion comprises about 0.5% (v/v) oil. In another exemplary embodiment, the cationic oil-in-water emulsion comprises about 4.3% (v/v) oil. In another exemplary embodiment, the cationic oil-in-water emulsion comprises about 5% (v/v) oil. In another exemplary embodiment, the cationic oil-in-water emulsion comprises about 4.3% (w/v) squalene.

As noted above, the percentage of oil described above is determined based on the initial amount of the oil that is used to prepare the emulsions. It is understood in the art that the actual concentration of the oil in the final product (e.g., a packaged, sterilized emulsion that is ready for administration) might be slightly lower, sometimes up to about 10% or about 20%.

B. Cationic Lipids

The emulsion particles described herein comprise a cationic lipid, which can interact with the negatively charged molecule thereby anchoring the molecule to the emulsion particles.

Any suitable cationic lipid may be used. Generally, the cationic lipid contains a nitrogen atom that is positively charged under physiological conditions. Suitable cationic lipids include, benzalkonium chloride (BAK), benzethonium chloride, cetrimide (which contains tetradecyltrimethylammonium bromide and possibly small amounts of dodecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethyl-ammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α dioleoylphosphatidylethanolamine, cholesterol hemi succinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol, including but not limited to cholesteryl-3 β-oxysuccinamidoethylenetrimethylammonium salt, cholesteryl-3 β-oxysuccinamidoethylenedimethylamine, cholesteryl-3 β-carboxyamidoethylenetrimethylammonium salt, cholesteryl-3 β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio)propane (DOTAP), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), and combination thereof.

Other cationic lipids suitable for use in the invention include, e.g., the cationic lipids described in U.S. Patent Publications 2008/0085870 (published Apr. 10, 2008) and 2008/0057080 (published Mar. 6, 2008).

Other cationic lipids suitable for use in the invention include, e.g., Lipids E0001-E0118 or E0119-E0180 as disclosed in Table 6 (pages 112-139) of WO 2011/076807 (which also discloses methods of making, and method of using these cationic lipids). Additional suitable cationic lipids include N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA).

The emulsion may comprise any combination of two or more of the cationic lipids described herein.

In preferred embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), Lipids E0001-E0118 or E0119-E0180 as disclosed in Table 6 (pages 112-139) of WO 2011/076807, and combinations thereof.

In other preferred embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), Lipids E0001-E0118 or E0119-E0180 as disclosed in Table 6 (pages 112-139) of WO 2011/076807, and combinations thereof.

In certain embodiments, the cationic lipid is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc.

In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc.

In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml.

In an exemplary embodiment, the cationic oil-in-water emulsion comprises from about 0.73 mg/ml to about 1.45 mg/ml DDA, such as 1.45 mg/ml.

In certain embodiments, the cationic lipid is DOTMA. The cationic oil-in-water emulsion may comprise from about 0.5 mg/ml to about 25 mg/ml DOTMA. For example, the cationic oil-in-water emulsion may comprise DOTMA at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.35 mg/ml, about 1.4 mg/ml, about 1.5 mg/ml, about 1.6 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DOTMA, such as 0.8 mg/ml, 1.2 mg/ml, 1.4 mg/ml or 1.6 mg/ml.

In certain embodiments, the cationic lipid is DOEPC. The cationic oil-in-water emulsion may comprise from about 0.5 mg/ml to about 25 mg/ml DOEPC. For example, the cationic oil-in-water emulsion may comprise DOEPC at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.8 mg/ml DOEPC, such as 0.8 mg/ml, 1.2 mg/ml, 1.4 mg/ml, 1.6 mg/ml, 1.7 mg/ml, or 1.8 mg/ml.

In certain embodiments, the cationic lipid is DSTAP. The cationic oil-in-water emulsion may comprise from about 0.5 mg/ml to about 50 mg/ml DSTAP. For example, the cationic oil-in-water emulsion may comprise DSTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DSTAP, such as 0.8 mg/ml, 1.2 mg/ml, 1.4 mg/ml or 1.6 mg/ml.

In certain embodiments, the cationic lipid is DODAC. The cationic oil-in-water emulsion may comprise from about 0.5 mg/ml to about 50 mg/ml DODAC. For example, the cationic oil-in-water emulsion may comprise DODAC at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.15 mg/ml, about 1.16 mg/ml, about 1.17 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from 0.73 mg/ml to about 1.45 mg/ml DODAC, such as 1.45 mg/ml.

In certain embodiments, the cationic lipid is DODAP. The cationic oil-in-water emulsion may comprise from about 0.5 mg/ml to about 50 mg/ml DODAP. For example, the cationic oil-in-water emulsion may comprise DODAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DODAP, such as 0.8 mg/ml, 1.2 mg/ml, 1.4 mg/ml or 1.6 mg/ml.

In some cases, it may be desirable to use a cationic lipid that is soluble in the oil core. For example, DOTAP DOEPC, DODAC, and DOTMA are soluble in squalene or squalane.

In other cases, it may be desirable to use a cationic lipid that is not soluble in the oil core. For example, DDA and DSTAP is not soluble in squalene. It is within the knowledge in the art to determine whether a particular lipid is soluble or insoluble in the oil and choose an appropriate oil and lipid combination accordingly. For example, solubility can be predicted based on the structures of the lipid and oil (e.g., the solubility of a lipid may be determined by the structure of its tail). For example, lipids having one or two unsaturated fatty acid chains (e.g., oleoyl tails), such as DOTAP, DOEPC, DODAC, DOTMA, are soluble in squalene or squalane; whereas lipids having saturated fatty acid chains (e.g., stearoyl tails) are not soluble in squalene. Alternatively, solubility can be determined according to the quantity of the lipid that dissolves in a given quantity of the oil to form a saturated solution).

As noted above, the concentration of a lipid described above is determined based on the initial amount of the lipid that is used to prepare the emulsions. It is understood in the art that the actual concentration of the oil in the final product (e.g., a packaged, sterilized emulsion that is ready for administration) might be slightly lower, sometimes by up to about 20%.

C. Additional Components

The cationic oil-in-water emulsions described herein may further comprise additional components. For example, the emulsions may comprise components that can promote particle formation, improve the complexation between the negatively charged molecules and the cationic particles, or increase the stability of the negatively charged molecule (e.g., to prevent degradation of an RNA molecule).

Surfactants

In certain embodiments, the particles of the cationic oil-in-water emulsion further comprise a surfactant.

A substantial number of surfactants have been used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form a third substantial group of emulsifying and suspending agents which could be used in this invention.

Specific examples of suitable surfactants include the following:

1. Water-soluble soaps, such as the sodium, potassium, ammonium and alkanol-ammonium salts of higher fatty acids ($C_{10}$-$C_{22}$), in particular sodium and potassium tallow and coconut soaps.

2. Anionic synthetic non-soap surfactants, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$-$C_{24}$ α-olefins.

3. Nonionic synthetic surfactants made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic surfactants, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263, issued Feb. 14, 1967, and include dimethyldodecylphosphine oxide and dimethyl-(2hydroxydodecyl) phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.

6. Ampholytic synthetic surfactants, such as sodium 3-dodecylaminopropionate and sodium 3-dodecylaminopropane sulfonate.

7. Zwitterionic synthetic surfactants, such as 3-(N,N-dimethyl-N-hexadecylammonio)propane-1-sulfonate and 3-(N,N-dimethyl-N-hexadecylammonio)-2-hydroxy propane-1-sulfonate.

Additionally, all of the following types of surfactants can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number of surfactants specifically designed for and commonly used in biological situations. Such surfactants are divided into four basic types: anionic, cationic, zwitterionic (amphoteric), and nonionic. Exemplary anionic surfactants include, e.g., perfluorooctanoate (PFOA or PFO), perfluorooctanesulfonate (PFOS), alkyl sulfate salts such as sodium dodecyl sulfate (SDS) or ammonium lauryl sulfate, sodium laureth sulfate (also known as sodium lauryl ether sulfate, SLES), alkyl benzene sulfonate, and fatty acid salts. Exemplary cationic surfactants include, e.g., alkyltrimethylammonium salts such as cetyl trimethylammonium bromide (CTAB, or hexadecyl trimethyl ammonium bromide), cetylpyridinium chloride (CPC), polyethoxylated tallow amine (POEA), benzalkonium chloride (BAC), benzethonium chloride (BZT). Exemplary zwitterionic (amphoteric) surfactants include, e.g., dodecyl betaine, cocamidopropyl betaine, and coco ampho glycinate. Exemplary nonionic surfactants include, e.g., alkyl poly(ethylene oxide), alkylphenol poly(ethylene oxide), copolymers of poly(ethylene oxide) and poly(propylene oxide) (commercially called poloxamers or poloxamines), Aayl polyglucosides (e.g., octyl glucoside or decyl maltoside), fatty alcohols (e.g., cetyl alcohol or oleyl alcohol), cocamide MEA, cocamide DEA, Pluronic® F-68 (polyoxyethylene-polyoxypropylene block copolymer), and polysorbates, such as Tween 20 (polysorbate 20), Tween 80 (polysorbate 80; polyoxyethylenesorbitan monooleate), dodecyl dimethylamine oxide, and vitamin E tocopherol propylene glycol succinate (Vitamin E TPGS).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available.

A related group of surfactants comprises olyoxyethylene sorbitan monoesters and olyoxyethylene sorbitan triesters. These materials are prepared by addition of ethylene oxide to a 1,4-sorbitan monester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monester or triester surfactants to promote emulsion stability. TWEEN® surfactants generally have a HLB value falling between 9.6 to 16.7. TWEEN® surfactants are commercially available.

A third group of non-ionic surfactants which could be used alone or in conjunction with SPANS, ARLACEL® and TWEENS surfactants are the polyoxyethylene fatty acids made by the reaction of ethylene oxide with a long-chain fatty acid. The most commonly available surfactant of this type is solid under the name MYRJS and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from commercial sources.

Other non-ionic surfactants which could potentially be used are, for example, polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene fatty acid, alcohol or ether derivatives of long-chain fatty acids of 12-22 carbon atoms.

As the emulsions and formulations of the invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

In certain embodiments, the emulsion comprises a single non-ionic surfactant, most particularly a TWEEN® surfactant, as the emulsion stabilizing non-ionic surfactant. In an exemplary embodiment, the emulsion comprises TWEEN® 80, otherwise known as polysorbate 80 or polyoxyethylene 20 sorbitan monooleate. In other embodiments, the emulsion comprises two or more non-ionic surfactants, in particular a TWEEN® surfactant and a SPAN® surfactant. In an exemplary embodiment, the emulsion comprises TWEEN® 80 and SPAN®85.

The oil-in-water emulsions can contain from about 0.01% to about 2.5% surfactant (v/v or w/v), about 0.01% to about 2% surfactant, 0.01% to about 1.5% surfactant, 0.01% to about 1% surfactant, 0.01% to about 0.5% surfactant, 0.05% to about 0.5% surfactant, 0.08% to about 0.5% surfactant, about 0.08% surfactant, about 0.1% surfactant, about 0.2% surfactant, about 0.3% surfactant, about 0.4% surfactant, about 0.5% surfactant, about 0.6% surfactant, about 0.7% surfactant, about 0.8% surfactant, about 0.9% surfactant, or about 1% surfactant.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% Tween 80 (polysorbate 80; polyoxyethylenesorbitan monooleate).

In an exemplary embodiment, the oil-in-water emulsion contains 0.08% Tween 80.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% SPAN85 (sorbtian trioleate).

Alternatively or in addition, the oil-in-water emulsions can contain a combination of surfactants described herein. For example, a combination of Tween 80 (polysorbate 80; polyoxyethylenesorbitan monooleate) and SPAN85 (sorbtian trioleate) may be used. The emulsions may contain various amounts Tween 80 and SPAN85 (e.g., those exemplified above), including equal amounts of these surfactants. For example, the oil-in-water emulsions can contain about 0.05% Tween 80 and about 0.05% SPAN85, about 0.1% Tween 80 and about 0.1% SPAN85, about 0.2% Tween 80 and about 0.2% SPAN85, about 0.3% Tween 80 and about 0.3% SPAN85, about 0.4% Tween 80 and about 0.4% SPAN85, about 0.5% Tween 80 and about 0.5% SPAN85, about 0.6% Tween 80 and about 0.6% SPAN85, about 0.7% Tween 80 and about 0.7% SPAN85, about 0.8% Tween 80 and about 0.8% SPAN85, about 0.9% Tween 80 and about 0.9% SPAN85, or about 1% Tween 80 and about 1.0% SPAN85.

Polyethylene Glycol (PEG)-lipids, such as PEG coupled to dialkyloxypropyls (PEG-DAA), PEG coupled to diacylglycerol (PEG-DAG), PEG coupled to phosphatidylethanolamine (PE) (PEG-PE) or some other phospholipids (PEG-phospholipids), PEG conjugated to ceramides (PEG-Cer), or a combination thereof, may also be used as surfactants (see, e.g., U.S. Pat. No. 5,885,613; U.S. patent application publication Nos. 2003/0077829, 2005/0175682 and 2006/0025366). Other suitable PEG-lipids include, e.g., PEG-dialkyloxypropyl (DAA) lipids or PEG-diacylglycerol (DAG) lipids. Exemplary PEG-DAG lipids include, e.g., PEG-dilauroylglycerol ($C_{12}$) lipids, PEG-dimyristoylglycerol ($C_{14}$) lipids, PEG-dipalmitoylglycerol ($C_{16}$) lipids, or PEG-di stearoylglycerol ($C_{18}$) lipids. Exemplary PEG-DAA lipids include, e.g., PEG-dilauryloxypropyl ($C_{12}$) lipids, PEG-dimyristyloxypropyl ($C_{14}$) lipids, PEG-dipalmityloxypropyl ($C_{16}$) lipids, or PEG-distearyloxypropyl ($C_{18}$) lipids.

PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. as well as other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-$CH_2COOH$), is particularly useful for preparing the PEG-lipid conjugates including, e.g., PEG-DAA conjugates.

Preferably, the PEG has an average molecular weight of from about 1000 to about 5000 daltons (e.g., $PEG_{1000}$, $PEG_{2000}$, $PEG_{3000}$, $PEG_{4000}$, $PEG_{5000}$). The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties In exemplary embodiments, $PEG_{2000}PE$, $PEG_{5000}PE$, $PEG_{1000}DMG$, $PEG_{2000}DMG$, $PEG_{3000}DMG$, or a combination thereof, is used as a surfactant. In certain exemplary embodiments, the oil-in-water emulsion contains from about 1 mg/ml to about 80 mg/ml $PEG_{2000}PE$, $PEG_{5000}PE$, $PEG_{1000}DMG$, $PEG_{2000}DMG$, or $PEG_{3000}DMG$.

Phospholipids

In certain embodiments, the particles of the cationic oil-in-water emulsion further comprise a phospholipid.

Phospholipids are esters of fatty acids in which the alcohol component of the molecule contains a phosphate group. Phospholipids include glycerophosphatides (containing glycerol) and the sphingomyelins (containing sphingosine). Exemplary phospholipids include phosphatidylcholine, phosphatidylethanolamine, phosphatidylserine and sphingomyelin; and synthetic phospholipids comprising dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine, and dipalmitoyl serine.

The following exemplary phopholipids may be used.

| | |
|---|---|
| DDPC | 1,2-Didecanoyl-sn-Glycero-3-phosphatidylcholine |
| DEPA-NA | 1,2-Dierucoyl-sn-Glycero-3-Phosphate(Sodium Salt) |
| DEPC | 1,2-Erucoyl-sn-Glycero-3-phosphatidylcholine |
| DEPE | 1,2-Dierucoyl-sn-Glycero-3-phosphatidylethanolamine |
| DEPG-NA | 1,2-Dierucoyl-sn-Glycero-3[Phosphatidyl-rac-(1-glycerol. . .) |
| DLOPC | 1,2-Linoleoyl-sn-Glycero-3-phosphatidylcholine |
| DLPA-NA | 1,2-Dilauroyl-sn-Glycero-3-Phosphate(Sodium Salt) |
| DLPC | 1,2-Dilauroyl-sn-Glycero-3-phosphatidylcholine |
| DLPE | 1,2-Dilauroyl-sn-Glycero-3-phosphatidylethanolamine |
| DLPG-NA | 1,2-Dilauroyl-sn-Glycero-3[Phosphatidyl-rac-( 1-glycerol. . .) (Sodium Salt) |
| DLPG-NH4 | 1,2-Dilauroyl-sn-Glycero-3[Phosphatidyl-rac-(1-glycerol . . .) |
| DLPS-NA | 1,2-Dilauroyl-sn-Glycero-3-phosphatidylserine(Sodium Salt) |
| DMPA-NA | 1,2-Diimyristoyl-sn-Glycero-3-Phosphate(Sodium Salt) |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG-NA | 1,2-Myristoyl-sn-Glycero-3[Phosphatidyl-rac-(1-glycerol. . .) |
| DMPG-NH4 | 1,2-Myristoyl-sn-Glycero-3[Phosphatidyl-rac-(1-glycerol. . .) |
| DMPG-NH4/NA | 1,2-Myristoyl-sn-Glycero-3[Phosphatidyl-rac-(1-glycerol. . .) |
| DMPS-NA | 1,2-Dimyristoyl-sn-Glycero-3-phosphatidylserine(Sodium Salt) |
| DOPA-NA | 1,2-Dioleoyl-sn-Glycero-3-Phosphate(Sodium Salt) |
| DOPC | 1,2-Dioleoyl-sn-Glycero-3-phosphatidylcholine |
| DOPE | 1,2-Dioleoyl-sn-Glycero-3-phosphatidylethanolamine |
| DOPG-NA | 1,2-Dioleoyl-sn-Glycero-3[Phosphatidyl-rac-(1-glycerol. . .) |
| DOPS-NA | 1,2-Dioleoyl-sn-Glycero-3-phosphatidylserine(Sodium Salt) |
| DPPA-NA | 1,2-Dipalmitoyl-sn-Glycero-3-Phosphate(Sodium Salt) |
| DPPC | 1,2-Dipalmitoyl-sn-Glycero-3-phosphatidylcholine |
| DPPE | 1,2-Dipalmitoyl-sn-Glycero-3-phosphatidylethanolamine |

| | |
|---|---|
| DPPG-NA | 1,2-Dipalmitoyl-sn-Glycero-3[Phosphatidyl-rac-(1-glycerol. . .) |
| DPPG-NH4 | 1,2-Dipalmitoyl-sn-Glycero-3[Phosphatidyl-rac-(1-glycerol. . .) |
| DPPS-NA | 1,2-Dipalmitoyl-sn-Glycero-3-phosphatidylserine(Sodium Salt) |
| DPyPE | 1,2-diphytanoyl-sn-glycero-3-phosphoethanolamine |
| DSPA-NA | 1,2-Distearoyl-sn-Glycero-3-Phosphate(Sodium Salt) |
| DSPC | 1,2-Distearoyl-sn-Glycero-3-phosphatidylcholine |
| DSPE | 1,2-Diostearpyl-sn-Glycero-3-phosphatidylethanolamine |
| DSPG-NA | 1,2-Distearoyl-sn-Glycero-3[Phosphatidyl-rac-(1-glycerol. . .) |
| DSPG-NH4 | 1,2-Distearoyl-sn-Glycero-3[Phosphatidyl-rac-(1-glycerol. . .) |
| DSPS-NA | 1,2-Distearoyl-sn-Glycero-3-phosphatidylserine(Sodium Salt) |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin | |
| MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG-NA | 1,2-Dioleoyl-sn-Glycero-3[Phosphatidyl-rac-(1-glycerol). . .](Sodium Salt) |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

In certain embodiments, it may be advantageous to use a neutral lipid. It may also be advantageous to use a phospholipid, including a zwitterionic phospholipid, for example, a phospholipid containing one or more alkyl or alkenyl radicals of about 12 to about 22 carbons in length (e.g., about 12 to about 14, to about 16, to about 18, to about 20, to about 22 carbons), which radicals may contain, for example, from 0 to 1 to 2 to 3 double bonds. It may be advantageous to use a zwitterionic phospholipid.

Preferred phospholipids include, e.g., 1,2-dioleoyl-sn-glycero-3-phosphatidylethanolamine (DOPE), Egg phosphatidylcholine (egg PC), palmitoyl oleoyl phosphatidylcholine (POPC), dimyristoyl phosphatidylcholine (DMPC), dioleoyl phosphatidylcholine (DOPC), DPPC, dipalmitoyl phosphatidylcholine (DPPC), palmitoyl linoleyl phosphatidylcholine (PLPC), DPyPE, or a combination thereof.

In certain embodiments, the phospholipid is DOPE. The cationic oil-in-water emulsion may comprise from about 0.1 mg/ml to about 20 mg/ml DOPE. For example, the cationic oil-in-water emulsion may comprise DOPE at from about 0.5 mg/ml to about 10 mg/ml, from about 0.1 mg/ml to about 10 mg/ml, or from about 1.5 mg/ml to about 7.5 mg/ml DOPE.

In an exemplary embodiment, the cationic oil-in-water emulsion comprises about 1.5 mg/ml DOPE.

In certain embodiments, the phospholipid is egg PC. The cationic oil-in-water emulsion may comprise from about 0.1 mg/ml to about 20 mg/ml egg PC. For example, the cationic oil-in-water emulsion may comprise egg PC at from about 0.1 mg/ml to about 10 mg/ml, from about 1.0 mg/ml to about 10 mg/ml, or from about 1.5 mg/ml to about 3.5 mg/ml egg PC.

In an exemplary embodiment, the cationic oil-in-water emulsion comprises about 1.55 mg/ml egg PC.

In certain embodiments, the phospholipid is DPyPE. The cationic oil-in-water emulsion may comprise from about 0.1 mg/ml to about 20 mg/ml DPyPE. For example, the cationic oil-in-water emulsion may comprise DPyPE at from about 0.1 mg/ml to about 10 mg/ml, from about 1.5 mg/ml to about 10 mg/ml, or from about 1.5 mg/ml to about 5 mg/ml DPyPE.

In an exemplary embodiment, the cationic oil-in-water emulsion comprises about 1.6 mg/ml DPyPE.

In certain embodiments, the emulsion particles may comprise a combination of a surfactant and a phospholipid described herein.

D. Aqueous Phase (Continuous Phase)

The aqueous phase (continuous phase) of the oil-in-water emulsions is a buffered salt solution (e.g., saline) or water. The buffered salt solution is an aqueous solution that comprises a salt (e.g., NaCl), a buffer (e.g., a citrate buffer), and can further comprise an osmolality adjusting agent (e.g., a saccharide), a polymer, a surfactant, or a combination thereof. If the emulsions are formulated for parenteral administration, it is preferable to make up final buffered solutions so that the tonicity, i.e., osmolality is essentially the same as normal physiological fluids in order to prevent prevent undesired post-administration consequences, such as post-administration swelling or rapid absorption of the composition. It is also preferable to buffer the aqueous phase in order to maintain a pH compatible with normal physiological conditions. Also, in certain instances, it may be desirable to maintain the pH at a particular level in order to insure the stability of certain components of the emulsion.

For example, it may be desirable to prepare an emulsion that is isotonic (i.e., the same permeable solute (e.g., salt) concentration as the normal cells of the body and the blood) and isosmotic. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate, magnesium chloride, calcium chloride, etc. Non-ionic tonicifying agents can also be used to control tonicity. A number of non-ionic tonicity modifying agents ordinarily known to those in the art. These are typically carbohydrates of various classifications (see, for example, Voet and Voet (1990) Biochemistry (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents useful in the present invention. Non-ionic tonicity modifying agents can be present at a concentration of from about 0.1% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 6.0-8.0, preferably about 6.2 to about 6.8. In an exemplary embodiment, the buffer is 10 mM citrate buffer with a pH at 6.5. In another exemplary embodiment, the aqueous phase is, or the buffer prepared using, RNase-free water or DEPC treated water. In some cases, high salt in the buffer might interfere with complexation of negatively charged molecule to the emulsion particle therefore is avoided. In other cases, certain amount of salt in the buffer may be included.

In an exemplary embodiment, the buffer is 10 mM citrate buffer with a pH at 6.5. In another exemplary embodiment, the aqueous phase is, or the buffer is prepared using, RNase-free water or DEPC treated water.

The aqueous phase may also comprise additional components such as molecules that change the osmolarity of the aqueous phase or molecules that stabilizes the negatively charged molecule after complexation. Preferably, the osmolarity of the aqueous phase is adjusting using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.), or combinations thereof. If desired, a nonionic polymer (e.g., a poly(alkyl glycol) such as polyethylene glycol, polypropylene glycol, or polybutlyene glycol) or nonionic surfactant can be used.

In some case, unadulterated water may be preferred as the aqueous phase of the emulsion when the emulsion is initially prepared. For example, increasing the salt concentration may make it more difficult to achieve the desirable particle size (e.g., less than about 200 nm).

In certain embodiments, the aqueous phase of the cationic oil-in-water emulsion may further comprise a polymer or a surfactant, or a combination thereof. In an exemplary embodiment, the oil-in-water emulsion contains a poloxamer. Poloxamers are nonionic triblock copolymers having a central hydrophobic chain of polyoxypropylene (poly(propylene oxide)) flanked by two hydrophilic chains of polyoxyethylene (poly(ethylene oxide)). Poloxamers are also known by the trade name Pluronic® polymers. Poloxamer polymers may lead to greater stability and increased RNase resistance of the RNA molecule after RNA complexation.

Alternatively or in addition, the cationic oil-in-water emulsion may comprise from about 0.1% to about 20% (w/v) polymer, or from about 0.05% to about 10% (w/v) polymer. For example, the cationic oil-in-water emulsion may comprise a polymer (e.g., a poloxamer such as Pluronic® F127) at from about 0.1% to about 20% (w/v), from about 0.1% to about 10% (w/v), from about 0.05% to about 10% (w/v), or from about 0.05% to about 5% (w/v).

In an exemplary embodiment, the oil-in-water emulsion comprises about 4% (w/v), or about 8% (w/v) Pluronic® F127.

The quantity of the aqueous component employed in these compositions will be that amount necessary to bring the value of the composition to unity. That is, a quantity of aqueous component sufficient to make 100% will be mixed, with the other components listed above in order to bring the compositions to volume.

4. Negatively Charged Molecules

When a negatively charged molecule is to be delivered, it can be complexed with the particles of the cationic oil-in-water emulsions. The negatively charged molecule is complexed with the emulsion particles by, for example, interactions between the negatively charged molecule and the cationic lipid on the surface of the particles, as well as hydrophobic/hydrophilic interactions between the negatively charged molecule and the surface of the particles. Although not wishing to be bound by any particular theory, it is believed that the negatively charged molecules interact with the cationic lipid through non-covalent, ionic charge interactions (electrostatic forces), and the strength of the complex as well as the amount of negatively charged compound that can be complexed to a particle are related to the amount of cationic lipid in the particle. Additionally, hydrophobic/hydrophilic interactions between the negatively charged molecule and the surface of the particles may also play a role.

Examples of negatively charged molecules include negatively charged peptides, polypeptides or proteins, nucleic acid molecules (e.g., single or double stranded RNA or DNA), small molecules (e.g., small molecule immune potentiators (SMIPs), phosphonate, fluorophosphonate, etc.) and the like. In preferred aspects, the negatively charged molecule is an RNA molecule, such as an RNA that encodes a peptide, polypeptide or protein, including self-replicating RNA molecules, or a small interfering RNA.

The complex can be formed by using techniques known in the art, examples of which are described herein. For example, a nucleic acid-particle complex can be formed by mixing a cationic emulsion with the nucleic acid molecule, for example by vortexing. The amount of the negatively charged molecule and cationic lipid in the emulsions may be adjusted or optimized to provide desired strength of binding and binding capacity.

For example, as described and exampled herein, exemplary RNA-particle complexes were produced by varying the RNA: cationic lipid ratios (as measured by the "N/P ratio"). The term N/P ratio refers to the amount (moles) of protonatable nitrogen atoms in the cationic lipid divided by the amount (moles) of phosphates on the RNA. Preferred N/P ratios are from about 1:1 to about 20:1, from about 2:1 to about 18:1, from about 3:1 to 16:1, from about 4:1 to about 14:1, from about 6:1 to about 12:1, about 3:1, about 4:1, about 5:1, about 6:1, about 7:1, about 8:1, about 9:1, about 10:1, about 11:1, about 12:1, about 13:1, about 14:1, about 15:1, or about 16:1. Alternatively, preferred N/P ratios are at least about 3:1, at least about 4:1, at least about 5:1, at least about 6:1, at least about 7:1, at least about 8:1, at least about 9:1, at least about 10:1, at least about 11:1, at least about 12:1, at least about 13:1, at least about 14:1, at least about 15:1, or at least about 16:1. A more preferred N/P ratio is about 4:1 or higher.

Each emulsion may have its own optimal or preferred N/P ratio to produce desired effects (e.g., desired level of expression of the complexed RNA), which can be determined experimentally (e.g., using the assays as described herein or other techniques known in the art, such as measuring expression level of a protein that is encoded by the RNA, or measuring the percentage of the RNA molecules being released from the complex in the presence of heparin). Generally, the N/P ratio should be at a value that at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the RNA molecules are released from the RNA-particle complexes when the RNA-particle complexes are taken up by cells. An N/P ratio of at least 4:1 is preferred.

The cationic oil-in-water emulsions described herein are particularly suitable for formulating nucleic acid-based vaccines (e.g., DNA vaccines, RNA vaccines). The formation of a nucleic acid-emulsion particle complex facilitates the uptake of the nucleic acid into host cells, and protects the nucleic acid molecule from nuclease degradation. Transfected cells can then express the antigen encoded by the nucleic acid molecule, which can produce an immune response to the antigen. Like live or attenuated viruses, nucleic acid-based vaccines can effectively engage both MHC-I and MHC-II pathways allowing for the induction of $CD8^+$ and $CD4^+$ T cell responses, whereas antigen present in soluble form, such as recombinant protein, generally induces only antibody responses.

The sequence of the RNA molecule may be codon optimized or deoptimized for expression in a desired host, such as a human cell.

In certain embodiments, the negatively charged molecule described herein is an RNA molecule. In certain embodiments, the RNA molecule encodes an antigen (peptide, polypeptide or protein) and the cationic oil in water emulsion is suitable for use as an RNA-based vaccine. The composition can contain more than one RNA molecule encoding an antigen, e.g., two, three, five, or ten RNA molecules that are complexed to the emulsion particles. That is, the composition can contain one or more different species of RNA molecules, each encoding a different antigen. Alternatively or in addition, one RNA molecule may also encode more than one antigen, e.g., a bicistronic, or tricistronic RNA molecule that encodes different or identical antigens. Accordingly, the cationic oil in water emulsion is suitable for use as an RNA-based vaccine, that is monovalent or multivalent.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

If desired, the RNA molecule can comprise one or more modified nucleotides. This can be in addition to any 5' cap structure. There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethy lcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thio-uridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6) alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799 which is incorporated herein by reference.

A RNA used with the invention ideally includes only phosphodiester linkages between nucleosides, but in some embodiments it can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

A. Self-Replicating RNA

In some aspects, the cationic oil in water emulsion contains a self-replicating RNA molecule. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a (+)-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen, or may be transcribed to provide further transcripts with the same sense as the delivered RNA which are translated to provide in situ expression of the antigen. The overall results of this sequence of transcriptions is a huge amplification in the number of the introduced replicon RNAs and so the encoded antigen becomes a major polypeptide product of the cells. Cells transfected with self-replicating RNA briefly produce of antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other non-structural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

One suitable system for achieving self-replication in this manner is to use an alphavirus-based replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), eastern equine encephalitis virus, or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based RNA replicons are typically (+)-stranded RNAs which lead to translation of a replicase (or replicase-transcriptase) after delivery to a cell. The replicase is translated as a polyprotein which auto-cleaves to provide a replication complex which creates genomic (−)-strand copies of the (+)-strand delivered RNA. These (−)-strand transcripts can themselves be transcribed to give further copies of the (+)-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc.

An RNA replicon preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest.

A preferred replicon encodes (i) a RNA-dependent RNA polymerase which can transcribe RNA from the replicon and (ii) an antigen. The polymerase can be an alphavirus replicase e.g. comprising one or more of alphavirus proteins nsP1, nsP2, nsP3 and nsP4. Whereas natural alphavirus genomes encode structural virion proteins in addition to the non-structural replicase polyprotein, it is preferred that the replicon does not encode alphavirus structural proteins. Thus a preferred replicon can lead to the production of genomic RNA copies of itself in a cell, but not to the production of RNA-containing virions. The inability to produce these virions means that, unlike a wild-type alphavirus, the preferred replicon cannot perpetuate itself in infectious form. The alphavirus structural proteins which are necessary for perpetuation in wild-type viruses are absent from the preferred replicon and their place is taken by gene(s) encoding the antigen of interest, such that the subgenomic transcript encodes the antigen rather than the structural alphavirus virion proteins.

A replicon useful with the invention may have two open reading frames. The first (5') open reading frame encodes a replicase; the second (3') open reading frame encodes an antigen. In some embodiments the RNA may have additional (e.g. downstream) open reading frames e.g. to encode additional antigens or to encode accessory polypeptides.

A preferred replicon has a 5' cap (e.g. a 7-methylguanosine), which often can enhance in vivo translation of the RNA. In some embodiments the 5' sequence of the replicon may need to be selected to ensure compatibility with the encoded replicase.

A replicon may have a 3' poly-A tail. It may also include a poly-A polymerase recognition sequence (e.g. AAUAAA) near its 3' end.

Replicons can have various lengths but they are typically 5000-25000 nucleotides long e.g. 8000-15000 nucleotides, or 9000-12000 nucleotides.

The replicon can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the replicon from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such replicons, in general, is described in U.S. Pat. Nos. 5,814,482 and 6,015,686.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA) that have been prepared using modified nucleotides. Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more types of modified nucleotides (e.g., pseudouridine, N6-methyladenosine, 5-methylcytidine, 5-methyluridine).

The self-replicating RNA molecule may encode a single heterologous polypeptide antigen or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast Saccharomyces, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol [90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

B. Antigens

In certain embodiments, the negatively charged molecule described herein is a nucleic acid molecule (e.g., an RNA molecule) that encodes an antigen. Suitable antigens include, but are not limited to, a bacterial antigen, a viral antigen, a fungal antigen, a protazoan antigen, a plant antigen, a cancer antigen, or a combination thereof.

Suitable antigens include proteins and peptides from a pathogen such as a virus, bacteria, fungus, protozoan, plant or from a tumor. Viral antigens and immunogens that can be encoded by the self-replicating RNA molecule include, but are not limited to, proteins and peptides from a Orthomyxoviruses, such as Influenza A, B and C; Paramyxoviridae viruses, such as Pneumoviruses (RSV), Paramyxoviruses (PIV), Metapneumovirus and Morbilliviruses (e.g., measles); Pneumoviruses, such as Respiratory syncytial virus (RSV), Bovine respiratory syncytial virus, Pneumonia virus of mice, and Turkey rhinotracheitis virus; Paramyxoviruses, such as Parainfluenza virus types 1-4 (PIV), Mumps virus, Sendai viruses, Simian virus 5, Bovine parainfluenza virus, Nipahvirus, Henipavirus and Newcastle disease virus; Poxviridae, including a Orthopoxvirus such as *Variola vera* (including but not limited to, *Variola major* and *Variola minor*); Metapneumoviruses, such as human metapneumovirus (hMPV) and avian metapneumoviruses (aMPV); Morbilliviruses, such as Measles; Picornaviruses, such as Enteroviruses, Rhinoviruses, Heparnavirus, Parechovirus, Cardioviruses and Aphthoviruses; Enteroviruseses, such as Poliovirus types 1, 2 or 3, Coxsackie A virus types 1 to 22 and 24, Coxsackie B virus types 1 to 6, Echovirus (ECHO) virus types 1 to 9, 11 to 27 and 29 to 34 and Enterovirus 68 to 71, Bunyaviruses, including a Orthobunyavirus such as California encephalitis virus; a Phlebovirus, such as Rift Valley Fever virus; a Nairovirus, such as Crimean-Congo hemorrhagic fever virus; Heparnaviruses, such as, Hepatitis A virus (HAV); Togaviruses (Rubella), such as a Rubivirus, an Alphavirus, or an Arterivirus; Flaviviruses, such as Tick-borne encephalitis (TBE) virus; Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus; Pestiviruses, such as Bovine viral diarrhea (BVDV), Classical swine fever (CSFV) or Border disease (BDV); Hepadnaviruses, such as Hepatitis B virus, Hepatitis C virus; Rhabdoviruses, such as a Lyssavirus (Rabies virus) and Vesiculovirus (VSV), Caliciviridae, such as Norwalk virus, and Norwalk-like Viruses, such as Hawaii Virus and Snow Mountain Virus; Coronaviruses, such as SARS, Human respiratory coronavirus, Avian infectious bronchitis (IBV), Mouse hepatitis virus (MHV), and Porcine transmissible gastroenteritis virus (TGEV); Retroviruses such as an Oncovirus, a Lentivirus or a Spumavirus; Reoviruses, as an Orthoreovirus, a Rotavirus, an Orbivirus, or a Coltivirus; Parvoviruses, such as Parvovirus B19; Delta hepatitis virus (HDV); Hepatitis E virus (HEV); Hepatitis G virus (HGV); Human Herpesviruses, such as, by way Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8); Papovaviruses, such as Papillomaviruses and Polyomaviruses, Adenoviruess and Arenaviruses.

In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

In some embodiments the antigen elicits an immune response against a parasite from the *Plasmodium* genus, such as *P. falciparum, P. vivax, P. malariae* or *P. ovale*. Thus the invention may be used for immunising against malaria. In some embodiments the antigen elicits an immune response against a parasite from the Caligidae family, particularly those from the *Lepeophtheirus* and *Caligus* genera e.g. sea lice such as *Lepeophtheirus salmonis* or *Caligus rogercresseyi*.

Bacterial antigens and immunogens that can be encoded by the self-replicating RNA molecule include, but are not limited to, proteins and peptides from *Neisseria meningitides, Streptococcus pneumoniae, Streptococcus pyogenes, Moraxella catarrhalis, Bordetella pertussis, Burkholderia* sp. (e.g., *Burkholderia mallei, Burkholderia pseudomallei* and *Burkholderia cepacia*), *Staphylococcus aureus, Staphylococcus epidermis, Haemophilus influenzae, Clostridium tetani* (Tetanus), *Clostridium perfringens, Clostridium botulinums* (Botulism), *Cornynebacterium diphtherias* (Diphtheria), *Pseudomonas aeruginosa, Legionella pneumophila, Coxiella burnetii, Brucella* sp. (e.g., *B. abortus, B. canis, B. melitensis, B. neotomae, B. ovis, B. suis* and *B. pinnipediae*), *Francisella* sp. (e.g., *F. novicida, F. philomiragia* and *F. tularensis*), *Streptococcus agalactiae, Neiserria gonorrhoeae, Chlamydia trachomatis, Treponema pallidum* (Syphilis), *Haemophilus ducreyi, Enterococcus faecalis, Enterococcus faecium, Helicobacter pylori, Staphylococcus saprophyticus, Yersinia enterocolitica, E. coli* (such as enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC; such as uropathogenic *E. coli* (UPEC) and meningitis/sepsis-associated *E. coli* (MNEC)), and/or enterohemorrhagic *E. coli* (EHEC), *Bacillus anthracis* (anthrax), *Yersinia pestis* (plague), *Mycobacterium tuberculosis, Rickettsia, Listeria monocytogenes, Chlamydia pneumoniae, Vibrio cholerae, Salmonella typhi* (typhoid fever), *Borrelia burgdorfer, Porphyromonas gingivalis, Klebsiella, Mycoplasma pneumoniae*, etc.

Fungal antigens and immunogens that can be encoded by the self-replicating RNA molecule include, but are not limited to, proteins and peptides from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Protazoan antigens and immunogens that can be encoded by the self-replicating RNA molecule include, but are not limited to, proteins and peptides from *Entamoeba histolytica, Giardia lambli, Cryptosporidium parvum, Cyclospora cayatanensis* and *Toxoplasma*.

Plant antigens and immunogens that can be encoded by the self-replicating RNA molecule include, but are not limited to, proteins and peptides from *Ricinus communis*.

Suitable antigens include proteins and peptides from a virus such as, for example, human immunodeficiency virus (HIV), hepatitis A virus (HAV), hepatitis B virus (HBV), hepatitis C virus (HCV), herpes simplex virus (HSV), cytomegalovirus (CMV), influenza virus (flu), respiratory syncytial virus (RSV), parvovorus, norovirus, human papilloma virus (HPV), rhinovirus, yellow fever virus, rabies virus, Dengue fever virus, measles virus, mumps virus, rubella virus, varicella zoster virus, enterovirus (e.g., enterovirus 71), ebola virus, and bovine diarrhea virus. Preferably, the antigenic substance is selected from the group consisting of HSV glycoprotein gD, HIV glycoprotein gp120, HIV glycoprotein gp 40, HIV p55 gag, and polypeptides from the pol and tat regions. In other preferred embodiments of the invention, the antigen is a protein or peptide derived from a bacterium such as, for example, *Helicobacter pylori, Haemophilus influenza, Vibrio cholerae* (cholera), *C. diphtherias* (diphtheria), *C. tetani* (tetanus), *Neisseria meningitidis, B. pertussis, Mycobacterium tuberculosis*, and the like.

HIV antigens that can be encoded by the self-replicating RNA molecules of the invention are described in U.S. application Ser. No. 490,858, filed Mar. 9, 1990, and published European application number 181150 (May 14, 1986), as well as U.S. application Ser. Nos. 60/168,471; 09/475,515; 09/475,504; and 09/610,313, the disclosures of which are incorporated herein by reference in their entirety.

Cytomegalovirus antigens that can be encoded by the self-replicating RNA molecules of the invention are described in U.S. Pat. No. 4,689,225, U.S. application Ser. No. 367,363, filed Jun. 16, 1989 and PCT Publication WO 89/07143, the disclosures of which are incorporated herein by reference in their entirety.

Hepatitis C antigens that can be encoded by the self-replicating RNA molecules of the invention are described in PCT/US88/04125, published European application number 318216 (May 31, 1989), published Japanese application number 1-500565 filed Nov. 18, 1988, Canadian application 583,561, and EPO 388,232, disclosures of which are incorporated herein by reference in their entirety. A different set of HCV antigens is described in European patent application 90/302866.0, filed Mar. 16, 1990, and U.S. application Ser. No. 456,637, filed Dec. 21, 1989, and PCT/US90/01348, the disclosures of which are incorporated herein by reference in their entirety.

In some embodiments, the antigen is derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In certain embodiments, a tumor immunogen or antigen, or cancer immunogen or antigen, can be encoded by the self-replicating RNA molecule. In certain embodiments, the tumor immunogens and antigens are peptide-containing tumor antigens, such as a polypeptide tumor antigen or glycoprotein tumor antigens.

Tumor immunogens and antigens appropriate for the use herein encompass a wide variety of molecules, such as (a) polypeptide-containing tumor antigens, including polypeptides (which can range, for example, from 8-20 amino acids in length, although lengths outside this range are also common), lipopolypeptides and glycoproteins.

In certain embodiments, tumor immunogens are, for example, (a) full length molecules associated with cancer cells, (b) homologs and modified forms of the same, including molecules with deleted, added and/or substituted portions, and (c) fragments of the same. Tumor immunogens include, for example, class I-restricted antigens recognized by CD8+ lymphocytes or class II-restricted antigens recognized by CD4+ lymphocytes.

In certain embodiments, tumor immunogens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example).

In certain embodiments, tumor immunogens include, but are not limited to, p15, Horn/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

C. Aqueous Solution for the Negatively Charged Molecule

The negatively charged molecule (such as RNA) is generally provided in the form of an aqueous solution, or a form that can be readily dissolved in an aqueous solution (e.g., lyophilized). The aqueous solution can be water, or an aqueous solution that comprises a salt (e.g., NaCl), a buffer (e.g., a citrate buffer), an osmolality or tonicity adjusting agent (e.g., a saccharide), a polymer, a surfactant, or a combination thereof. If the formulation is intended for in vivo administration, it is preferable that the aqueous solution is a physiologically acceptable buffer that maintains a pH that is compatible with normal physiological conditions. Also, in certain instances, it may be desirable to maintain the pH at a particular level in order to insure the stability of certain components of the formulation.

For example, it may be desirable to prepare an aqueous solution that is isotonic and/or isosmotic. Hypertonic and hypotonic solutions sometimes could cause complications and undesirable effects when injected, such as post-administration swelling or rapid absorption of the composition because of differential ion concentrations between the composition and physiological fluids. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate dehydrate, magnesium chloride, calcium chloride, etc. In an exemplary embodiment, the aqueous solution comprises 10 mM NaCl and other salts or non-ionic tonicifying agents. As described herein, non-ionic tonicifying agents can also be used to control tonicity.

The aqueous solution may be buffered. Any physiologically acceptable buffer may be used herein, such as citrate buffers, phosphate buffers, acetate buffers, succinate buffer, tris buffers, bicarbonate buffers, carbonate buffers, or the like. The pH of the aqueous solution will preferably be between 6.0-8.0, preferably about 6.2 to about 6.8. In some cases, certain amount of salt may be included in the buffer. In other cases, salt in the buffer might interfere with complexation of negatively charged molecule to the emulsion particle, therefore is avoided.

The aqueous solution may also comprise additional components such as molecules that change the osmolarity of the aqueous solution or molecules that stabilizes the negatively charged molecule after complexation. For example, the osmolality can be adjusted using a non-ionic tonicifying agent, which are generally carbohydrates but can also be polymers. (See, e.g., Voet and Voet (1990) Biochemistry (John Wiley & Sons, New York.) Examples of suitable non-ionic tonicifying agents include sugars (e.g., trehalose, sucrose, dextrose, fructose, reduced palatinose, etc.), sugar alcohols (such as mannitol, sorbitol, xylitol, erythritol, lactitol, maltitol, glycerol, etc.), and combinations thereof. If desired, a nonionic polymer (e.g., a poly(alkyl glycol) such as polyethylene glycol, polypropylene glycol, or polybutlyene glycol) or nonionic surfactant can be used. These types of agents, in particular sugar and sugar alcohols, are also cryoprotectants that can procted RNA, and other negatibely charged molecules, when lyophilized. In exemplary embodiments, the buffer comprises from about 560 nM to 600 mM of trehalose, sucrose, sorbitol, or dextrose.

In some case, it may be preferable to prepare an aqueous solution comprising the negatively charged molecule as a hypertonic solution, and to prepare the cationic emulsion using unadulterated water or a hypotonic buffer. When the emulsion and the negatively charged molecule are combined, the mixture becomes isotonic. For example, an aqueous solution comprising RNA can be a 2× hypertonic solution, and the cationic emulsion can be prepared using 10 mM Citrate buffer. When the RNA solution and the emulsion are mixed at 1:1 (v/v) ratio, the composition becomes isotonic. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the tonicity of the aqueous solution that is required in order to achieve an isotonic mixture.

Similarly, compositions that have physiological osmolality may be desirable for in vivo administration. Physiological osmolality is from about 255 mOsm/kg water to about 315 mOsm/kg water. Sometimes, it may be preferable to prepare an aqueous solution comprising the negatively charged molecule as a hyperosmolar solution, and to prepare the cationic emulsion using unadulterated water or a hypoosmolar buffer. When the emulsion and the negatively charged molecule are combined, physiological osmolality is achieved. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the osmolality of the aqueous solution that is required in order to achieve an iso-osmolar mixture.

In certain embodiments, the aqueous solution comprising the negatively charged molecule may further comprise a polymer or a surfactant, or a combination thereof. In an exemplary embodiment, the oil-in-water emulsion contains a poloxamer. In particular, the inventors have observed that adding Pluronic® F127 to the RNA aqueous solution prior to complexation to cationic emulsion particles led to greater stability and increased RNase resistance of the RNA molecule. Addition of pluronic F127 to RNA aqueous solution was also found to decrease the particle size of the RNA/CNE complex. Poloxamer polymers may also facilitate appropriate decomplexation/release of the RNA molecule, prevent aggregation of the emulsion particles, and have immune modulatory effect. Other polymers that may be used include, e.g., Pluronic® F68 or PEG300.

Alternatively or in addition, the aqueous solution comprising the negatively charged molecule may comprise from about 0.05% to about 20% (w/v) polymer. For example, the cationic oil-in-water emulsion may comprise a polymer (e.g., a poloxamer such as Pluronic® F127, Pluronic® F68, or PEG300) at from about 0.05% to about 10% (w/v), such as 0.05%, 0.5%, 1%, or 5%.

The buffer system may comprise any combination of two or more molecules described above (salt, buffer, saccharide, polymer, etc). In an preferred embodiment, the buffer comprises 560 mM sucrose, 20 mM NaCl, and 2 mM Citrate, which can be mixed with a cationic oil in water emulsion described herein to produce a final aqueous phase that comprises 280 mM sucrose, 10 mM NaCl and 1 mM citrate.

5. Methods of Preparation

In another aspect, the invention provides a method of preparing a composition that comprises a negatively charged molecule complexed with a particle of a cationic oil-in-water emulsion, comprising: preparing a cationic oil-in-water emulsion wherein the emulsion comprises: (1) from about 0.2% to about 20% (v/v) oil, (2) from about 0.01% to about 2.5% (v/v) surfactant, and (3) a cationic lipid; and adding the negatively charged molecule to the cationic oil-in-water emulsion so that the negatively charged molecule complexes with the particle of the emulsion.

One exemplary approach to generate the cationic oil-in-water emulsion is by a process comprising: (1) combining the oil and the cationic lipid to form the oil phase of the emulsion; (2) providing an aqueous solution to form the aqueous phase of the emulsion; and (3) dispersing the oil phase in the aqueous phase, for example, by homogenization. Homogenization may be achieved in any suitable way, for example, using a commercial homogenizer (e.g., IKA T25 homogenizer, available at VWR International (West Chester, Pa.).

The cationic lipid may be dissolved in a suitable solvent, such as chloroform ($CHCl_3$), dichloromethane (DCM), ethanol, acetone, Tetrahydrofuran (THF), 2,2,2 trifluoroethanol, acetonitrile, ethyl acetate, hexane, Dimethylformamide (DMF), Dimethyl sulfoxide (DMSO), etc., and added directly to the oil component of the emulsion. Alternatively, the cationic lipid may be added to a suitable solvent to form a liposome suspension; then the liposome suspension may be added to the oil component of the emulsion. The cationic lipid may also be dissolved directly in the oil.

It may be desirable to heat the oil to a temperature between about 30° C. to about 65° C. to facilitate the dissolving of the lipid.

Desired amount of the cationic lipid (e.g., DOTAP) can be measured and either dissolved in a solvent, in water, or directly in oil to reach a desired final concentration as described and exemplified herein.

Solvents such as chloroform ($CHCl_3$) or dichloromethane (DCM) may be removed from the oil phase, e.g., by evaporation, prior to combining the aqueous phase and the oil phase or prior to homogenization. Alternatively, in instances where lipid solubility can be an issue, a primary emulsion can be made with the solvent (e.g. DCM) still in the oil phase. In such cases, the solvent can be removed (e.g., allowed to evaporate) from the primary emulsion prior to a secondary homogenization.

If the emulsion comprises one or more surfactants, the surfactant(s) may be included in the oil phase or the aqueous phase according to the conventional practice in the art. For example, SPAN85 can be dissolved in the oil phase (e.g., squalene), and Tween 80 may be dissolved in the aqueous phase (e.g., in a citrate buffer).

In another aspect, the invention provides a method of preparing a composition that comprises a negatively charged molecule (such as RNA) complexed with a particle of a cationic oil-in-water emulsion, comprising: (i) providing a cationic oil-in-water emulsion as described herein; (ii) providing a aqueous solution comprising the negatively charged molecule (such as RNA); and (iii) combining the oil-in-water emulsion of (i) and the aqueous solution of (iii), so that the negatively charged molecule complexes with the particle of the emulsion. For example, a cationic oil-in-water emulsion may be combined with an aqueous solution comprising a negatively charged molecule (e.g., an aqueous RNA solution) in any desired relative amounts, e.g., about 1:1 (v/v), about 1.5:1 (v/v), about 2:1 (v/v), about 2.5:1 (v/v), about 3:1 (v/v), about 3.5:1 (v/v), about 4:1 (v/v), about 5:1 (v/v), about 10:1 (v/v), about 1:1.5 (v/v), about 1:2 (v/v), about 1:2.5 (v/v), about 1:3 (v/v), about 1:3.5 (v/v), about 1:4 (v/v), about 1:1.5 (v/v), or about 1:1.10 (v/v), etc.

The concentration of each component of the post-complex composition (e.g., RNA-emulsion complex) can be readily determined according to relative amounts of the pre-complex oil-in-water emulsion and the aqueous solution comprising the negatively charged molecule (e.g., an aqueous RNA solution) that are used. For example, when a cationic oil-in-water emulsion is combined with an aqueous solution comprising a negatively charged molecule (e.g., an aqueous RNA solution) at 1:1 (v:v) ratio, the concentrations of the oil and cationic lipid become ½ of that of the pre-complex emulsion. Therefore, if an emulsion comprising 4.3% (w/v) squalene, 1.4 mg/mL DOTAP, 0.5% v/v SPAN85 and 0.5% v/v Tween 80 (referred herein as "CNE17") is combined with an aqueous RNA solution that comprises 560 mM sucrose, 20 mM NaCl, 2 mM Citrate, and 1% (w/v) Pluronic F127 at 1:1 (v:v), the post-complex composition comprises 2.15% (w/v) squalene, 0.7 mg/mL DOTAP, 0.25% v/v SPAN85, 0.25% v/v Tween 80, 280 mM sucrose, 10 mM NaCl, 1 mM Citrate, and 0.5% (w/v) Pluronic F127.

Additional optional steps to promote particle formation, to improve the complexation between the negatively charged molecules and the cationic particles, to increase the stability of the negatively charged molecule (e.g., to prevent degradation of an RNA molecule), to facilitate appropriate decomplexation/release of the negatively charged molecules (such as an RNA molecule), or to prevent aggregation of the emulsion particles may be included. For example, a polymer (e.g., Pluronic® F127) or a surfactant may be added to the aqueous solution that comprises the negatively charged molecule (such as RNA). In one exemplary embodiment, Pluronic® F127 is added to the RNA molecule prior to complexation to the emulsion particle.

The size of the emulsion particles can be varied by changing the ratio of surfactant to oil (increasing the ratio decreases droplet size), operating pressure (increasing operating pressure reduces droplet size), temperature (increasing temperature decreases droplet size), and other process parameters. Actual particle size will also vary with the particular surfactant, oil, and cationic lipid used, and with the particular operating conditions selected. Emulsion particle size can be verified by use of sizing instruments, such as the commercial Sub-Micron Particle Analyzer (Model N4MD) manufactured by the Coulter Corporation, and the parameters can be varied using the guidelines set forth above until the average diameter of the particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, or less than 0.1 µm. Preferably, the particles have an average diameter of about 400 nm or less, about 300 nm or less, about 200 nm or less, about 180 nm or less, about 150 nm or less, or about 140 nm or less, from about 50 nm to 180 nm, from about 60 nm to 180 nm, from about 70 to 180 nm, or from about 80 nm to 180 nm, from about 80 nm to 170 nm, from about 80 nm to 160 nm, from about 80 nm to 150 nm, or from about 80 nm to 140 nm. In some cases, it may be desirable that the mean particle size of the cationic emulsions is to 200 nm or less to allow for sterile filtration. In other cases, sterile filtration is not required and the mean particle size of the cationic emulsions can be greater than 200 nm.

Optional processes for preparing the cationic oil-in-water emulsion (pre-complexation emulsion), or the negatively charged molecule-emulsion complex, include, e.g., sterilization, particle size selection (e.g., removing large particles), filling, packaging, and labeling, etc.

For example, if the pre-complexation emulsion, or the negatively charged molecule-emulsion complex, is formulated for in vivo administration, it may be sterilized, e.g., by filtering through a sterilizing grade filter (e.g., through a 0.22 micron filter). Other sterilization techniques include a thermal process, or a radiation sterilization process, or using pulsed light to produce a sterile composition.

The cationic oil-in-water emulsion described herein can be used to manufacture vaccines. Sterile and/or clinical grade cationic oil-in-water emulsions can be prepared using similar methods as described for MF59. See, e.g., Ott et al., Methods in Molecular Medicine, 2000, Volume 42, 211-228, in VACCINE ADJUVANTS (O'Hagan ed.), Humana Press. For example, similar to the manufacturing process of MF59, the oil phase and the aqueous phase of the emulsion can be combined and processed in an inline homogenizer to yield a coarse emulsion. The coarse emulsion can then be fed into a microfluidizer, where it can be further processed to obtain a stable submicron emulsion. The coarse emulsion can be passed through the interaction chamber of the microfluidizer repeatedly until the desired particle size is obtained. The bulk emulsion can then be filtered (e.g., though a 0.22-µm filter under nitrogen) to remove large particles, yielding emulsion bulk that can be filled into suitable containers (e.g., glass bottles). For vaccine antigens that have demonstrated long-term stability in the presence of oil-in-water emulsion for self storage, the antigen and emulsion may be combined and sterile-filtered (e.g., though a 0.22-µm filter membrane). The combined single vial vaccine can be filled into single-dose containers. For vaccine antigens where long-term stability has not been demonstrated, the emulsion can be supplied as a separate vial. In such cases, the emulsion bulk can be filtered-sterilized (e.g., though a 0.22-µm filter membrane), filled, and packaged in final single-dose vials.

Quality control may be optionally performed on a small sample of the emulsion bulk or admixed vaccine, and the bulk or admixed vaccine will be packaged into doses only if the sample passes the quality control test.

6. Pharmaceutical Compositions and Administration

In another aspect, the invention provides a pharmaceutical composition comprising a negatively charged molecule complexed with a particle of a cationic oil-in-water emulsion, as described herein, and may further comprise one or more pharmaceutically acceptable carriers, diluents, or excipients. In preferred embodiments, the pharmaceutical composition is an immunogenic composition, which can be used as a vaccine.

Alternatively, the compositions described herein may be used to deliver a negatively charged molecule to cells. For example, nucleic acid molecules (e.g., DNA or RNA) can be delivered to cells for a variety of purposes, such as to induce production of a desired gene product (e.g., protein), to regulate expression of a gene, for gene therapy and the like. The compositions described herein may also be used to deliver a nucleic acid molecule (e.g., DNA or RNA) to cells for therapeutic purposes, such as to treat a disease such as cancers or proliferative disorders, metabolic diseases, cardiovascular diseases, infections, allergies, to induce an immune response and the like. For example, nucleic acid molecules may be delivered to cells to inhibit the expression of a target gene. Such nucleic acid molecules include, e.g., antisense oligonucleotides, double-stranded RNAs, such as small interfering RNAs and the like. Double-stranded RNA molecules, such as small interfering RNAs, can trigger RNA interference, which specifically silences the corresponding target gene (gene knock down). Antisense oligonucleotides are single strands of DNA or RNA that are complementary to a chosen sequence. Generally, antisense RNA can prevent protein translation of certain messenger RNA strands by binding to them. Antisense DNA can be used to target a specific, complementary (coding or non-coding) RNA. Therefore, the cationic emulsions described herein are useful for delivering antisense oligonucleotides or double-stranded RNAs for treatment of, for example, cancer by inhibiting production of an oncology target.

The pharmaceutical compositions provided herein may be administered singly or in combination with one or more additional therapeutic agents. The method of administration include, but are not limited to, oral administration, rectal administration, parenteral administration, subcutaneous administration, intravenous administration, intravitreal administration, intramuscular administration, inhalation, intranasal administration, topical administration, ophthalmic administration, or otic administration.

A therapeutically effective amount of the compositions described herein will vary depending on, among others, the disease indicated, the severity of the disease, the age and relative health of the subject, the potency of the compound administered, the mode of administration and the treatment desired.

In other embodiments, the pharmaceutical compositions described herein can be administered in combination with one or more additional therapeutic agents. The additional therapeutic agents may include, but are not limited to, antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, and other toll-like receptor modulators, immunoglobulins (Igs), and antibodies modulating Ig function (such as anti-IgE (omalizumab)).

In certain embodiments, the pharmaceutical compositions provided herein are used in the treatment of infectious diseases including, but not limited to, disease cased by the pathogens disclosed herein, including viral diseases such as genital warts, common warts, plantar warts, rabies, respiratory syncytial virus (RSV), hepatitis B, hepatitis C, Dengue virus, yellow fever, herpes simplex virus (by way of example only, HSV-I, HSV-II, CMV, or VZV), molluscum contagiosum, vaccinia, variola, lentivirus, human immunodeficiency virus (HIV), human papilloma virus (HPV), hepatitis virus (hepatitis C virus, hepatitis B virus, hepatitis A virus), cytomegalovirus (CMV), varicella zoster virus (VZV), rhinovirus, enterovirus (e.g. EV71), adenovirus, coronavirus (e.g., SARS), influenza, para-influenza, mumps virus, measles virus, rubella virus, papovavirus, hepadnavirus, flavivirus, retrovirus, arenavirus (by way of example only, LCM, Junin virus, Machupo virus, Guanarito virus and Lassa Fever) and Filovirus (by way of example only, ebola virus or marburg virus).

In certain embodiments, the pharmaceutical compositions provided herein are used in the treatment of bacterial, fungal, and protozoal infections including, but not limited to, malaria, tuberculosis and mycobacterium avium, leprosy; pneumocystis carnii, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus,* and *Chlamydia*, and fungal infections such as candidiasis, aspergillosis, histoplasmosis, and cryptococcal meningitis.

In certain embodiments, the pharmaceutical compositions provided herein are used in the treatment of respiratory diseases and/or disorders, dermatological disorders, ocular diseases and/or disorders, genitourinary diseases and/or disorders including, allograft rejection, auto-immune and allergic, cancer, or damaged or ageing skin such as scarring and wrinkles.

In another aspect, the invention provides a method for generating or potentiating an immune response in a subject in need thereof, such as a mammal, comprising administering an effective amount of a composition as disclosed herein. The immune response is preferably protective and preferably involves antibodies and/or cell-mediated immunity. The method may be used to induce a primary immune response and/or to boost an immune response.

In certain embodiments, the compositions disclosed herein may be used as a medicament, e.g., for use in raising or enhancing an immune response in a subject in need thereof, such as a mammal.

In certain embodiments, the compositions disclosed herein may be used in the manufacture of a medicament for generating or potentiating an immune response in a subject in need thereof, such as a mammal.

The invention also provides a delivery device pre-filled with a composition or a vaccine disclosed herein.

The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

The compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

In certain embodiments, the compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:
1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

EXEMPLIFICATION

The invention now being generally described, it will be more readily understood by reference to the following examples, which are included merely for purposes of illustration of certain aspects and embodiments of the present invention, and are not intended to limit the invention.

Example 1: Development of Cationic Oil-in-Water Emulsions

Three types of cationic nanoemulsions (CNEs) were developed for the delivery of self replicating RNA. Type 1 emulsions are "MF59" like emulsions. These emulsions were made from the same components of MF59 with the exception that cationic lipids are added. Type 2 emulsions are emulsions that replace the Span 85 and Tween 80 in MF59 with phospholipids. Type 3 emulsions are hybrid emulsions that are stabilized by either lipids or other surfactants and can have additional polymers or surfactants in the aqueous phase of the emulsion.

Three different lipids were used in the preparation of Type 1 emulsions: 1,2-dioleoyl-3-trimethylammonium-propane (chloride salt) (DOTAP), 3ß-[N—(N',N'-dimethylaminoethane)-carbamoyl]cholesterol hydrochloride (DC Cholesterol) and Dimethyldioctadecylammonium (Bromide Salt) (DDA). DOTAP was used in the preparation of Type 2 and Type 3 emulsions.

The term N/P ratio refers to the amount of nitrogen in the cationic lipid in relation to the amount of phosphates on the RNA. The nitrogen is the charge bearing element within the cationic lipids tested. The phosphate can be found on the RNA backbone. An N/P charge ratio of 10/1 indicates that there are 10 positively charged nitrogens from the cationic lipid present for each negatively charged phosphate on the RNA.

Type 1 CNEs:

The ratio of Tween 80, Span 85, squalene, and citrate buffer were not changed for this class of emulsions. These emulsions were prepared at the same concentrations as MF59. The total amount of cationic lipid given per dose remains constant regardless of the lipid concentration. For example a 10 µg dose of RNA delivered in an emulsion with 0.8 mg/ml DOTAP emulsion at an N/P ratio of 10/1 would require a 2× dilution. Hence the amount of squalene delivered would be ½ of what is normally administered during immunization with MF59. Alternatively a 10 µg dose of RNA delivered in an emulsion with 1.6 mg/ml DOTAP at an N/P ratio of 10/1 would require a 4× dilution.

In this example, 17 different formulations of Type 1 emulsions were prepared. The ranges of cationic lipids that were able to be made into emulsions are listed below:

TABLE 1

| | |
|---|---|
| DOTAP | 0.8 mg/ml up to 1.6 mg/ml |
| DC cholesterol | 0.62 mg/ml up to 2.46 mg/ml |
| DDA | 0.73 mg/ml up to 1.64 mg/ml |

Formulations with DOTAP concentrations of 0.8 mg/ml up to 1.6 mg/ml all produced stable emulsions. Formulations with DC cholesterol concentrations of 0.62 mg/ml up to 2.46 mg/ml all produced stable emulsions. Formulations with DDA concentrations of 0.73 mg/ml up to 1.64 mg/ml all produced stable emulsions.

Type 2 CNEs:

The percentage of squalene varied with Type 2 CNEs. Another difference from MF59 is that these emulsions were made in water not in citrate buffer. These emulsions were made with 1,2-dioleoyl-sn-glycero-3-phosphatidylethanolamine (DOPE) and phosphatidylcholine (egg PC) as lipid stabilizers. Emulsions were made using DOPE and egg PC with either DOTAP, DC cholesterol or DDA at the optimized concentrations from the type 1 emulsion studies.

A separate series of emulsions were made using only DOTAP as the stabilizer. These emulsions contained various amounts of squalene (from 0.43% w/w up to the MF59 concentration of 4.3% w/w).

Type 3 CNEs:

The addition of Pluronic® F127 (poloxomer) to the RNA prior to complexation to a DOTAP/Egg PC emulsion led to greater RNase stability when compared to a sample that did not have the poloxamer added to it. This indicates the role of this polymer in allowing for better RNA complexation with the oil droplet.

The addition of a small amount of tween 80 (0.08% w/w) during the emulsification step of the DOTAP-only emulsions led to a smaller droplet size.

DOTAP chloroform solution using a rotary evaporator (Buchi model number R200) at 300 milliTorr, pressure for 30 minutes at a temperature of 50° C. Residual chloroform evaporation was insured by placing the samples overnight in a Labconco freeze dryer. The lipid film was hydrated and dispersed by adding 1.0 mL of filtered deionized distilled water and placed at 50° C. to ensure full suspension of the lipid. The resulting liposomes were added directly to the squalene and were immediately emulsified for 2 min using an IKA T25 homogenizer at 24K RPM. Emulsions were then allowed to sit at room temperature on a stirplate for 2-3 hours after primary homogenization in a fume hood. The primary emulsions were passed three to five times through a Microfluidezer M110S homogenizer with an ice bath cooling coil at a homogenization pressure of approximately 15 k-20 k PSI (Microfluidics, Newton, Mass.). The 20 ml batch samples were removed from the unit and stored at 4° C. Table 2 describes the components of the emulsions.

TABLE 2

| CNE | Cationic Lipid (+) | mg/ml + Lipid | Surfactant | Squalene | Buffer/water |
|---|---|---|---|---|---|
| CNE01 | DOTAP (in CHCl3) | 0.8 | 0.5% SPAN 85 0.5% Tween 80 | 4.3% | 10 mM citrate buffer pH 6.5 |
| CNE02 | DOTAP (in CHCl3) | 1.6 | 0.5% SPAN 85 0.5% Tween 80 | 4.3% | 10 mM citrate buffer pH 6.5 |
| CNE05 | DOTAP (in CHCl3) | 1.2 | 0.08% Tween 80 | 0.5% | DEPC treated water |
| CNE12 | DC Cholesterol (in DCM) | 2.46 | 0.5% SPAN 85 0.5% Tween 80 | 4.3% | 10 mM citrate buffer pH 6.5 |
| CNE13 | DDA (in DCM) | 1.45 | 0.5% SPAN 85 0.5% Tween 80 | 4.3% | 10 mM citrate buffer pH 6.5 |
| CNE17 | DOTAP (in DCM) | 1.40 | 0.5% SPAN 85 0.5% Tween 80 | 4.3% | 10 mM citrate buffer pH 6.5 |
| CNE27 | DOTAP (in DCM) + 30 mg DOPE | 1.40 | — | 4.3% | Rnase-free dH$_2$O |
| CNE32 | DOTAP (in DCM) + 30.9 mg Egg PC | 1.40 | — | 4.3% | Rnase-free dH$_2$O |
| CNE35 | DOTAP (in DCM) + 32.16 mg DPyPE | 1.40 | — | 4.3% | Rnase-free dH$_2$O |

Methods of Preparing Cationic Emulsions:

Squalene, sorbitan trioleate (Span 85), polyoxy-ethylene sorbitan monololeate (Tween 80) were obtained from Sigma (St. Louis, Mo., USA). Dimethyldioctadecylammonium (DDA), 1,2-dioleoyl-sn-glycero-3-phosphoethanolamine (DOPE), 3ß-[N—(N',N'-Dimethylaminoethane)-carbamoyl] Cholesterol Hydrochloride (DC-Cholesterol HCl), were purchased from Avanti Lipids. L-α-lysophosphatidylcholine (Egg, Chicken) and 1,2-Dioleoyl-3-trimethylammonium-propane (DOTAP) were purchased from Lipoid (Ludwigshafen Germany).

Cationic nanoemulsions (CNEs) were prepared similar to charged MF59 as previously described with minor modifications (Ott, Singh et al. 2002). Briefly, oil soluble components (ie. Squalene, span 85, cationic lipids, lipid surfactants) were combined in a beaker, lipid components were dissolved in chloroform (CHCl$_3$) or dichloromethane (DCM). The resulting lipid solution was added directly to the oil plus span 85. For a subset of emulsions (CNE01, 02, 17) the solvent was allowed to evaporate at room temperature for 2 hours in a fume hood prior to combining the aqueous phase and homogenizing the sample. For the remaining emulsions (CNE 12, 13, 27, 32, 35), the oil phase was combined with the aqueous phase and immediately homogenized for 2 min using an IKA T25 homogenizer at 24K RPM in order to provide a homogeneous feedstock. CNE05 was prepared by preparing a liposome stock solution. Liposomes were prepared by evaporating the 10 mg/ml One method of addition of the lipids into the oil phase of the emulsions was adding dichloromethane (DCM or methylene chloride) into the oil phase. Once added the DCM could be allowed to evaporate fully. After evaporation, emulsion was then passed through the Microfluidizer. Alternatively, in instances where lipid solubility was an issue the primary emulsion could be made with the DCM still in the organic phase. In that case, the DCM would be allowed to evaporate directly from the emulsion prior to secondary homogenization.

An alternative method for emulsions that contained lipids as stabilizers was to make a lipid film and rehydrate the film, so that the lipids formed liposomes. The liposomes were then added to the oil phase and processed as standard MF59 was processed.

Example 2: Preparing RNA-Particle Complexes

1. Materials and Methods.
RNA Synthesis

Plasmid DNA encoding an alphavirus replicon (self-replicating RNA) was used as a template for synthesis of RNA in vitro. Each replicon contains the genetic elements required for RNA replication but lacks sequences encoding gene products that are necessary for particle assembly. The structural genes of the alphavirus genome were replaced by sequences encoding a heterologous protein (whose expression is driven by the alphavirus subgenomic promoter). Upon delivery of the replicons to eukaryotic cells, the positive-stranded RNA is translated to produce four non-structural proteins, which together replicate the genomic RNA and transcribe abundant subgenomic mRNAs encoding the heterologous protein. Due to the lack of expression of the alphavirus structural proteins, replicons are incapable of generating infectious particles. A bacteriophage T7 promoter is located upstream of the alphavirus cDNA to facilitate the synthesis of the replicon RNA in vitro, and the hepatitis delta virus (HDV) ribozyme located immediately downstream of the poly(A)-tail generates the correct 3'-end through its self-cleaving activity. The sequences of the four plasmids used in the examples are shown in FIGS. 7A-7B.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) final concentration of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. Uncapped RNA was capped post-transcriptionally with Vaccinia Capping Enzyme (VCE) using the ScriptCap m$^7$G Capping System (Epicentre Biotechnologies, Madison, Wis.) as outlined in the user manual. Post-transcriptionally capped RNA was precipitated with LiCl and reconstituted in nuclease-free water. Alternatively, replicons may be capped by supplementing the transcription reactions with 6 mM (for T7 RNA polymerase) or 4 mM (for SP6 RNA polymerase) m$^7$G(5')ppp(5')G, a non-reversible cap structure analog (New England Biolabs, Beverly, Mass.) and lowering the concentration of guanosine triphosphate to 1.5 mM (for T7 RNA polymerase) or 1 mM (for SP6 RNA polymerase). The transcripts may be then purified by TURBO DNase (Ambion, Austin, Tex.) digestion followed by LiCL precipitation and a wash in 75% ethanol.

The concentration of the RNA samples was determined by measuring the optical density at 260 nm. Integrity of the in vitro transcripts was confirmed by denaturing agarose gel electrophoresis for the presence of the full length construct.

RNA Complexation

The number of nitrogens in solution was calculated from the cationic lipid concentration, DOTAP for example has 1 nitrogen that can be protonated per molecule. The RNA concentration was used to calculate the amount of phosphate in solution using an estimate of 3 nmols of phosphate per microgram of RNA. By varying the amount of RNA: Lipid, the N/P ratio can be modified. RNA was complexed to the CNEs in a range of nitrogen/phosphate ratios (N/P). Calculation of the N/P ratio was done by calculating the number of moles of protonatable nitrogens in the emulsion per milliliter. To calculate the number of phosphates, a constant of 3 nmols of phosphate per microgram of RNA was used. After the values were determined, the appropriate ratio of the emulsion was added to the RNA. Using these values, the RNA was diluted to the appropriate concentration and added directly into an equal volume of emulsion while vortexing lightly. The solution was allowed to sit at room temperature for approximately 2 hours. Once complexed the resulting solution was diluted to the appropriate concentration and used within 1 hour.

Gel Electrophoresis

Denaturing gel electrophoresis was performed to assess binding of RNA with the cationic formulations and stability in the presence of RNase A. The gel was cast as follows: 2 g of agarose (Bio-Rad, Hercules, Calif.) was added to 180 ml of water and heated in a microwave until dissolved and then cooled to 60° C. 20 ml of 10× denaturing gel buffer (Ambion, Austin, Tex.), was then added to the agarose solution. The gel was poured and was allowed to set for at least 45 minutes at room temperature. The gel was then placed in a gel tank, and 1×MOPS running buffer (Ambion, Austin, Tex.) was added to cover the gel by a few millimeters.

RNase Protection Assay

RNase digestion was achieved by incubation with 6.4 mAU of RNase A per microgram of RNA (Ambion, Hercules, Calif.) for 30 minutes at room temperature. RNase was inactivated with Proteinase K (Novagen, Darmstadt, Germany) by incubating the sample at 55° C. for 10 minutes. Post-RNase inactivation samples were decomplexed with a 1:1 mixture of sample to 25:24:1, phenol:chloroform:isoamyl alcohol. Samples were inverted several times to mix and then placed on a centrifuge for 15 minutes at 12 k RPM. The aqueous phase was removed from the organic phase and used to analyze the RNA. Prior to loading (460 ng per well) all the samples were incubated with formaldehyde loading dye, denatured for 10 minutes at 65° C. and cooled to room temperature. Ambion Millennium markers were used to approximate the molecular weight of the RNA construct. The gel was run at 130 V. The gel was stained using 0.1% SYBR gold according to the manufacturer's guidelines (Invitrogen, Carlsbad, Calif.) in water by rocking at room temperature for 1 hour. Gel images were taken on a Bio-Rad Chemidoc XRS imaging system (Hercules, Calif.). All studies used mouse thymus RNA from Clonetech (Mountain View, Calif.).

Heparin Binding Assay

RNA was complexed as described above. The RNA/CNE complex was incubated with various concentrations of heparin sulfate (Alfa Aesar, Ward Hill Mass.) for 30 minutes at room temperature. The resulting solutions were centrifuged for 15-20 minutes minutes. The centrifuge tubes were punctured with a tuberculin syringe and the subnatant was removed. The solution was then assayed for RNA concentration using the Quant-it Ribogreen RNA Assay Kit (Invitrogen, Carlsbad Calif.) according to the manufacturer's directions. The samples were analyzed on a Biotek Synergy 4 (Winooski, Vt.) fluorescent plate reader. Free RNA values were calculated using a standard curve.

Particle Size Assay

Particle size of the emulsion was measured using a Zetasizer Nano ZS (Malvern Instruments, Worcestershire, UK) according to the manufacturer's instructions. Particle sizes are reported as the Z-Average (ZAve) with the polydispersity index (pdi). All samples were diluted in water prior to measurements. Additionally, particle size of the emulsion was measured using Horiba LA-930 particle sizer (Horiba Scientific, USA). Samples were diluted in water prior to measurements. Zeta potential was measured using Zetasizer Nano ZS using diluted samples according to the manufacturer's instructions.

Secreted Alkaline Phosphatase (SEAP) Assay

To assess the kinetics and amount of antigen production, an RNA replicon encoding for SEAP was administered with and without formulation to mice intramuscularly. Groups of 3 or 5 female Balb/C mice aged 8-10 weeks and weighing about 20 g were immunized with CNEs complexed with replicon RNA encoding for SEAP at the indicated N/P ratios. Naked RNA was formulated in RNase free 1×PBS. A 100 µl dose was administered to each mouse (50 µl per site) in the quadriceps muscle. Blood samples were taken 1, 3, and 6 days post injection. Serum was separated from the blood immediately after collection, and stored at −30° C. until use.

A chemiluminescent SEAP assay Phospha-Light System (Applied Biosystems, Bedford, Mass.) was used to analyze the serum. Mouse sera was diluted 1:4 in 1× Phospha-Light dilution buffer. Samples were placed in a water bath sealed with aluminum sealing foil and heat inactivated for 30 minutes at 65° C. After cooling on ice for 3 minutes, and equilibrating to room temperature, 50 uL of Phospha-Light assay buffer was added to the wells and the samples were left at room temperature for 5 minutes. Then, 50 uL of reaction buffer containing 1:20 CSPD® (chemiluminecent alkaline phosphate substrate) substrate was added, and the luminescence was measured after 20 minutes of incubation at room temperature. Luminescence was measured on a Berthold Centro LB 960 luminometer (Oak Ridge, Tenn.) with a 1 second integration per well. The activity of SEAP in each sample was measured in duplicate and the mean of these two measurements is shown.

Electroporation

Electroporation was a very effective method for the delivery of plasmid DNA vaccines and this technique was used to delivery self-replicating RNA. Mice were anesthetized under isofluorane, both hind legs were closely shaven to expose the area on the limb to be treated. A dose of 30 µl of vaccine was injected to the quadracepts muscle of the hind limb using a ½ cc insulin syringe. The muscle was electroporated using the Elgen® DNA Delivery System (Inovio, San Diego). The instrument parameters are as follows: 60V, 2 pulses each at 60 ms. Another dose was similarly delivered to the second limb, followed by electroporation.

Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al. In this system, the antigen (or reporter gene) replicons consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri S., et al., J Virol 77: 10394-10403 (2003)). These replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and titrated by standard methods and inoculated into animals in culture fluid or other isotonic buffers.

2. Particle Size Analysis of the Oil-in-Water Emulsions.

After manufacture the emulsions were analyzed for particle size and zeta potential. Tables 3 and 4 summarize the data particle size and zeta potential data obtained pre and post complexation at an N/P ratio of 4:1 and 10:1. Particle size of the emulsions was below 160 nm for all of the formulations tested when measured on the Nano ZS particle sizer. After complexation some of the particle sizes did increase significantly particularly at the 4:1 N/P ratio. This is likely due to the aggregation and bridging of the RNA between multiple emulsion droplets. Horriba data generally matched well with the NanoZS measurements except for a few cases (CNE02 and CNE32) where there seem to be a larger particle population that is not able to be analyzed on the nanoZS. All CNEs with the exception of CNE02 and CNE32 were less than 190 nm in size when measured on the Horiba particle sizer. The low variability in size indicates a robust processing method regardless of the amount or type of cationic lipid added. It is particularly desirable that the mean particle size to be below 200 nm in size to allow for sterile filtration. All samples tested pass this criterion.

TABLE 3

Particle size data

| Formulation | Horiba Measurement Not complexed | Nano ZS measurement | | |
|---|---|---|---|---|
| | | Not complexed | 4:1 N/P | 10:1 N/P |
| CNE01 | 187.8 | 159.6 | 156.7 | 141.9 |
| CNE02 | 535 | 121.9 | — | — |
| CNE05 | — | 110.1 | 143.6 | 132.3 |
| CNE12 | 127.1 | 124 | 366.6 | 153 |
| CNE13 | 128.5 | 117.4 | 273.3 | 163.4 |
| CNE17 | 129.4 | 134.8 | — | 164 |
| CNE27 | 137.2 | 134.6 | 223.5 | 139.2 |
| CNE32 | 279.8 | 114.8 | 185.4 | 134.7 |
| CNE35 | — | 134.7 | 161.1 | 142.7 |

Zeta potential was slightly more variable than the particle size data (Table 4). This is in line with our expectations since a number of the differences in these formulations is the change in cationic lipid concentration. For example CNE01, CNE02, and CNE17 each contain 0.8, 1.6 and 1.2 mg/ml of DOTAP respectively. The zeta potential for these lots were in line with expectations with CNE01 having the lowest zeta potential of 15.9 mV pre complexation, followed by CNE17 with a pre-complexation zeta potential of 33.4 mV, and lastly CNE02 with a zeta potential of 43 mV. The zeta potential post complexation is generally not changing much from the pre-complexation zeta potential likely due to the excess charge in the emulsions.

TABLE 4

Zeta potential

| Formulation | Not complexed (mV) | 4:1 N/P (mV) | 10:1 N/P (mV) |
|---|---|---|---|
| CNE01 | 15.9 | 41.4 | 36.6 |
| CNE02 | 43 | — | — |
| CNE05 | 74.2 | 44.9 | 15.2 |
| CNE12 | 24.5 | 18.2 | 24.8 |
| CNE13 | 26.3 | 33.2 | 33.4 |
| CNE17 | 33.4 | 33.9 | 30.7 |
| CNE27 | 63.2 | 25.1 | 26.8 |
| CNE32 | 66.9 | 39.2 | 27.6 |
| CNE35 | 78 | 23.9 | 43.6 |

Figure 2:
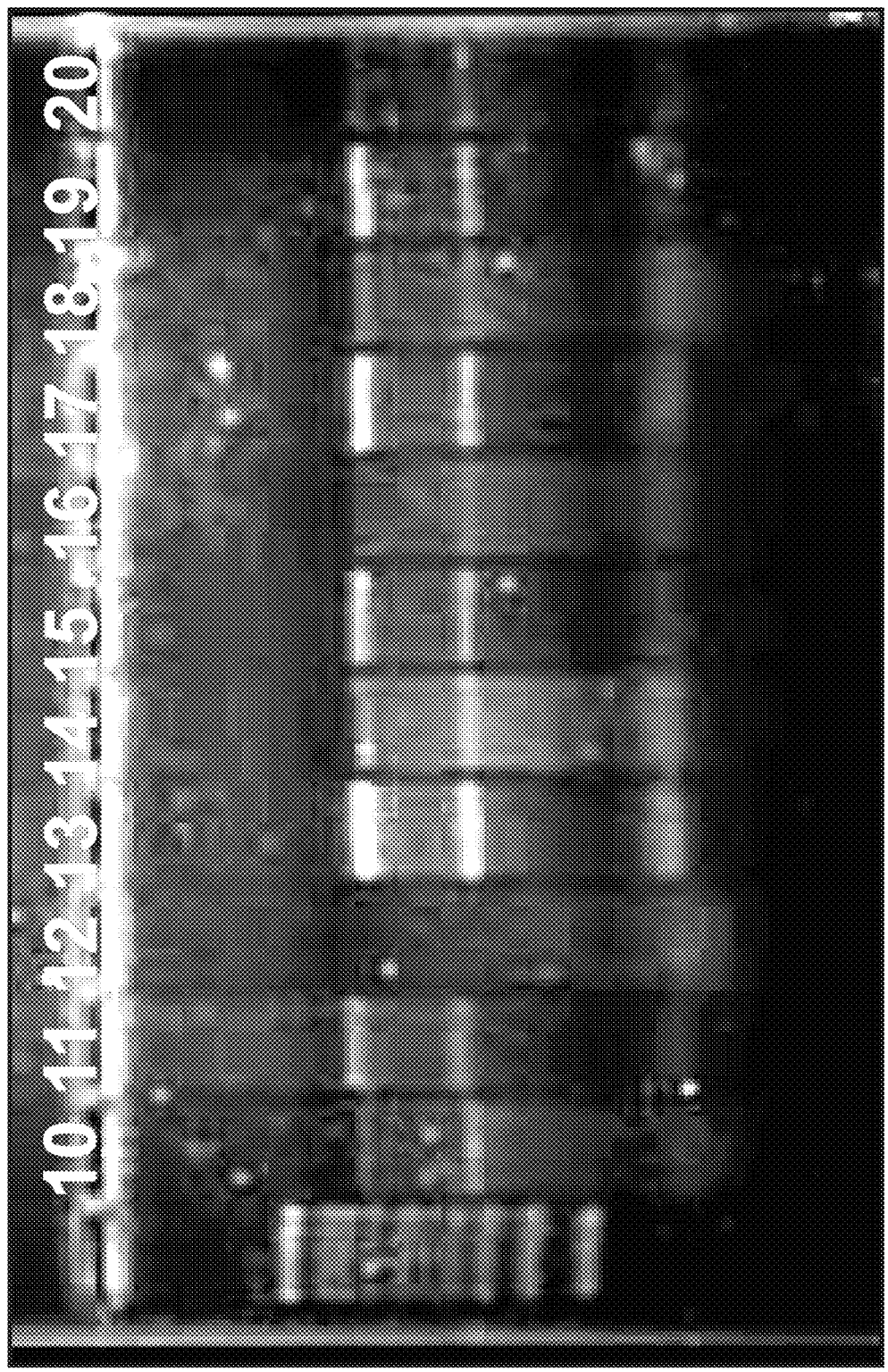
FIG. 2 shows the stability of mouse thymus RNA in the presence of RNase after the RNA molecule was complexed with CNE particles. All samples were incubated with RNase for 30 minutes. RNase was inactivated with proteinase K. Samples that were formulated with CNEs were decomplexed and analyzed for RNA integrity by denaturing gel electrophoresis. The unlabeled lane contains molecular weight markers. Lane 10: mouse thymus RNA complexed with CNE17 at an N/P ratio of 4:1 after (10) RNase digestion; lanes 11 and 12: mouse thymus RNA before (11) and after (12) RNase digestion; lanes 13 and 14: mouse thymus RNA complexed with CNE12 at an N/P ratio of 10:1 before (13) and after (14) RNase digestion; lanes 15 and 16: mouse thymus RNA complexed with CNE12 at an N/P ratio of 4:1 before (15) and after (16) RNase digestion; lanes 17 and 18: mouse thymus RNA complexed with CNE13 at an N/P ratio of 10:1 before (17) and after (18) RNase digestion; lanes 19 and 20 mouse:thymus RNA complexed with CNE13 at an N/P ratio of 4:1 before (19) and after (20) RNase digestion.
Figure 3:
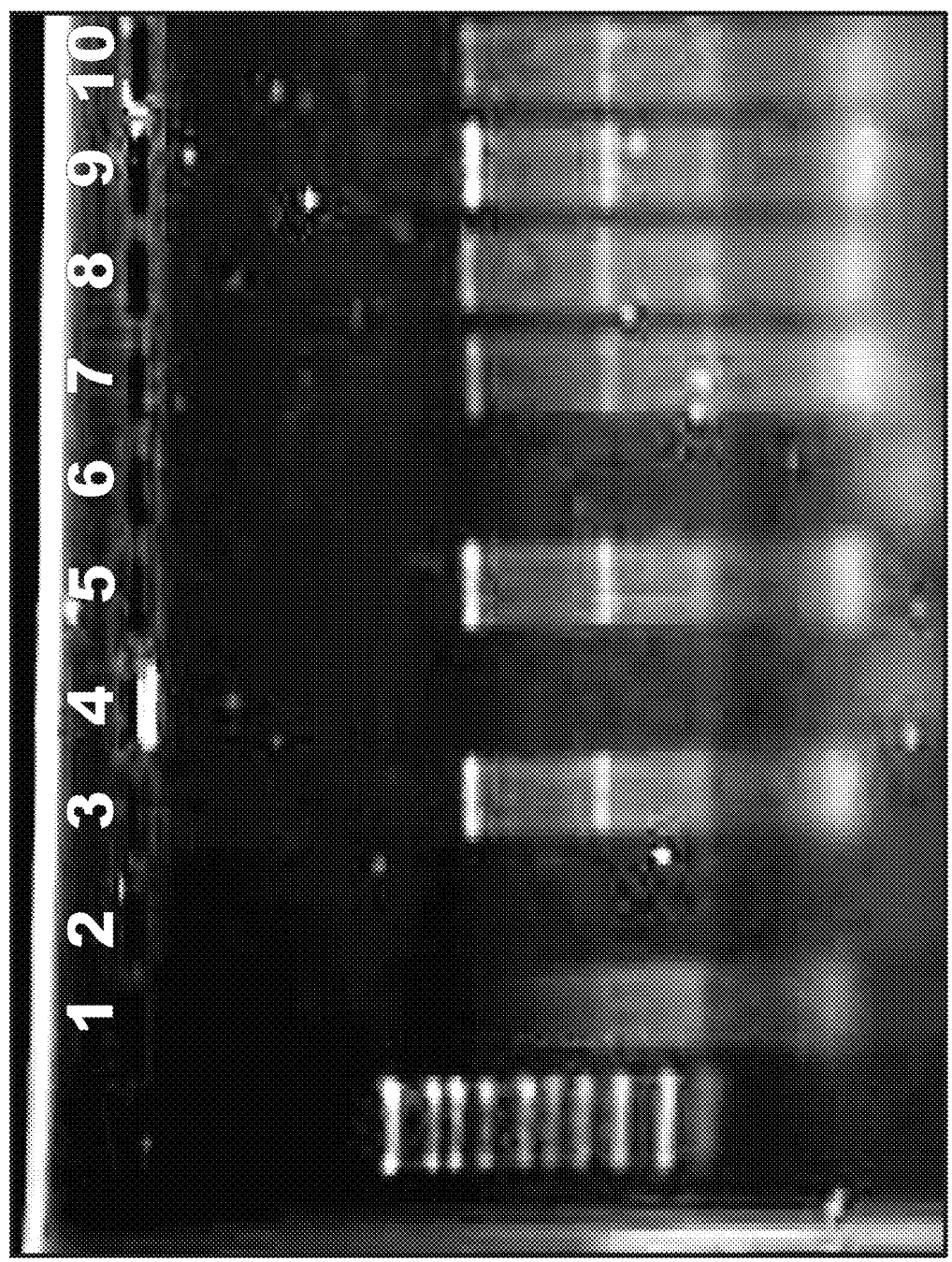
FIG. 3 shows the stability of mouse thymus RNA in the presence of RNase after the RNA molecule was complexed with CNE particles. All samples were incubated with RNase for 30 minutes. RNase was inactivated with proteinase K. Samples that were formulated with CNEs were decomplexed and analyzed for RNA integrity by denaturing gel electrophoresis. Unlabeled lane contains molecular weight markers. Lanes 1 and 2: mouse thymus RNA before (1) and after (2) RNase digestion; lanes 3 and 4 mouse: thymus RNA complexed with CNE01 at an N/P ratio of 10:1 before (3) and after (4) RNase digestion; lanes 5 and 6: mouse thymus RNA complexed with CNE01 at an N/P ratio of 4:1 before (5) and after (6) RNase digestion; lanes 7 and 8: mouse thymus RNA complexed with CNE02 at an N/P ratio of 10:1 before (7) and after (8) RNase digestion; lane 9: mouse thymus RNA complexed with CNE02 at an N/P ratio of 4:1 before (9) RNase digestion.
Figure 4:
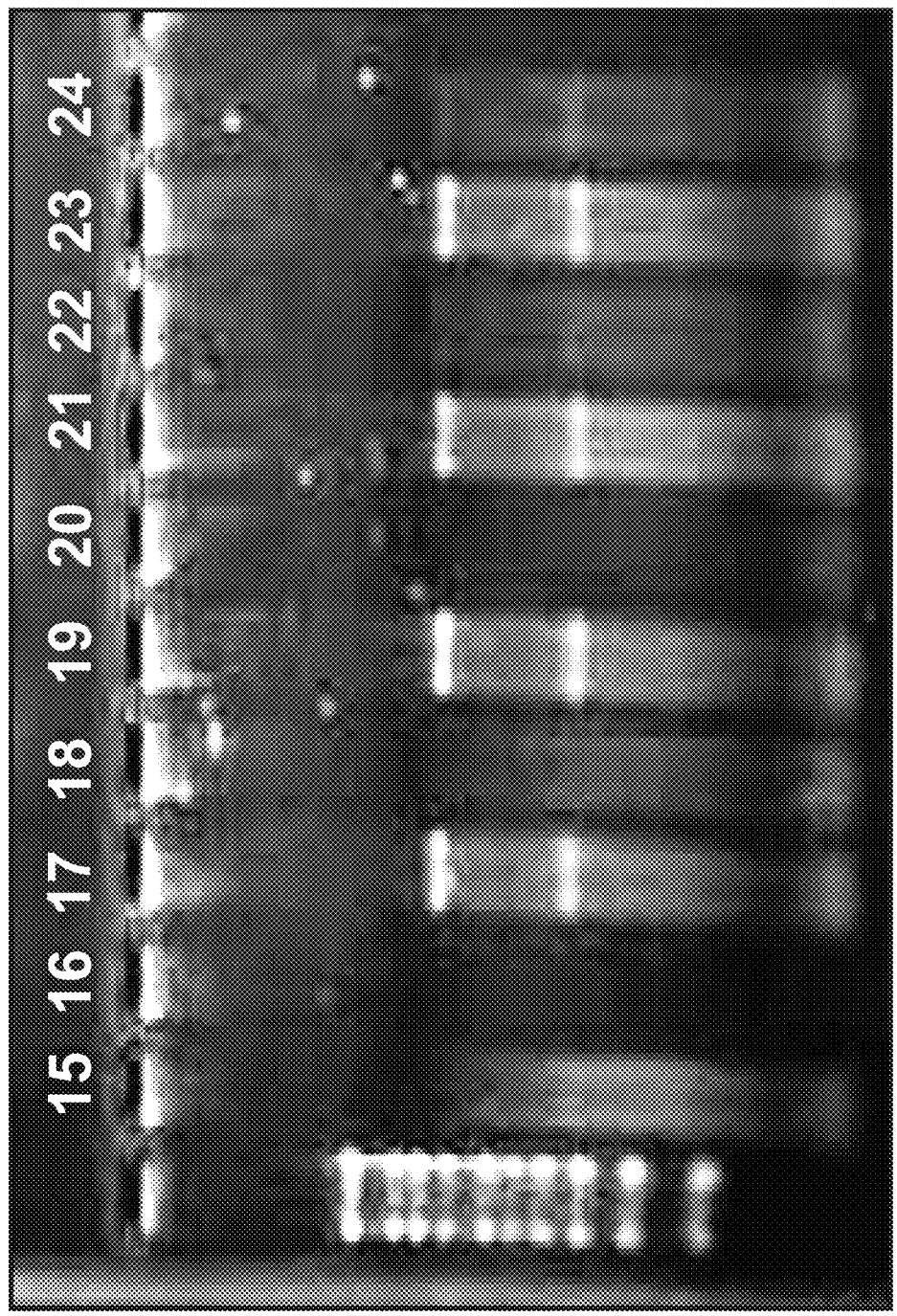
FIG. 4 shows the stability of mouse thymus RNA in the presence of RNase after the RNA molecule was complexed with CNE particles. All samples were incubated with RNase for 30 minutes. RNase was inactivated with proteinase K and samples that were formulated were decomplexed and analyzed for RNA integrity by denaturing gel electrophoresis. Unlabeled lane contains molecular weight markers. Lanes 15 and 16: mouse thymus RNA before (15) and after (16) RNase digestion; lanes 17 and 18: mouse thymus RNA complexed with CNE04 at an N/P ratio of 10:1 before (17)

3. RNase Stability Assay:

To assess the ability of the emulsions to protect from RNase degradation an in-vitro assay was developed to screen formulations. FIG. 1 shows the results of RNase protection assay of CNE01 and CNE17 at a 10:1 and 4:1 N/P ratio. CNE01 protected the RNA better at a 10:1 ratio compared to the 4:1 ratio. CNE17 showed good protection at 10:1. FIG. 2 shows that CNE17 was also able to protect the RNA at an N/P ratio of 4:1. CNE12 and 13 also protected the RNA (similar to CNE17) at both charge ratios (FIG. 2). FIG. 3 shows similar results as FIG. 1 with CNE01 not protecting very well at a 4:1 N/P ratio. CNE02 did protect against RNases very well at both N/P ratios tested (FIGS. 3 and 4). CNE04 did not protect the RNA from RNase digestion, but CNE05 was able to protect the RNA at both charge ratios tested (FIG. 5). CNE27 showed very little RNase protection, while CNE32 showed slightly more protection, but overall less than the previously mentioned formulations. CNE 35 (FIG. 6) was able to slightly protect the RNA from degradation from RNase. Overall 5 different formulations were able to prevent degradation of the RNA in vitro.

4. In Vivo SEAP Screening:

A306 replicon, which expresses secreted alkaline phosphatase (SEAP), was used to determine the protein expression level in vivo after administration of alphavirus vectors. BALB/c mice, 5 animals per group, were given bilateral intramuscular vaccinations (50 µL per leg) on days 0 with VRP's expressing SEAP ($5\times10^5$ IU), naked self-replicating RNA (A306, 1 µg), self-replicating RNA delivered using electroporation (A306+EP, 1 and 0.1 µg, respectively) and self-replicating RNA formulated with CNE17, CNE05 and CNE35 at an N/P ratio of 10:1 produced as previously described (1 µg or 0.1 µg A306,). Serum SEAP levels (relative light units, RLU) on days 1, 3 and 6 after intramuscular vaccination on day 0 are shown in Table 5. Data are represented as arithmetic mean titers of 5 individual mice per group.

TABLE 5

| Group | Dose (µg) | DAY1 | DAY3 | DAY6 |
| --- | --- | --- | --- | --- |
| VRP | $5 \times 10^5$ IU | 161,428 | 46,594 | 35,998 |
| A306 | 1 | 2,992 | 35,000 | 228,614 |
| CNE17 | 1 | 4,615 | 54,108 | 570,484 |
| CNE17 | 0.1 | 2,509 | 14,772 | 157,386 |
| A306 + EP | 1 | 2,047 | 18,208 | 173,176 |
| A306 + EP | 0.1 | 1,745 | 8,249 | 56,927 |
| CNE05 | 1 | 1,831 | 1,748 | 5,171 |
| CNE35 | 1 | 1,712 | 1,811 | 11,005 |

Table 5 shows that serum SEAP levels increased when the RNA was formulated in CNE17 relative to the naked RNA control at a similar dose. SEAP expression was increase when the RNA was formulated in the CNE relative to the VRP control, but the kinetics of expression was very different. Delivery with electroporation resulted in increased SEAP expression relative to the naked RNA control, but these levels were lower as compared to the SEAP expression level when the RNA was formulated with CNE17. CNE05 and CNE35 reduced protein expression level.

5. Effect of N/P Ratios on SEAP Expression (CNE17)

A306 replicon, which expresses secreted alkaline phosphatase (SEAP), was used to determine the protein expression level in vivo after administration of alphavirus vectors. BALB/c mice, 5 animals per group, were given bilateral intramuscular vaccinations (50 µL per leg) on days 0 with naked self-replicating RNA (A306, 1 µg), self-replicating RNA formulated with CNE17, produced as previously described (A306, 1 µg) at the following N/P ratio's 6:1, 7:1, 8:1, 10:1, 12:1, 13:1, 14:1, 16:1.

Serum SEAP levels (relative light units, RLU) on days 1, 3 and 6 after intramuscular vaccination on day 0 are shown in Table 6. Data are represented as arithmetic mean titers of 5 individual mice per group. A correlation of the heparin sulfate binding compared to day 6 SEAP expression is outlined in Table 7. Percentages of RNA released from the complex at 6x, 8x, and 10x heparin sulfate, respectively, are indicated.

TABLE 6

Serum SEAP levels (CNE17)

| Group | A306 Dose (µg) | DAY1 | DAY3 | DAY6 |
| --- | --- | --- | --- | --- |
| A306 | 1 | 1,235 | 3,271 | 5,215 |
| CNE17 6:1 | 1 | 6,189 | 17,960 | 131,321 |
| CNE17 7:1 | 1 | 2,836 | 40,736 | 266,217 |
| CNE17 8:1 | 1 | 5,737 | 26,823 | 316,274 |
| CNE17 10:1 | 1 | 8,018 | 31,988 | 333,184 |
| CNE17 12:1 | 1 | 7,775 | 23,412 | 295,218 |
| CNE17 13:1 | 1 | 9,217 | 24,236 | 247,262 |
| CNE17 14:1 | 1 | 7,317 | 26,072 | 279,585 |
| CNE17 16:1 | 1 | 15,014 | 17,141 | 144,582 |

TABLE 7

Heparin binding and day 6 SEAP expression (CNE17)

| N/P ratio | 6x heparin Sulfate | 8x heparin Sulfate | 10x heparin Sulfate | Day 6 SEAP expression | Standard Deviation |
| --- | --- | --- | --- | --- | --- |
| 4 | 5.4 | 4.9 | 4.6 | — | — |
| 6 | 7.7 | 16.6 | 32.1 | 131321 | 49229 |
| 7 | 15.2 | 27.1 | 42.8 | 266217 | 190144 |
| 8 | 20.7 | 39.8 | 50.8 | 316274 | 138669 |
| 10 | 53.9 | 72.7 | 79.3 | 333184 | 168456 |
| 12 | 45.4 | 71.7 | 88.8 | 295218 | 153891 |
| 13 | — | — | — | 247262 | 85926 |
| 14 | 13.1 | 84.1 | 81.5 | 279585 | 261205 |
| 16 | 1 | 47.5 | 84.9 | 144583 | 105973 |
| 18 | 0 | 21.1 | 78 | — | — |

Tables 6 and 7 show that serum SEAP levels increased when the RNA was formulated at an N/P ratio of 10:1 relative to the naked RNA control at a similar dose. The other N/P ratio's tested expressed lower amounts of protein expression as compared to the 10:1 N/P ratio, but all showed a higher response than naked RNA. It should be highlighted that the average SEAP values from the naked RNA fluctuated considerably, which is exemplified in Tables 5 and 6, with expression of at approximately 35,000 in one experiment, and 5,000 in another. The protein expression level on day 6 correlated well with the heparin release.

6. Effect of N/P Ratios on SEAP Expression (CNE13)

A306 replicon, which expresses secreted alkaline phosphatase (SEAP), was used to determine the protein expression level in-vivo after administration of alphavirus vectors. BALB/c mice, 5 animals per group, were given bilateral intramuscular vaccinations (50 µL per leg) on days 0 with naked self-replicating RNA (A306, 1 µg), self-replicating RNA formulated with CNE13, produced as previously described (1 µg A306) at the following N/P ratio's 6:1, 8:1, 10:1, 12:1, 14:1, 16:1, 18:1.

Serum SEAP levels (relative light units, RLU) on days 1, 3 and 6 after intramuscular vaccination on day 0 are shown in Table 8. Data are represented as arithmetic mean titers of 5 individual mice per group. A correlation of the heparin sulfate binding compared to day 6 SEAP expression is outlined in Table 9. Percentages of RNA released from the complex at 6x, 8x, and 10x heparin sulfate, respectively, are indicated.

TABLE 8

Serum SEAP levels (CNE13)

| Group | A306 Dose (μg) | DAY1 | DAY3 | DAY6 |
|---|---|---|---|---|
| A306 | 1 | 1,507 | 42,405 | 138,978 |
| CNE13 18:1 | 1 | 5,425 | 169,971 | 1,104,679 |
| CNE13 16:1 | 1 | 3,584 | 68,118 | 586,874 |
| CNE13 14:1 | 1 | 5,199 | 56,314 | 745,815 |
| CNE13 12:1 | 1 | 3,609 | 212,772 | 1,462,864 |
| CNE13 10:1 | 1 | 5,538 | 200,506 | 1,103,004 |
| CNE13 8:1 | 1 | 6,038 | 95,870 | 872,715 |
| CNE13 6:1 | 1 | 4,116 | 23,000 | 291,485 |

TABLE 9

Heparin binding and day 6 SEAP expression (CNE13)

| N/P ratio | 6x heparin Sulfate | 8x heparin Sulfate | 10x heparin Sulfate | Day 6 SEAP expression | Standard Deviation |
|---|---|---|---|---|---|
| 4 | 6.94 | 7.81 | 8.6 | — | — |
| 6 | 10.9 | 13.02 | 14.48 | 291485 | 313966 |
| 8 | 19.33 | 24.44 | 29.01 | 872715 | 530829 |
| 10 | 27.64 | 33.57 | 39.1 | 1103004 | 1095207 |
| 12 | 22.85 | 40.28 | 45.95 | 1462864 | 1413440 |
| 14 | 19.3 | 35.91 | 40.97 | 745815 | 415278 |
| 16 | 6.23 | 34.86 | 42.45 | 586875 | 471111 |
| 18 | 0.71 | 28.32 | 40.47 | 1104680 | 715503 |
| 20 | 0.32 | 13.77 | 42.64 | — | — |

Tables 8 and 9 show that serum SEAP levels increased when the RNA was formulated at all N/P ratio's tested relative to the naked RNA control at similar dose. The protein expression on day 6 correlated well with the heparin release.

7. Effect of NM Ratios on SEAP Expression (CNE01)

A306 replicon, which expresses secreted alkaline phosphatase (SEAP), was used to determine the protein expression level in-vivo after administration of alphavirus vectors. BALB/c mice, 5 animals per group, were given bilateral intramuscular vaccinations (50 μL per leg) on day 0 with naked self-replicating RNA (A306, 1 μg), self-replicating RNA formulated with CNE01, produced as previously described (1 μg A306) at the following N/P ratios 4:1, 10:1, 12:1, 14:1, 16:1, 18:1.

Serum SEAP levels (relative light units, RLU) on days 1, 3 and 6 after intramuscular vaccination on day 0 are shown in Table 10. Data are represented as arithmetic mean relative light units (RLUs) of 5 individual mice per group. A correlation of the heparin sulfate binding compared to day 6 SEAP expression is outlined in Table 11. Percentages of RNA released from the complex at 6×, 8×, and 10× heparin sulfate, respectively, are indicated.

TABLE 10

Serum SEAP levels (CNE01)

| Group | A306 Dose (μg) | DAY1 | DAY3 | DAY6 |
|---|---|---|---|---|
| A306 | 1 | 9,102 | 6,567 | 17,994 |
| CNE01 4:1 | 1 | 4,326 | 8,064 | 104,097 |
| CNE01 10:1 | 1 | 5,865 | 14,058 | 237,271 |
| CNE01 12:1 | 1 | 19,365 | 14,096 | 117,644 |
| CNE01 14:1 | 1 | 4,841 | 11,531 | 148,937 |
| CNE01 16:1 | 1 | 9,061 | 20,639 | 182,854 |
| CNE01 18:1 | 1 | 13,822 | 45,073 | 285,868 |

TABLE 11

Heparin binding and day 6 SEAP expression of CNE01

| N/P ratio | 6x heparin Sulfate | 8x heparin Sulfate | 10x heparin Sulfate | Day 6 SEAP expression | Standard Deviation |
|---|---|---|---|---|---|
| 4 | 59.76 | 66.5 | 69.18 | 104098 | 64504 |
| 6 | 70.66 | 73.36 | 72.05 | — | — |
| 8 | 69.96 | 71.36 | 69.14 | — | — |
| 10 | 66.89 | 66.63 | 63.06 | 237271 | 50946 |
| 12 | 58.91 | 55.05 | 51.42 | 117645 | 64871 |
| 14 | 55.57 | 45.65 | 38.91 | 148938 | 28513 |
| 16 | 52.89 | 39 | 32.36 | 182854 | 36627 |
| 18 | 42.42 | 35.21 | 27.74 | 285868 | 83251 |
| 19 | 30.04 | 40.73 | 27.63 | — | — |

Tables 10 and 11 show that serum SEAP levels increased when the RNA was formulated at all N/P ratio's tested relative to the naked RNA control at similar dose.

Example 3: Assessing Protein Expression Levels Using Different Oils

A series of emulsions were made using different oils but within the base formulation of CNE17, i.e., 5% oil, 0.5% Tween 80, 0.5% span 85 and 1.4 mg/ml DOTAP. Table 12 below outlines the changes in oils for each of the groups. Classifications of the oils are also listed in Table 12.

The emulsions were tested at a 10:1 N/P ratio and was complexed as previously described. BALB/c mice, 5 animals per group, were given bilateral intramuscular vaccinations (50 μL per leg) on day 0 with VRP's expressing SEAP ($5 \times 10^5$ IU), naked self-replicating RNA (A306, 1 μg), self-replicating RNA delivered using electroporation (A306+EP, 1 and 0.1 μg) and self-replicating RNA formulated with CNE36, CNE37, CNE38, and CNE41 produced as previously described (1 μg A306,). Serum SEAP levels (relative light units, RLU) on days 1, 3 and 6 after intramuscular vaccination on day 0 are shown in Table 13. Data are represented as arithmetic mean RLUs of 5 individual mice per group.

TABLE 12

| Emulsion | Type of oil | Source and composition |
|---|---|---|
| CNE17 | Squalene | Shark liver oil, triterpene |
| CNE36 | Soybean oil | Non-animal derived oil, triglycerides made up of alpha-linolenic, linoleic, oleic, stearic and palmitic acids. |
| CNE37 | Cod liver oil | Fish liver oil, high levels of omega-3 fatty acids (eicosapentaenoic acid, decosahexaenoic acid), vit A and vitamin D. |
| CNE38 | Sunflower oil | Non-animal derived oil, primarily linoleic acid triglycerides (~50%), much lesser amounts of oleic, stearic and palmitic acid |
| CNE41 | Olive oil | Non-animal derived oil, triglycerides of oleic, palmitic and other fatty acids |

TABLE 13

| Group | Dose (μg) | DAY1 | DAY3 | DAY6 |
|---|---|---|---|---|
| A306 + EP | 1 | 1,403 | 49,969 | 179,916 |
| CNE36 | 1 | 1,506 | 3,288 | 83,268 |

TABLE 13-continued

| Group | Dose (μg) | DAY1 | DAY3 | DAY6 |
|---|---|---|---|---|
| CNE37 | 1 | 1,387 | 1,127 | 1,594 |
| CNE38 | 1 | 1,791 | 2,228 | 47,705 |
| CNE41 | 1 | 1,369 | 2,113 | 60,039 |
| VRP | 5 × 10^5 IU | 105,829 | 38,546 | 56,155 |
| A306 | 1 | 1,212 | 6,007 | 95,380 |
| A306 + M1F59 | 1 | 1,219 | 1,656 | 11,667 |

As shown in Table 13, CNE17 shows the highest level of expression throughout the studies. All of the other emulsions were inferior to a 1 μg dose of naked RNA. CNE36 resulted in highest expression using the new oils, followed by CNE41 and CNE38. A dose of RNA added directly to MF59 muted the response.

Example 4: CNE17 Enhanced Immunogenicity of RSV-F Antigen in a Mouse Model

1. Methods

Murine Immunogenicity Studies

The A317 replicon that expresses the surface fusion glycoprotein of RSV (RSV-F) was used for this study. BALB/c mice, aged 8-10 weeks and weighing about 20 g, 10 animals per group, were given bilateral intramuscular vaccinations. All animals were injected in the quadriceps in the two hind legs each getting an equivalent volume (50 μL per leg) on days 0 and 21 with VRP's expressing RSV-F ($1\times10^6$ IU), naked self-replicating RNA (A317, 1 μg), self-replicating RNA delivered using electroporation (10 μg A317+EP), or self-replicating RNA formulated in CNE17 (0.1 μg or 1 μg A317). Serum was collected for antibody analysis on days 14 (2wp1), 35 (2wp2) and 49 (4wp2). When measurement of T cell responses was required, spleens were harvested from 5 mice per group at day 35 or 49 for T cell analysis.

Mouse T Cell Function Assays: Intracellular Cytokines Immunofluorescence Assay

Two to five spleens from identically vaccinated BALB/c mice were pooled and single cell suspensions were prepared for culture. Two antigen-stimulated cultures and two unstimulated cultures were established for each splenocyte pool. Antigen-stimulated cultures contained $1\times10^6$ splenocytes, RSV F peptide 85-93 ($1\times10^{-6}$M), RSV F peptide 249-258 ($1\times10^{-6}$ M), RSV F peptide 51-66 ($1\times10^{-6}$ M), anti-CD28 mAb (1 mcg/mL), and Brefeldin A (1:1000). Unstimulated cultures did not contain RSV F peptides, and were otherwise identical to the stimulated cultures. After culturing for 6 hours at 37° C., cultures were processed for immunofluorescence. Cells were washed and then stained with fluorecently labeled anti-CD4 and anti-CD8 monoclonal antibodies (mAb). Cells were washed again and then fixed with Cytofix/cytoperm for 20 minutes. The fixed cells were then washed with Perm-wash buffer and then stained with fluorescently labeled mAbs specific for IFN-g, TNF-a, IL-2, and IL-5. Stained cells were washed and then analyzed on an LSR II flow cytometer. FlowJo software was used to analyze the acquired data. The CD4+8− and CD8+4− T cell subsets were analyzed separately. For each subset in a given sample the % cytokine-positive cells was determined. The % RSV F antigen-specific T cells was calculated as the difference between the % cytokine-positive cells in the antigen-stimulated cultures and the % cytokine-positive cells in the unstimulated cultures. The 95% confidence limits for the % antigen-specific cells were determined using standard methods (Statistical Methods, 7th Edition, G. W. Snedecor and W. G. Cochran).

Mouse T Cell Function Assays: Secreted Cytokines Assay

The cultures for the secreted cytokines assay were similar to those for the intracellular cytokines immunofluorescence assay except that Brefeldin A was omitted. Culture supernatants were collected after overnight culture at 37° C., and were analyzed for multiple cytokines using mouse Th1/Th2 cytokine kits from Meso Scale Discovery. The amount of each cytokine per culture was determined from standard curves produced using purified, recombinant cytokines supplied by the manufacturer.

2. CNE17 Enhanced Immunogenicity of RSV-F Antigen in a Mouse Model

F-specific serum IgG titers on day 14, 35 and 49 are shown in Tables 14, 15 and 16. RSV serum neutralization titers on day 35 and 49 are shown in Table 17 and T cell responses at day 49 are shown in Table 18 and 19.

TABLE 14

F-specific serum IgG titers of mice at day 14

| | 1 μg A317 | 0.1 μg CNE17 | 1 μg CNE17 | 10 μg A317 + EP | 1E6 IU VRP |
|---|---|---|---|---|---|
| | 529 | 2429 | 3373 | 5 | 6041 |
| | 1530 | 2060 | 4417 | 88 | 4912 |
| | 2734 | 2012 | 1927 | 964 | 12923 |
| | 2503 | 1887 | 3597 | 7235 | 7075 |
| | 5539 | 3174 | 5731 | 2558 | 6829 |
| | 1033 | 3904 | 2852 | 5105 | 4885 |
| | 5110 | 1481 | 3739 | 9806 | 3680 |
| | 1106 | 2345 | 4904 | 2787 | 9813 |
| | 1493 | 3084 | 3824 | 2576 | 8631 |
| | 3456 | 2497 | 3004 | 1858 | 6314 |
| GMT | 1980 | 2398 | 3590 | 1180 | 6685 |

Serum was collected for antibody analysis on days 14 (2wp1). Data are represented as individual animals and the geometric mean titers of 10 individual mice per group. If an individual animal had a titer of <25 (limit of detection) it was assigned a titer of 5.

TABLE 15

F-specific serum IgG titers of mice at day 35

| | 1 μg A317 | 0.1 μg CNE17 | 1 μg CNE17 | 10 μg A317 + EP | 1E6 IU VRP |
|---|---|---|---|---|---|
| | 958 | 48079 | 8473 | 14612 | 813045 |
| | 12518 | 17589 | 58556 | 22805 | 365485 |
| | 4839 | 8522 | 12053 | 32156 | 961601 |
| | 10128 | 10985 | 20395 | 24090 | 349215 |
| | 18451 | 30801 | 51514 | 31053 | 297526 |
| | 9805 | 13372 | 26348 | 18105 | 207652 |
| | 19154 | 5137 | 80686 | 23918 | 1580066 |
| | 4490 | 47173 | 21014 | 9091 | 900889 |
| | 14674 | 78232 | 61076 | 21006 | 822285 |
| | 15223 | 24135 | 25499 | 9835 | 587121 |
| GMT | 8532 | 20767 | 29111 | 19117 | 579033 |

Serum was collected for antibody analysis on days 35 (2wp2). Data are represented as individual animals and the geometric mean titers of 10 individual mice per group. If an individual animal had a titer of <25 (limit of detection) it was assigned a titer of 5.

TABLE 16

F-specific serum IgG titers of mice at day 49

|  | 1 µg A317 | 0.1 µg CNE17 | 1 µg CNE17 | 10 µg A317 + EP | 1E6 IU VRP |
|---|---|---|---|---|---|
|  | 958 | 48079 | 8473 | 14612 | 813045 |
|  | 12518 | 17589 | 58556 | 22805 | 365485 |
|  | 4839 | 8522 | 12053 | 32156 | 961601 |
|  | 10128 | 10985 | 20395 | 24090 | 349215 |
|  | 18451 | 30801 | 51514 | 31053 | 297526 |
|  | 9805 | 13372 | 26348 | 18105 | 207652 |
|  | 19154 | 5137 | 80686 | 23918 | 1580066 |
|  | 4490 | 47173 | 21014 | 9091 | 900889 |
|  | 14674 | 78232 | 61076 | 21006 | 822285 |
|  | 15223 | 24135 | 25499 | 9835 | 587121 |
| GMT | 8532 | 20767 | 29111 | 19117 | 579033 |

Serum was collected for antibody analysis on days 49 (4wp2). Data are represented as individual animals and the geometric mean titers of 10 individual mice per group. If an individual animal had a titer of <25 (limit of detection) it was assigned a titer of 5.

TABLE 17

RSV serum neutralization titers

| | A317, 1 µg | | CNE17, 0.1 µg | | CNE17, 1 µg | | VRP 1E6 IU | |
|---|---|---|---|---|---|---|---|---|
| | 2wp2 | 4wp2 | 2wp2 | 4wp2 | 2wp2 | 4wp2 | 2wp2 | 4wp2 |
| | NA | <40 | NA | <40 | NA | <40 | 265 | 161 |
| | NA | <40 | NA | <40 | NA | 70 | 73 | 64 |
| | NA | <40 | NA | <40 | NA | <40 | 77 | 126 |
| | NA | <40 | NA | <40 | NA | 76 | 140 | 151 |
| | NA | <40 | NA | 42 | NA | 57 | 290 | 194 |
| | NA | <40 | NA | 52 | NA | <40 | 134 | 123 |
| | NA | <40 | NA | <40 | NA | <40 | 466 | 1033 |
| | NA | <40 | NA | 173 | NA | <40 | 127 | 174 |
| | NA | <40 | NA | <40 | NA | <40 | 75 | 122 |
| | NA | <40 | NA | <40 | NA | <40 | 77 | 76 |
| GMT | NA | <40 | NA | 29 | NA | 34 | 139 | 155 |

Serum was collected for analysis on days 35 (2wp2) and 49 (4wp2). Data are represented as 60% plaque reduction neutralization titers of individual mice and the geometric mean titer of 10 individual mice per group. If an individual animal had a titer of <40 (limit of detection) it was assigned a titer of 20. NA=not assayed.

TABLE 18

Frequencies of RSV F-specific CD4+ splenic T cells on day 49 (4wp2)

| 4wp2 splenic T cell responses | CD4+CD8−: F51-66 peptide restimulation | | | |
|---|---|---|---|---|
| | IFNg+ | IL2+ | IL5+ | TNFa+ |
| VRP 1E6 IU | 0.07 ± 0.06 | 0.04 ± 0.05 | 0.00 ± 0.02 | 0.10 ± 0.04 |
| 1 µg A317 | 0.00 ± 0.05 | 0.05 ± 0.04 | 0.00 ± 0.01 | 0.03 ± 0.02 |
| CNE17, 1 µg | 0.00 ± 0.05 | 0.04 ± 0.04 | 0.00 ± 0.01 | 0.05 ± 0.02 |
| CNE17, 0.1 µg | 0.00 ± 0.05 | 0.02 ± 0.04 | 0.00 ± 0.01 | 0.02 ± 0.02 |
| 10 µg A317 + EP | 0.02 ± 0.06 | 0.04 ± 0.04 | 0.01 ± 0.01 | 0.05 ± 0.03 |
| none | 0.04 ± 0.06 | 0.00 ± 0.05 | 0.00 ± 0.02 | 0.00 ± 0.01 |

Shown are net (antigen-specific) cytokine-positive frequency (%)±95% confidence half-interval. Net frequencies shown in bold indicate stimulated responses that were statistically significantly >0.

TABLE 19

Frequencies of RSV F-specific CD8+ splenic T cells on day 49 (4wp2)

| 4wp2 splenic T cell responses | CD8+CD4−: F85-93, F249-258 peptide restimulation | | | |
|---|---|---|---|---|
| | IFNg+ | IL2+ | IL5+ | TNFa+ |
| VRP 1E6 IU | 3.48 ± 0.29 | 1.21 ± 0.18 | −0.03 ± 0.05 | 3.31 ± 0.28 |
| 1 µg A317 | 0.74 ± 0.15 | 0.46 ± 0.11 | −0.03 ± 0.04 | 0.70 ± 0.14 |
| CNE17, 1 µg | 1.25 ± 0.17 | 0.60 ± 0.12 | 0.01 ± 0.03 | 1.15 ± 0.16 |
| CNE17, 0.1 µg | 0.89 ± 0.15 | 0.49 ± 0.11 | −0.03 ± 0.04 | 0.83 ± 0.14 |
| 10 µg A317 + EP | 0.85 ± 0.15 | 0.53 ± 0.11 | 0.01 ± 0.04 | 0.72 ± 0.15 |
| none | 0.01 ± 0.07 | 0.00 ± 0.05 | −0.02 ± 0.05 | 0.02 ± 0.06 |

Shown are net (antigen-specific) cytokine-positive frequency (%)±95% confidence half-interval. Net frequencies shown in bold indicate stimulated responses that were statistically significantly >0.

As shown in Tables 14-19, CNE17 formulation enhanced immunogenicity, as determined by increased F-specific IgG titers (5-fold increase 4wp2), neutralization titers, and CD4 and CD8 T cell responses, relative to the naked RNA control. Electroporation of RNA enhanced immunogenicity relative to the naked RNA control, but was lower than CNE17 delivery. Importantly, the immune responses elicited in CNE17 groups fluctuated much less as compared to that of naked RNA. For example, the day 14 samples from the naked self replicating RNA group gave antibody titers between 529 and 5110, whereas RNA samples formulated with CNE17 at a 1 µg dose gave antibody titers between 1927 and 5731. Additionally, all animals in the CNE17 group responded with a robust response and boosted very well. In contrast, some animals in the naked RNA group that did not boost significantly.

Example 5: Immunogenicity of the RNA-Particle Complexes in a Rat Model

1. Methods
RSV-F Trimer Subunit Vaccine

The RSV F trimer is a recombinant protein comprising the ectodomain of RSV F with a deletion of the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed in insect cells and purified by virtue of a HIS-tagged in fusion with the construct's C-terminus followed by size exclusion chromatography using conventional techniques. The resulting protein sample exhibits greater than 95% purity. For the in vivo evaluation of the F-subunit vaccine, 100 µg/mL trimer protein was adsorbed on 2 mg/mL alum using 10 mM Histidine buffer, pH 6.3 and isotonicity adjusted with sodium chloride to 150 mM. F-subunit protein was adsorbed on alum overnight with gentle stirring at 2-8° C.

Vaccination and Challenge of Cotton Rats

Female cotton rats (Sigmodon hispidis) were obtained from Harlan Laboratories. All studies were approved and performed according to Novartis Animal Care and Use Committee. Groups of animals were immunized intramuscularly (i.m., 100 µl) with the indicated vaccines on days 0 and 21. Serum samples were collected 3 weeks after the first immunization and 2 weeks after the second immunization. Immunized or unvaccinated control animals were challenged intranasally (i.n.) with $1 \times 10^5$ PFU RSV 4 weeks after the final immunization. Blood collection and RSV challenge were performed under anesthesia with 3% isoflurane using a precision vaporizer.

RSV F-Specific ELISA

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (delp23-furdel-trunc uncleaved) in PBS. After washing (PBS with 0.1% Tween-20), plates were blocked with Superblock Blocking Buffer in PBS (Thermo Scientific) for at least 1.5 hr at 37° C. The plates were then washed, serial dilutions of serum in assay diluent (PBS with 0.1% Tween-20 and 5% goat serum) from experimental or control cotton rats were added, and plates were incubated for 2 hr at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to a standard, pooled sera from RSV-infected cotton rats with a defined titer of 1:2500, that was included on every plate).

Micro Neutralization Assay

Serum samples were tested for the presence of neutralizing antibodies by a plaque reduction neutralization test (PRNT). Two-fold serial dilutions of HI-serum (in PBS with 5% HI-FBS) were added to an equal volume of RSV Long previously titered to give approximately 115 PFU/25 µl. Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hr at 37° C. and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

Viral Load

Viral load in the lung was determined by plaque assay. Specifically, lungs were harvested 5 days post RSV infection and one right lobe was placed into 2.5 ml Dulbecco's Modified Eagle Medium (DMEM, Invitrogen) with 25% sucrose and disrupted with a tissue homogenizer. Cell-free supernatants from these samples were stored at −80° C. To assay for infectious virus, dilutions of clarified lung homogenate (in PBS with 5% heat-inactivated fetal bovine serum, HI-FBS) were inoculated on confluent HEp-2 cell monolayers in a volume of 200 µl/well of a 12-well plate. After 2 hrs with periodic gentle rocking (37° C., 5% $CO_2$), the inoculum was removed, and cells were overlaid with 1.5 ml of 1.25% SeaPlaque agarose (Lonza) in Eagle's Minimal Essential Medium (EMEM, Lonza) supplemented with 5% HI-FBS, glutamine, and antibiotics. After 3-4 days of incubation, cells were again overlaid with 1 ml of 1.25% agarose in EMEM (Sigma) containing 0.1% neutral red (Sigma). Plaques are counted one day later with the aid of a light box.

Cotton Rat Lung Pathology

Five days after RSV challenge lungs were harvested and 4 lobes from each animal were collected and fixed with 10% neutral buffered formalin (NBF) by gentle intratracheal instillation followed by immersion fixation. Tissues were processed routinely to prepare hematoxylin & eosin-stained sections for microscopic examination. Findings were evaluated using a modification of previously published criteria [Prince G A, et al., 2001] for the following parameters: peribronchiolitis, alveolitis, bronchitis, perivascular cellular infiltrates, and interstitial pneumonitis. Lesions were graded on a 4-point semiquantitative scale. Minimal (+) change contained one or a few small foci; mild (++) change was composed of small- to medium-size foci; moderate (+++) change contained frequent and/or moderately-sized foci; and marked (++++) change showed extensive to confluent foci affecting most/all of the tissue.

2. Cotton Rat RSV Challenge Study

A317 replicon, which expresses the surface fusion glycoprotein of RSV (RSV-F) was used for this study. Cotton rats (Sigmodon hispidus), 8 animals per group, were given bilateral intramuscular vaccinations (50 µL per leg) on days 0 and 21 with naked self-replicating RNA (A317, 1 µg or 10 µg), self-replicating RNA formulated with CNE17 (A317, 0.1 µg or 1 µg), VRPs ($5 \times 10^6$ IU) expressing RSV-F, F-trimer/alum subunit (10 µg), or formalin inactivated RSV vaccine (5200 FI-pfu). Serum was collected for antibody analysis on days 14 (2wp1) and 35 (2wp2). All animals were challenged with $1 \times 10^5$ pfu RSV intranasally on day 49 and lungs were collected on day 54 (5dpc) for determination of viral load and lung pathology.

F-specific serum IgG titers on day 14 and 35 are shown in Table 20; individual antibody titers for 8 animals from selected groups at 2wp2 are shown in Table 21; RSV serum neutralization titers on days 14 and 35 are shown in Table 22; lung viral titers 5 days post RSV challenge are shown in Table 23; and Lung alveolitis scores 5 days post RSV challenge are shown in Table 24.

TABLE 20

| F-specific serum IgG titers of cotton rats (Sigmodon hispidus) | | | |
|---|---|---|---|
| vaccine | dose | F-specific IgG 2wp1 | F-specific IgG 2wp2 |
| Naked A317 | 10 µg | 198 | 1599 |
| Naked A317 | 1 µg | 78 | 526 |
| CNE17 | 1 µg | 408 | 4918 |
| CNE17 | 0.1 µg | 325 | 2512 |
| VRP | 5 × 106 IU | 961 | 5864 |
| F-trimer/alum | 10 µg | 3526 | 111893 |
| FI-RSV | 5200 FI-pfu | 17 | 2074 |
| none | | 5 | 5 |

8 animals per group, after intramuscular vaccinations on days 0 and 21. Serum was collected for antibody analysis on days 14 (2wp1) and 35 (2wp2), all animals were challenged with $1 \times 10^5$ pfu RSV intranasally on day 49. Lungs were collected on day 54 (5dpc) for determination of viral load and lung pathology. Data are represented as geometric mean titers of 8 individual cotton rats per group. If an individual animal had a titer of <25 (limit of detection) it was assigned a titer of 5.

TABLE 21

Individual antibody titers at 2wp2

| 10 μg A317 | 1 μg A317 | 0.1 μg CNE17 | 1 μg CNE17 |
|---|---|---|---|
| 1778 | 612 | 3967 | 3740 |
| 1534 | 409 | 2360 | 3199 |
| 3144 | 1039 | 1786 | 3998 |
| 1174 | 116 | 3097 | 7173 |
| 1719 | 1086 | 1075 | 9005 |
| 488 | 869 | 2956 | 6170 |
| 1586 | 742 | 1496 | 6406 |
| 3200 | 276 | 6431 | 2800 |

Individual antibody titers for 8 animals from selected groups (naked RNA and CNE formulated RNA).

TABLE 22

RSV serum neutralization titers of cotton rats (Sigmodon hispidus)

| vaccine | dose | PRNT60 2wp1 | PRNT60 2wp2 |
|---|---|---|---|
| Naked A317 | 10 μg | 78 | 240 |
| Naked A317 | 1 μg | 58 | 70 |
| CNE17 | 1 μg | 91 | 269 |
| CNE17 | 0.1 μg | 63 | 145 |
| VRP | 5 × 10⁶ IU | 149 | 683 |
| F-trimer/alum | 10 μg | 142 | >5120 |
| FI-RSV | 5200 FI-pfu | 28 | 38 |
| none | | 30 | <20 |

8 animals per group, after intramuscular vaccinations on days 0 and 21. Serum was collected for analysis on days 14 (2wp1) and 35 (2wp2). Data are represented as 60% plaque reduction neutralization titers. Geometric mean titer of 2 pools of 4 cotton rats per group. If an individual animal had a titer of <25 (limit of detection) it was assigned a titer of 5.

TABLE 23

Lung viral titers 5 days post RSV challenge of cotton rats (Sigmodon hispidus)

| vaccine | dose | pfu/g lung 5 dpc |
|---|---|---|
| Naked A317 | 10 μg | 397 |
| Naked A317 | 1 μg | 659 |
| CNE17 | 1 μg | 414 |
| CNE17 | 0.1μg | 572 |
| VRP | 5 × 106 IU | 359 |
| F-trimer/alum | 10 μg | 190 |
| FI-RSV | 5200 FI-pfu | 5248 |

8 animals per group, after intramuscular vaccinations on days 0 and 21. Serum was collected for analysis on days 14 (2wp1) and 35 (2wp2). Data are represented as 60% plaque reduction neutralization titers. Geometric mean titer of 2 pools of 4 cotton rats per group. If an individual animal had a titer of <25 (limit of detection) it was assigned a titer of 5.

TABLE 24

Lung alveolitis 5 days post RSV challenge of cotton rats (Sigmodon hispidus)

| | | # of cotton rats with indicated alveolitis score | | | | |
|---|---|---|---|---|---|---|
| vaccine | dose | 0 | 1 | 2 | 3 | 4 |
| Naked A317 | 10 μg | 8 | | | | |
| Naked A317 | 1 μg | 8 | | | | |
| CNE17 | 1 μg | 8 | | | | |
| CNE17 | 0.1 μg | 7 | 1 | | | |
| VRP | 5 × 10⁶ IU | 3 | 4 | 1 | | |
| F-trimer/alum | 10 μg | 7 | 1 | | | |
| FI-RSV | 5200 FI-pfu | 1 | 4 | 3 | | |
| none (challenged) | | 5 | 3 | | | |

8 animals per group, after intramuscular vaccinations on days 0 and 21. All animals were challenged with $1\times10^5$ pfu RSV intranasally on day 49. Lungs were collected on day 54 (5dpc) for determination of viral load and lung pathology. Lesions were graded on a 4-point semiquantitative scale. Minimal (1) change contained one or a few small foci; mild (2) change was composed of small- to medium-size foci; moderate (3) change contained frequent and/or moderately-sized foci; and marked (4) change showed extensive to confluent foci affecting most/all of the tissue.

This study shows the immunogenicity and protective capacity of replicon RNA in the cotton rat RSV model. Unformulated replicon RNA induced serum F-specific IgG and RSV neutralizing antibodies after one vaccination, and that these responses were boosted by a second vaccination. CNE was effective in this model, boosting F-specific IgG titers to 1 μg replicon RNA approximately 9-fold and neutralization titers by 4-fold after the second vaccination. Additionally, CNE17 reduced the considerable variations of the immune responses that were observed when naked RNA was used, regardless of the doses (0.1 or 1 μg), and all animals responded to vaccination. All replicon RNA vaccines provided protection from a nasal RSV challenge, reducing the lung viral load 5 days post RSV challenge more than 3 orders of magnitude. The magnitude and protective capacity of the immune response generated by 1 μg replicon RNA formulated with CNE was within 2-fold the response elicited by $5\times10^6$ VRPs.

Example 6: The Effect of Particle Size on Immunogenicity

This example shows that particle size affects the immunogenicity of the CNE/RNA formulations.

Protocols for particle size assay and in vivo SEAP assay are described in Example 2. Protocols for murine immunogenicity studies are described in Example 3. FIG. 8A shows the results (arithmetic mean) of the in vivo SEAP assay. FIG. 8B shows the total IgG titers of individual animals in the BALB/c mice at 2wp1 and 2wp2 time points.

RNA complexation with CNE17 increased particle size from about 220 nm to about 300 nm (data not shown). As shown in FIGS. 8A and 8B, as particle size increased, the expression levels of SEAP were reduced, and the host immune responses were also decreased.

Example 7: Assessing the Effects of Alternative Cationic Lipids on Immunogenicity 1. Materials and Methods.
Preparation of CNEs A series of emulsions were made using the following cationic lipids: DLinDMA, DOTMA, DOEPC, DSTAP, DODAC, and DODAP. Table 25 describes the components of the emulsions.

CNEs were prepared according the protocols described in Example 1. The RNA/CNE complexes were prepared according the protocols described in Example 2.

TABLE 25

| CNE | Cationic Lipid (+) | mg/ml +Lipid | Surfactant | Squalene | Buffer/water |
|---|---|---|---|---|---|
| CMF20 | DLinDMA | 1.25 | 0.5% SPAN 85<br>0.5% Tween 80 | 4.3% | 10 mM citrate buffer pH 6.5<br>(in RNase-free dH$_2$O, no DCM) |
| CMF21 | DLinDMA | 1.25 | 0.5% SPAN 85<br>0.5% Tween 80 | 4.3% | 10 mM citrate buffer pH 6.5<br>(in RNase-free dH$_2$O, & 50° C. heat & sonication to solubilize; solvent evaporated post 1st homogenization) |
| CMF36 | DODAP | 1.3 | 0.5% SPAN 85<br>0.5% Tween 80 | 4.3% | 10 mM citrate buffer pH 6.5<br>(in RNase-free dH$_2$O, CHCl$_3$; solvent evaporated prior to homogenization) |
| CMF37 | DOTMA | 1.35 | 0.5% SPAN 85<br>0.5% Tween 80 | 4.3% | 10 mM citrate buffer pH 6.5<br>(in RNase-free dH$_2$O, no DCM) |
| CMF38 | DOEPC | 1.7 | 0.5% SPAN 85<br>0.5% Tween 80 | 4.3% | 10 mM citrate buffer pH 6.5<br>(in RNase-free dH$_2$O, no DCM) |
| CMF39 | DDA | 1.65 | 0.5% SPAN 85<br>0.5% Tween 80 | 4.3% | 10 mM citrate buffer pH 6.5<br>(in RNase-free dH$_2$O, solvent evaporated post 1st homogenization) |
| CMF42 | DSTAP | 1.4 | 0.5% SPAN 85<br>0.5% Tween 80 | 4.3% | 10 mM citrate buffer pH 6.5<br>(in RNase-free dH$_2$O, DCM and methanol; solvents evaporated prior to homogenization) |
| CMF43 | DODAC | 1.17 | 0.5% SPAN 85<br>0.5% Tween 80 | 4.3% | 10 mM citrate buffer pH 6.5<br>(in RNase-free dH$_2$O, no DCM) |

Murine Immunogenicity Studies

The emulsions were tested at 10:1 N/P, 12:1 N/P or 18:1 N/P ratios (see Table 26). Then RNA replicon and the emulsions were complexed as previously described in Example 2. BALB/c mice, 5-10 animals per group, were given bilateral intramuscular vaccinations (50 μL per leg) on days 0 with naked self-replicating RNA (A317, 1 μg), RV01(15) (1 μg of A317 formulated in a liposome that contained 40% DlinDMA, 10% DSPC, 48% Chol, 2% PEG DMG 2000), self-replicating RNA (A317, 1 μg) formulated with CNE13, CNE17, CMF37, CMF38, or CMF42.

2. CNE-Formulated RNA Enhanced Immunogenicity of RSV-F Antigen in a Mouse Model

Total serum IgG titers (Geometric Mean Titers) from the groups of BALB/c mice on day 14 and 35 are shown in Table 26 (groups 1-8). CMF37 (DOTMA)-formulated RNA enhanced host immune response well, and the IgG titers were comparable to that CNE17 (DOTAP). CMF38 (DOEPC)-formulated RNA elicited a slightly higher IgG titer than that of CNE17, but the enhancement was not statistically significant. DSTAP-formulated RNA did not significantly enhance host immune response, and the low IgG titers were likely due to the low solubility of DSTAP in squalene. CNE13-formulated RNA enhanced IgG titers about 1.5-fold greater than that of liposome (DDA)-formulated RNA. Total antibody titers induced by CMF43 (DODAC)-formulated RNA were lower than that of CNE17 (Table 28, Groups 7 and 8).

TABLE 26

| | Description | | | | |
|---|---|---|---|---|---|
| Group # | Emulsion | N:P ratio | 2wp1 | 2wp2 | 2wp2/2wp1 ratio |
| 1 | 1ug vA317 | — | 77 | 1,710 | 22.2 |
| 2 | RV01(15) | — | 3,441 | 59,557 | 17.3 |
| 3 | CNE17 DOTAP | 10:1 | 1,474 | 6,512 | 4.4 |
| 4 | CNE13 DDA | 18:1 | 482 | 8,385 | 17.4 |

TABLE 26-continued

| | Description | | | | |
|---|---|---|---|---|---|
| Group # | Emulsion | N:P ratio | 2wp1 | 2wp2 | 2wp2/2wp1 ratio |
| 5 | CMF37 DOTMA | 10:1 | 474 | 6,556 | 13.8 |
| 6 | CNE16 DOEPC | 12:1 | 1,145 | 9,673 | 8.4 |
| 7 | CMF42 DSTAP | 10:1 | 22 | 148 | 6.7 |
| 8 | DDA Liposomes | 18:1 | 898 | 5,333 | 5.9 |
| 9 | CNE17 with 300 mM Trehalose | 10:1 | 1,807 | 6,445 | 3.6 |
| 10 | CNE17 with 300 mM Sucrose | 10:1 | 1,042 | 5,515 | 5.3 |

TABLE 26-continued

| Group # | Emulsion | N:P ratio | 2wp1 | 2wp2 | 2wp2/2wp1 ratio |
|---|---|---|---|---|---|
| 11 | CNE17 with 300 mM Sorbitol | 10:1 | 1,209 | 8,874 | 7.3 |
| 12 | CNE17 with 300 mM Dextrose | 10:1 | 1,247 | 7,956 | 6.4 |

Groups 1-8 had 5 animals/group, and groups 9-12 had 10 animals/group.

Example 8: Assessing the Effects of Buffer Compositions on Immunogenicity

In this example, various emulsions based on CNE17 but with different buffer components were prepared. Table 27 shows the compositions of the buffer-modified emulsions.

TABLE 27

| Base Emulsion | Buffer/water |
|---|---|
| CNE17: 4.3% Squalene, 0.5% SPAN 85, 0.5% Tween 80, 1.4 mg/ml DOTAP | 0 mM citrate buffer (in RNase-free dH$_2$O, no DCM) |
| CNE17: 4.3% Squalene, 0.5% SPAN 85, 0.5% Tween 80, 1.4 mg/ml DOTAP | 1 mM citrate buffer (in RNase-free dH$_2$O, no DCM) |
| CNE17: 4.3% Squalene, 0.5% SPAN 85, 0.5% Tween 80, 1.4 mg/ml DOTAP | 5 mM citrate buffer (in RNase-free dH$_2$O, no DCM) |
| CNE17: 4.3% Squalene, 0.5% SPAN 85, 0.5% Tween 80, 1.4 mg/ml DOTAP | 10 mM citrate buffer pH 6.5 300 mM Trehalose |
| CNE17: 4.3% Squalene, 0.5% SPAN 85, 0.5% Tween 80, 1.4 mg/ml DOTAP | 10 mM citrate buffer pH 6.5 300 mM Sucrose |
| CNE17: 4.3% Squalene, 0.5% SPAN 85, 0.5% Tween 80, 1.4 mg/ml DOTAP | 10 mM citrate buffer pH 6.5 300 mM Sorbitol |
| CNE17: 4.3% Squalene, 0.5% SPAN 85, 0.5% Tween 80, 1.4 mg/ml DOTAP | 10 mM citrate buffer pH 6.5 300 mM Dextrose |

In vitro binding assay showed that reducing the concentration of citrate buffer caused RNA to bind more tightly (data not shown).

Results from murine immunogenicity studies showed that adding sugars to CNE17 did not significantly impact the immunogenicity of the CNE17-formulated RNA (Table 26, groups 9-12)). Slight increases in IgG titers were observed with the addition of sorbitol and dextrose.

Table 28 summarizes the results of murine immunogenicity studies when CNE17-formulated RNAs were prepared using different buffer systems.

TABLE 28

| Group # | RNA | Emulsion | N:P ratio | 2wp1 | 2wp2 | 2wp2/2wp1 ratio |
|---|---|---|---|---|---|---|
| 1 | 1 μg RSV-F* | PBS | — | 100 | 2269 | 23 |
| 2 | RV01(15) | PBS | — | 8388 | 105949 | 13 |
| 3 | 1 μg RSV-F* | CNE17 with 280 mM Sucrose | 10:1 | 898 | 9384 | 10 |
| 4 | 1 μg RSV-F** | CNE17 with 280 mM sucrose, 10 mM NaCl, 1 mM Citrate, | 10:1 | 1032 | 3184 | 3.1 |
| 5 | | CNE17 with 280 mM sucrose, 10mM NaCl, 1 mM Citrate, 0.5% (w/v) and Pluronic F127 | 10:1 | 79 | 895 | 11.3 |

*vA375 replicon,
**vA317 replicon.
Replicons were Ambion transcribed in HEPES buffer, then (i) LiCl precipitated, (ii) capped in Tris buffer, and (iii) LiCl precipitated.
All groups had 8 animals/group.

Different buffer compositions also affected particle size. As shown in FIG. 9, addition of sugar (sucrose) decreased the particle size of the RNA/CNE complex (FIG. 9A); addition of low concentrations of NaCl (at 10 mM) also decreased the particle size of the RNA/CNE complex (FIG. 9A). Citrate buffer did not affect the particle size of the RNA/CNE complex (FIG. 9B).

The effects of polymers on particle size are shown in FIG. 9C. In particular, addition of 0.5% pleuronic F127 to RNA buffer reduced the particle size of the RNA/CNE complex to the pre-complexation size (CNE particles without RNA).

The total antibody titers and neutralizing antibody titers of CNE17 in preferred buffer systems, 280 mM sucrose, 10 mM NaCL, and 1 mM Citrate; or 280 mM sucrose, 10 mM NaCl, 1 mM Citrate, and 0.5% (w/v) Pluronic F127, are shown in Table 28 (Groups 4 and 5).

Example 9: Assessing the Effects of PEG-Lipids on Immunogenicity

In this example, a series of emulsions were made using PEG-lipids. Table 29 shows the compositions of these PEG-lipid based emulsions.

TABLE 29

| CNE | Cationic Lipid (+) | mg/ml +Lipid | PEG-lipid | Squalene | Buffer/water |
|---|---|---|---|---|---|
| CMF22 | DOTAP | 1.4 | PEG2K C18-1 10 mg/mL | 4.3% | 10 mM citrate buffer pH 6.5 (in RNase-free dH$_2$O) |
| CMF23 | DOTAP | 1.4 | PEG2K C18-1 5 mg/mL | 4.3% | 10 mM citrate buffer pH 6.5 (in RNase-free dH$_2$O) |
| CMF24 | DOTAP | 1.4 | PEG2K C14 9.6 mg/mL | 4.3% | 10 mM citrate buffer pH 6.5 (in RNase-free dH$_2$O) |
| CMF25 | DOTAP | 1.4 | PEG2K C14 19.25 mg/mL | 4.3% | 10 mM citrate buffer pH 6.5 (in RNase-free dH$_2$O) |
| CMF26 | DOTAP | 1.4 | PEG2K C18-1 0.7 mg/mL | 4.3% | 10 mM citrate buffer pH 6.5 (in RNase-free dH$_2$O) |
| CMF27 | DOTAP | 1.4 | PEG2K C18-1 1.4 mg/mL | 4.3% | 10 mM citrate buffer pH 6.5 (in RNase-free dH$_2$O) |
| CMF28 | DOTAP | 1.4 | PEG2K C14 0.7 mg/mL | 4.3% | 10 mM citrate buffer pH 6.5 (in RNase-free dH$_2$O) |
| CMF29 | DOTAP | 1.4 | PEG2K C14 1.4 mg/mL | 4.3% | 10 mM citrate buffer pH 6.5 (in RNase-free dH$_2$O) |

For all of the emulsion, a stock solution of 10 mg/mL DOTAP in DCM were used, and the solvent was evaporated after the 1st homogenization. Murine immunogenicity studies were carried out as described above in Example 7.

Table 30 shows the pooled antibody titers at the 2wp1 and 4wp2 time points. For the CNE13 group, the average of individual animal titers, and the geo mean titers are shown. As shown in Table 30, emulsions made with PEG-lipids were effective in inducing immune response against the RSV-F antigen, but the total antibody titers were at a lower level as compared to CNE17-formulated RNA. In addition, increasing the concentration of the PEG-lipids led to a decrease in antibody titers.

TABLE 30

| Group | RNA | Formulation | 2wp1 pooled titer | 4wp2 pooled titer |
|---|---|---|---|---|
| 1 | 1 µg | none | 780 | 2794 |
| 2 | RSV-F* | CNE17 (10:1 N/P ratio) | 1,783 | 12907 |
| 3 | | CMF26 (6:1 N/P ratio), (0.7mg/mL 2K PEG C18-1) | 323 | 4661 |
| 4 | | CMF26 (10:1 N/P ratio), (0.7mg/mL 2K PEG C18-1) | 336 | 6588 |
| 5 | | CMF27 (6:1 N/P ratio), (1.4 mg/mL 2K PEG C18-1) | 209 | 2119 |
| 6 | | CMF27 (10:1 N/P ratio), (1.4 mg/mL 2K PEG C18-1) | 525 | 3770 |
| 7 | | CMF28 (6:1 N/P ratio), (0.7 mg/mL 2K PEG C14) | 906 | 6923 |
| 8 | | CMF28 (10:1 N/P ratio), (0.7 mg/mL 2K PEG C14) | 1,280 | 5532 |
| 9 | | CMF29 (6:1 N/P ratio), (1.4 mg/mL 2K PEG C14) | 159 | 1603 |
| 10 | | CMF29 (10:1 N/P ratio), (1.4 mg/mL 2K PEG C14) | 110 | 4041 |
| 11 | | CNE13 (18:1 N/P ratio) | 3,026 (average); 2891 (GMT) | 25,738 (average); 23068 (GMT) |

*vA317 replicon Groups 1-10 had 5 animals/group and group 11 had 10 animals/group.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A composition comprising an RNA molecule complexed with a particle of a cationic oil-in-water emulsion,
  wherein the particle comprises (a) an oil core that is in liquid phase at 25° C., and (b) a cationic lipid, such that the overall net charge of the emulsion particle prior to RNA complexation is positive, and
  wherein said RNA encodes a protein antigen and said RNA is anchored to the surface of said particle by non-covalent interactions;
  wherein, when administered in an effective amount to a mammal, the composition elicits antibody titers to the antigen equal to or greater than the RNA administered to the mammal not complexed with the particle, further wherein the RNA does not include modified nucleobases, other than an optional 5' cap.

2. The composition of claim 1, wherein the particle further comprises a surfactant.

3. The composition of claim 2, wherein the surfactant is a nonionic surfactant.

4. The composition of claim 3, wherein the surfactant is sorbitan trioleate, polysorbate 80, or a combination thereof.

5. The composition of claim 3, wherein the cationic oil-in-water emulsion comprises from about 0.01% to about 2.5% (v/v) nonionic surfactant.

6. The composition of claim 1, wherein the composition comprises from about 0.2% to about 9% (v/v) of said oil.

7. The composition of claim 1, wherein the oil core comprises Soybean oil, Sunflower oil, Olive oil, Squalene, Squalane or combinations thereof.

8. The composition of claim 1, wherein the cationic lipid is selected from the group consisting of: 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-

Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), and 1,2-dioleoyl-3-dimethylammonium-propane (DODAP), 1,2-dilinoleyloxy-3-dimethylaminopropane (DLinDMA).

9. The composition of claim 1, wherein the cationic lipid is 1,2-dioleoyloxy-3-(trimethylammonio)propane (DOTAP).

10. The composition of claim 9, wherein the cationic oil-in-water emulsion comprises from about 0.5 mg/ml to about 5 mg/ml DOTAP.

11. The composition of claim 1, wherein the cationic lipid is 3β-[N—(N',N'-Dimethylaminoethane)-carbamoyl]Cholesterol (DC Cholesterol) or dimethyldioctadecylammonium (DDA).

12. The composition of claim 11, wherein the composition comprises from about 0.1 mg/ml to about 5 mg/ml DC Cholesterol or DDA.

13. The composition of claim 1, wherein the cationic lipid is N-[1-(2, 3-dioleyloxy)propyl]-N,N,N-trimethylammonium chloride (DOTMA), 1,2-dioleoyl-sn-glycero-3-ethylphosphocholine (DOEPC), or N,N-dioleoyl-N,N-dimethylammonium chloride (DODAC).

14. The composition of claim 13, wherein the composition comprises from about 0.5 mg/ml to about 5 mg/ml DOTMA, DOEPC, or DODAC.

15. The composition of claim 1, wherein the cationic oil-in-water emulsion further comprises a polymer or a surfactant in the aqueous phase of the emulsion.

16. The composition of claim 15, wherein the polymer is a poloxamer, which is present at from about 0.1% to about 10% (v/v).

17. The composition of claim 1, wherein the average diameter of the emulsion particles is from about 80 nm to about 180 nm, and the N/P ratio of the emulsion is at least 4:1.

18. The composition of claim 1, wherein the composition is buffered and has a pH of about 6.0 to about 8.0.

19. The composition of claim 18, wherein the pH is about 6.2 to about 6.8.

20. The composition of claim 18, wherein the composition further comprises an inorganic salt, and the concentration of inorganic salt is no greater than 30 mM.

21. The composition of claim 1, wherein the composition further comprises a nonionic tonicifying agent.

22. The composition of claim 21, wherein the nonionic tonicifying agent is selected from the group consisting of a sugar, a sugar alcohol and combinations thereof.

23. The composition of claim 22, wherein the nonionic tonicifying agent is present in a concentration of about 280 mM to about 300 mM.

24. The composition of claim 21, wherein the composition is isotonic.

25. A method of generating an immune response in a subject, comprising administering to a subject in need thereof a therapeutically effective amount of the composition of claim 1.

26. A composition comprising an RNA molecule complexed with a particle of a cationic oil-in-water emulsion, wherein the particle comprises (a) an oil core that is in liquid phase at 25° C., and (b) a cationic lipid, such that the overall net charge of the emulsion particle prior to RNA complexation is positive, and wherein said RNA molecule encodes a protein antigen and said RNA is anchored to the surface of said particle by non-covalent interactions, wherein, when administered in an effective amount to a mammal, the composition elicits antibody titers to the antigen equal to or greater than the RNA administered to the mammal: i) not complexed with the particle and ii) at a 10-fold higher concentration, relative to the complexed RNA, further wherein the RNA does not include modified nucleobases, other than an optional 5' cap.

27. A composition comprising an RNA molecule complexed with a particle of a cationic oil-in-water emulsion, wherein the particle comprises: (a) 0.2-10% (v/v) squalene core that is in liquid phase at 25° C., (b) 0.5-5.0 mg/ml of a cationic lipid, such that the overall net charge of the emulsion particle prior to RNA complexation is positive, (c) 0.01-2.5% (v/v) of a non-ionic surfactant and wherein said RNA molecule encodes a protein antigen and said RNA is anchored to the surface of said particle by non-covalent interactions;

wherein, when administered in an effective amount to a mammal, the composition elicits antibody titers to the antigen equal to or greater than the RNA administered to the mammal not complexed with the particle, further wherein the RNA does not include modified nucleobases, other than an optional 5' cap.

28. The composition of claim 27, wherein the cationic lipid is selected from 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl ($C_{16:0}$)trimethyl ammonium propane (DPTAP), N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), or a combination of the foregoing.

29. The composition of claim 27, wherein the cationic lipid is selected from DOTAP, DDA, DC cholesterol, or a combination thereof.

30. The composition of claim 29, wherein the non-ionic surfactant is selected from polysorbate 80, sorbitan trioleate, or a combination thereof.

31. The composition of claim 30, wherein, when administered in an effective amount to a mammal, the composition elicits antibody titers to the antigen equal to or greater than the RNA administered to the mammal: i) not complexed with the particle and ii) at a 10-fold higher concentration, relative to the complexed RNA.

32. The composition of claim 31, wherein the cationic lipid is DOTAP.

* * * * *